US009611284B2

(12) United States Patent
Young et al.

(10) Patent No.: US 9,611,284 B2
(45) Date of Patent: Apr. 4, 2017

(54) PROSTAGLANDIN-BISPHOSPHONATE CONJUGATE COMPOUNDS, METHODS OF MAKING SAME, AND USES THEREOF

(71) Applicant: Simon Fraser University, Burnaby (CA)

(72) Inventors: Robert N. Young, Vancouver (CA); Stephen Arns, North Vancouver (CA); Anne Moreau, Le Perreux-sur-Marne (FR); Mohammed Monzur Morshed, Mississauga (CA); Romelo Gibe, Singapore (SG)

(73) Assignee: Simon Fraser University, Burnaby (CA)

( * ) Notice: Subject to any disclaimer, the term of this patent is extended or adjusted under 35 U.S.C. 154(b) by 799 days.

(21) Appl. No.: 13/687,762

(22) Filed: Nov. 28, 2012

(65) Prior Publication Data

US 2013/0157984 A1 Jun. 20, 2013

Related U.S. Application Data

(63) Continuation-in-part of application No. PCT/CA2011/000633, filed on May 30, 2011.

(60) Provisional application No. 61/349,694, filed on May 28, 2010.

(30) Foreign Application Priority Data

Apr. 21, 2011 (CA) ..................................... 2738045

(51) Int. Cl.
| | | |
|---|---|---|
| *C07F 9/572* | (2006.01) | |
| *A61K 47/48* | (2006.01) | |
| *C07F 9/6558* | (2006.01) | |
| *C07F 9/59* | (2006.01) | |
| *C07F 9/6512* | (2006.01) | |
| *C07F 9/38* | (2006.01) | |

(52) U.S. Cl.
CPC ...... *C07F 9/5722* (2013.01); *A61K 47/48084* (2013.01); *C07F 9/3873* (2013.01); *C07F 9/5721* (2013.01); *C07F 9/5727* (2013.01); *C07F 9/598* (2013.01); *C07F 9/65127* (2013.01); *C07F 9/65583* (2013.01)

(58) Field of Classification Search
CPC .................................................. C07F 9/5722
See application file for complete search history.

(56) References Cited

U.S. PATENT DOCUMENTS

| | | | |
|---|---|---|---|
| 4,320,136 A * | 3/1982 | Scribner ...................... 514/424 |
| 4,922,007 A | 5/1990 | Kieczykowski et al. |
| 5,019,651 A | 5/1991 | Kieczykowski |
| 5,409,911 A * | 4/1995 | Tyler et al. ...................... 514/91 |
| 5,510,517 A | 4/1996 | Dauer et al. |
| 5,648,491 A | 7/1997 | Dauer et al. |
| 6,121,253 A | 9/2000 | Han et al. |
| 7,109,223 B2 | 9/2006 | Han et al. |
| 7,238,710 B2 | 7/2007 | Billot et al. |
| 2005/0239872 A1* | 10/2005 | Billot ................. A61K 31/4015 514/425 |
| 2006/0258726 A1 | 11/2006 | Billot et al. |

FOREIGN PATENT DOCUMENTS

| | | |
|---|---|---|
| CA | 2648159 A1 | 10/2007 |
| EP | 0855389 A2 | 7/1998 |
| EP | 1114816 A1 | 7/2001 |
| EP | 1132086 A2 | 9/2001 |
| WO | WO-01/46140 A1 | 6/2001 |
| WO | WO-01/72268 A1 | 10/2001 |
| WO | WO-02/24647 A1 | 3/2002 |
| WO | WO-02/42268 A2 | 5/2002 |
| WO | WO-03/047417 A2 | 6/2003 |
| WO | WO-2005/116010 A1 | 12/2005 |
| WO | WO-2011/147034 A1 | 12/2011 |

OTHER PUBLICATIONS

English translation of Office Action for Japanese Application No. 2013-511491, mailed Mar. 25, 2015 (5 pages).
Arns et al., "Asymmetric [3H]-labeling using ruthenium catalyzed transfer hydrogenation," J Labelled Comp Radiopharm. 53(4):205-7 (2010).
Arns et al., "Design and synthesis of novel bone-targeting dual-action pro-drugs for the treatment and reversal of osteoporosis," Bioorg Med Chem. 20(6):2131-40 (2012).
Arns et al., "Development of Dual Prodrug Conjugates for the Treatment of Osteoporosis," 93rd Canadian Chemistry Conference and Exhibition, 2010 (1 page).
Brümmer et al., "Antibody-catalyzed hydrolysis of oligomeric esters: a model for the degradation of polymeric materials," Chem Commun. 19-20 (2001).
Gediya et al., "Design, synthesis, and evaluation of novel mutual prodrugs (hybrid drugs) of all-trans-retinoic acid and histone deacetylase inhibitors with enhanced anticancer activities in breast and prostate cancer cells in vitro," J Med Chem. 51(13):3895-904 (2008).
Liu et al., "Effects of a New Anabolic Drug in Treating Postmenopausal Osteoporosis Using the Ovariectomized Rat Model," ASBMR 2013 Annual Meeting (2013).
International Preliminary Report on Patentability for International Application No. PCT/CA2011/000633, dated Dec. 4, 2012 (8 pages).
International Search Report and Written Opinion for International Application No. PCT/CA2011/000633, mailed Sep. 7, 2011 (12 pages).
EPO Supplementary European Search Report for European Application No. 11785955.3, dated Oct. 4, 2013 (8 pages).

* cited by examiner

*Primary Examiner* — Joseph Kosack
(74) *Attorney, Agent, or Firm* — Clark & Elbing LLP

(57) ABSTRACT

The invention provides in part, conjugate compounds. The invention also provides synthesis methods for making the compounds, and uses of the compounds.

10 Claims, 2 Drawing Sheets

PROSTAGLANDIN-BISPHOSPHONATE CONJUGATE COMPOUNDS, METHODS OF MAKING SAME, AND USES THEREOF

CROSS-REFERENCE TO RELATED APPLICATIONS

This application is a continuation-in-part of International Application No. PCT/CA2011/000633, filed May 30, 2011, which is hereby incorporated by reference in its entirety. This application claims the benefit of U.S. Application No. 61/349,694, filed May 28, 2010, and Canadian Application No. 2,738,045, filed Apr. 21, 2011.

FIELD OF INVENTION

The present invention relates to conjugate compounds and methods of making and using same.

BACKGROUND OF THE INVENTION

Prostaglandins are a sub-class of eicosanoids found in most body tissues and implicated in a variety of physiological functions in animals, including smooth muscle contraction, reproduction, autoimmunity, inflammation, reduction of intraocular pressure, etc. Prostaglandin $E_2$ ($PGE_2$) has been associated with various physiological and/or pathological conditions such as stimulation of bone formation, increase in bone mass, arthritis, pain, inflammation, cancer, multiple sclerosis, etc.

$PGE_2$ binds to four receptors (EP1, EP2, EP3 and EP4). The EP4 receptor is associated with intracellular cyclic adenosine monophosphate (cAMP) production, and is distributed in a wide variety of tissue types suggesting a major role in $PGE_2$-mediated biological events, such as smooth muscle relaxation, intraocular pressure, pain (in particular inflammatory, neuropathic and visceral pain), inflammation, neuroprotection, lymphocyte differentiation, bone metabolic processes, allergic activities, promotion of sleep, renal regulation, gastric or enteric mucus secretion and duodenal bicarbonate secretion.

A variety of EP4 agonists have been described and include, without limitation, compounds as set forth in, for example, WO 02/24647, WO 02/42268, EP 1132086, EP 855389, EP 1114816, WO 01/46140, WO 01/72268, WO 05/116010, WO 03/047417, or U.S. Pat. No. 7,238,710. Many EP4 agonists have however been associated with systemic side effects.

Bisphosphonates are drugs used to strengthen bone and have been implicated in inhibiting bone resorption and bone targeting.

Prostaglandin-bisphosphonate conjugate compounds have been described in for example U.S. Pat. No. 5,409,911 or U.S. Pat. No. 6,121,253.

SUMMARY OF THE INVENTION

The invention provides, in part, conjugate compounds. The invention also provides synthesis methods for making the compounds, and uses of the compounds.

In one aspect, the invention provides a compound according to Formula I, or a pharmaceutically acceptable salt thereof:

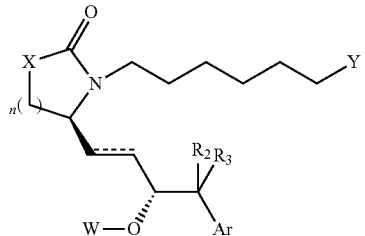

Formula I where X may be —C—, —S—, —O—, or —NH—; $R_2$ and $R_3$ may each independently be —H or halo; Ar may be aryl; W may be —H, —C(O)V, or —C(O)OV; Y may be optionally substituted tetrazole, —C(O)$OR_1$, or —C(O)$NHSO_2R'$; n may be 1, 2 or 3; V may be optionally substituted lower alkyl, optionally substituted aryl, or optionally substituted heteroalkyl; $R_1$ may be H or optionally substituted lower alkyl; R' may be optionally substituted lower alkyl or optionally substituted aryl; and --- is a double or single bond, and where Y or W is conjugated to a bisphosphonate moiety.

In alternative embodiments, the bisphosphonate moiety may be conjugated via a linker.

In alternative embodiments, $R_1$ may be —($CR_5R_6$)—O—C(O)—O—Ar, wherein Ar may be optionally substituted aryl, $R_5$ may be H or lower alkyl, and $R_6$ may be H or lower alkyl.

In alternative embodiments, $R_1$ may be —($CR_5R_6$)—O—C(O)—NH—($CH_2$)$_m$—C($PO_3H_2$)$_2$OH, where $R_5$ may be H or lower alkyl; $R_6$ may be H or lower alkyl and m may be 1, 2, 3, 4, 5, or 6.

In alternative embodiments, when W is H, Y is optionally substituted tetrazole and X is $CH_2$.

In alternative embodiments, Y may be —C(O)$OR_1$; W may be

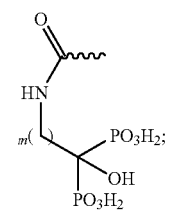

m may be 1, 2, 3, 4, 5, or 6; and $R_1$ may be lower alkyl.

In alternative embodiments, Y may be —C(O)$OR_1$, tetrazole, or N-trityl-tetrazole; W may be

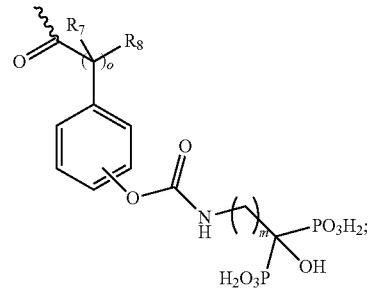

$R_7$ and $R_8$ may be each independently H, small alkyl, cycloalkyl group or $CF_3$; m may be 1, 2, 3, 4, 5, or 6; and o may be 0, 1, 2, 3, 4, 5, or 6.

In alternative aspects, the invention provides a compound according to Formula IV or V, or a pharmaceutically acceptable salt thereof:

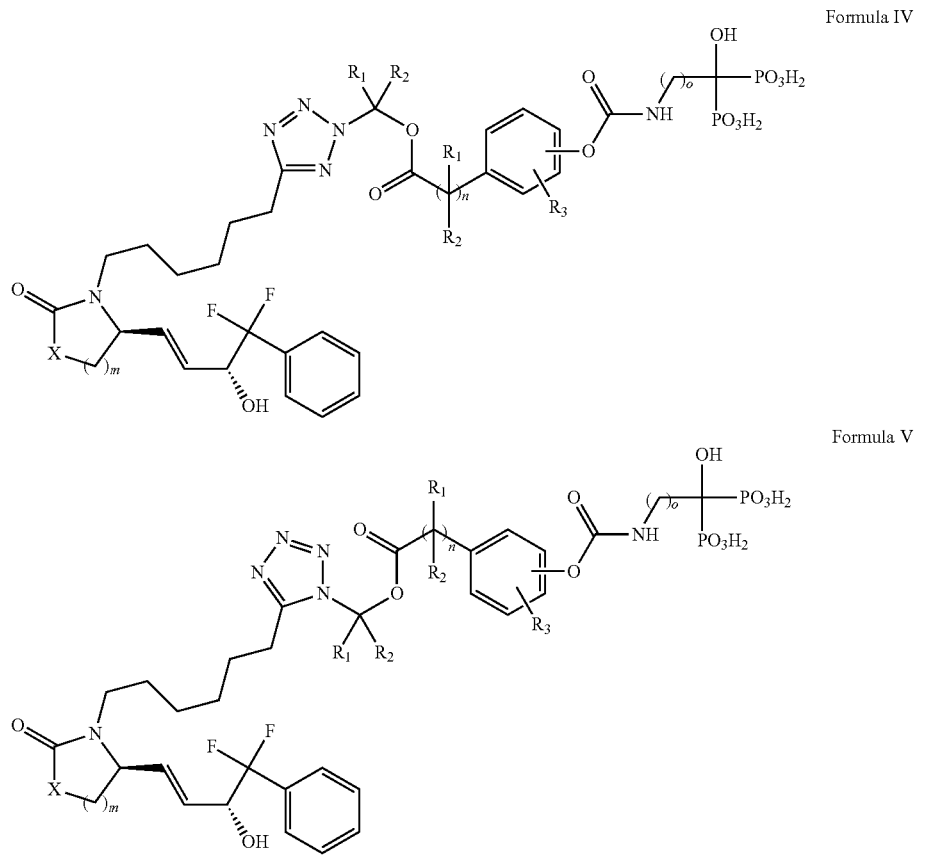

Formula IV

Formula V where X may be —C—, —S—, —O—, or —NH—; $R_1$ and $R_2$ may be each independently H, small alkyl, cycloalkyl group or $CF_3$; $R_3$ may be a electron donating or electron withdrawing group; m may be 1, 2, or 3; n may be 1, 2, 3, or 4; and o may be 1, 2, 3, or 4.

In alternative embodiments, the compound may be hydrolysable in vivo. In alternative embodiments, the compound may be inactive prior to hydrolysation and/or may be active subsequent to hydrolysation.

In alternative aspects, the invention provides a composition comprising a compound according to the invention in combination with a carrier.

In alternative aspects, the invention provides a pharmaceutical composition comprising a compound according to the invention, in combination with a pharmaceutically acceptable carrier.

In alternative aspects, the invention provides methods of selectively delivering a compound to bone or an associated site, the method comprising administering an effective amount of a compound or composition according to the invention to a subject in need thereof.

In alternative embodiments, the associate site comprises a site adjacent to a bone in need of treatment. In alternative embodiments, the bone in need of treatment may be a green stick fracture, compound fracture, lateral fracture, pathologic fracture resulting from an invasive tumor, compression fracture, or a fracture requiring a surgical procedure for realignment of a bone.

In alternative aspects, the invention provides methods of treating or preventing a condition associated with abnormal or excessive bone loss, or with abnormal or reduced bone resorption, or with abnormal calcium metabolism comprising administering an effective amount of a compound or composition according to the invention to a subject in need thereof.

In alternative aspects, the invention provides for the use a compound or composition according to the invention for treating or preventing a condition associated with abnormal or excessive bone loss, or with abnormal or reduced bone resorption, or with abnormal calcium metabolism in a subject in need thereof.

In alternative embodiments, the condition may be selected from the group consisting of osteoporosis (such as glucocorticoid-induced osteoporosis), Paget's disease, abnormally increased bone turnover, bone graft, periodontal disease, alveolar bone loss, tooth loss, bone fracture, periprostheticosteolysis, osteogenesisimperfecta, and metastatic bone disease.

In alternative embodiments, the subject may be a human.

In alternative aspects, the invention provides a method of making a compound according to the invention by providing a EP4 agonist having a C-1 carboxyl group or tetrazoyl moiety, providing a bisphosphonate with a free primary or secondary amino moiety; and conjugating the EP4 agonist and the bisphosphonate. In some embodiments, the invention provides a compound made by such a method.

In alternative aspects, the invention provides a method of selectively delivering a conjugate compound to bone or an associated site, by administering an effective amount of a compound according to the invention or a pharmaceutically acceptable salt thereof to a subject in need thereof.

In alternative aspects, the invention provides a method of treating or preventing a condition associated with abnormal or excessive bone loss, or with abnormal or reduced bone resorption, or with abnormal calcium metabolism comprising administering an effective amount of a conjugate compound according to the invention or a pharmaceutically acceptable salt thereof to a subject in need thereof.

In alternative aspects, the invention provides for use of an effective amount of a conjugate compound according to the invention or a pharmaceutically acceptable salt thereof for treating or preventing a condition associated with abnormal or excessive bone loss, or with abnormal or reduced bone resorption, or with abnormal calcium metabolism in a subject.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
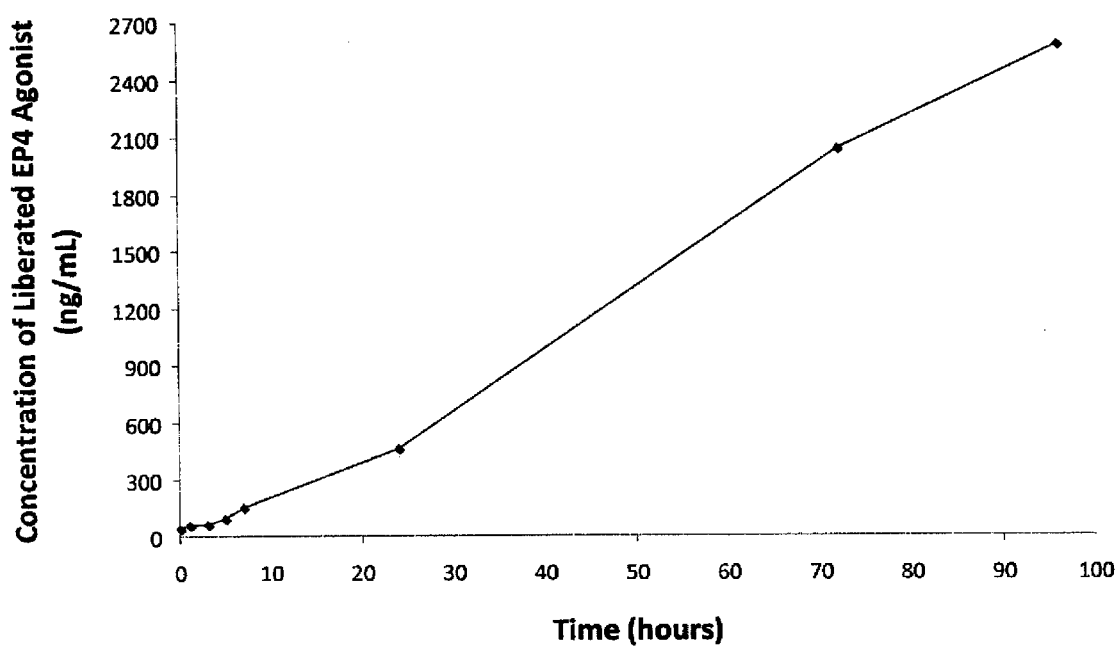
FIG. 1 is a graph showing hydrolysis of the conjugate 6 and liberation of 1 in rat plasma at 37° C.

The invention provides, in part, amino-bisphosphonate conjugated compounds and uses thereof, methods of making same, and intermediates used in the methods of making the compounds. In alternative embodiments, the invention provides derivatized EP4 agonist compounds and uses thereof, methods of making same, and intermediates used in the methods of making the derivatized EP4 agonist compounds. In alternative embodiments, the invention provides novel EP4 agonist-bisphosphonate conjugate compounds and uses thereof, methods of making same, and intermediates used in the methods of making the EP4 agonist-bisphosphonate conjugate compounds. In alternative embodiments, the conjugate compounds provide simultaneous delivery of the bisphosphonate and the agent conjugated to the bisphosphonate to a site of action, such as bone. For example, the EP4 agonist-bisphosphonate conjugate compounds provide simultaneous delivery of the EP4 agonist and the bisphosphonate to a site of action, such as bone.

In some embodiments, the conjugate compounds are hydrolyzable in vivo to release the bisphosphonate and the agent conjugated to the bisphosphonate. For example, the EP4 agonist-bisphosphonate conjugate compounds are hydrolyzable in vivo to release the EP4 agonist and bisphosphonate components.

In alternative embodiments, the conjugate compounds are inactive until hydrolyzed and the bisphosphonate and the agent conjugated to the bisphosphonate are released. For example, EP4 agonist-bisphosphonate conjugate compounds are inactive until hydrolyzed and the EP4 agonist and bisphosphonate components released. In alternative embodiments, the agent conjugated to the bisphosphonate (e.g., an EP4 agonist) and the bisphosphonate are each individually active upon release, as measured by standard procedures for each. By "release" as used herein is meant the liberation of the bisphosphonate and the agent conjugated to the bisphosphonate such as by hydrolysis or enzyme action, from a conjugate compound. In alternative embodiments, by "release" as used herein is meant the liberation of an EP4 agonist moiety and a bisphosphonate moiety, for example, by hydrolysis or enzyme action, from an EP4 agonist-bisphosphonate conjugate compound as described herein. In alternative embodiments, at least about 5% to about 100%, for example, about 5%, 10%, 15%, 20%, 25%, 30%, 35%, 40%, 45%, 50%, 55%, 60%, 65%, 70%, 75%, 80%, 85%, 90%, 95%, or 100% or any value therebetween, of the EP4 agonist or other agent moiety and/or the bisphosphonate moiety is released in a suitable period of time. The release may be measured, for example, in blood or plasma, after the conjugate has become bound to bone in vivo, or in any suitable system or assay described herein or known in the art. In alternative embodiments, the release may take a period of time, for example, about 1 day to about 30 days, or any value or set of values between this range, for example, about 7 days to about 14 days, such as about 7, 8, 9, 10, 11, 12, 13, or 14 days. In some embodiments, the release may differ from in plasma and from bone. Accordingly, in some embodiments, a conjugate compound that is stable or exhibits slow release in plasma would be useful in that it would allow for binding to bone prior to release of the individual components. In alternative embodiments, the ability of the conjugate compound to be targeted to bone and to be released from it may be the determinative characteristic.

In some embodiments, the EP4 agonist or other agent-bisphosphonate conjugate compounds may be delivered directly to bone.

In some embodiments, the EP4 agonist or other agent-bisphosphonate conjugate compounds reduce the systemic side effects associated with EP4 agonists or other agents.

In alternative embodiments, the EP4 agonist or other agent-bisphosphonate conjugate compounds may be administered at lower doses compared to each of the individual components.

In alternative embodiments, the EP4 agonist-bisphosphonate conjugate compounds combine bone growth stimulating EP4 receptor selective agonists and bone resorption inhibiting amino-bisphosphonates in bone targeting pro-drugs which, on systemic administration, bind to bone and enzymatically liberate both of the two components in situ slowly over time thus avoiding or reducing the systemic side effects associated with EP4 agonists. In some embodiments, the conjugate compounds according to the invention are hydrolyzed at a rate that allows for dosing once a week.

The actions of the EP4 agonist or other agent and the bisphosphonate may be additive or synergistic.

In alternative embodiments, the invention provides methods to directly couple tetrazoles with primary or secondary amines to provide dual pro-drugs which, when hydrolyzed, release the two components intact. For example, the invention provides methods to directly couple the tetrazole moieties of, for example, an EP4 agonist or other agent, with primary or secondary amines to provide dual pro-drugs which, when hydrolyzed, release the two components intact.

In alternative embodiments, the invention provides methods to directly couple the carboxylic acid moieties of, for example, an EP4 agonist or other agent, with primary or secondary amines to provide dual pro-drugs which, when hydrolyzed, release the two components intact.

In alternative embodiments, the invention provides methods to directly couple the alcohol moieties of, for example, EP4 agonists or other agents, with primary or secondary amines to provide dual pro-drugs which, when hydrolyzed, release the two components intact.

Conjugates and Preparation Thereof

By "bisphosphonate" as used herein is meant an amino-bisphosphonate compound. Any known bisphosphonate which has an secondary or primary amine functionality capable of coupling to an EP4 agonist or other agent and which targets in vivo to bone may be used, whether or not that particular bisphosphonate has bone resorption inhibiting activity or is useful in the treatment of a disorder as described herein.

In some embodiments, bisphosphonates may have the following general structure, where m may be 1, 2, 3, 4, 5 or 6.

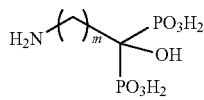

A "bisphosphonate moiety" as used herein is the portion of a bisphosphonate that is conjugated via the amino group to another compound, such as an EP4 agonist or other agent. By "conjugated" is meant the linkage of a bisphosphonate and an agent conjugated to the bisphosphonate, generally via a linker such as those described herein or known in the art. In general, the linkage is releasable and occurs in situ after binding of the conjugated compound to bone.

Bisphosphonates include, without limitation, alendronic acid, 4-amino-1-hydroxybutylidene-1,1-bisphosphonic acid; alendronate (also known as alendronate sodium or alendronate monosodium trihydrate), 4-amino-1-hydroxybutylidene-1,1-bisphosphonic acid monosodium trihydrate; alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997; 6-amino-1-hydroxyhexylidene-1,1-bisphosphonic acid (neridronate); 3-amino-1-hydroxypropylidene-1,1-bisphosphonic acid (pamidronate); or pharmaceutically acceptable salts thereof, or mixtures thereof.

EP4 agonists include, without limitation, compounds containing a carboxyl or tetrazole group or an alcohol group, as set forth in, for example, WO 02/24647, WO 02/42268, EP 1132086, EP 855389, EP 1114816, WO 01/46140, WO 01/72268, etc. In some embodiments, EP4 agonists having a hydroxyl group at position 15, or a carboxylic acid or tetrazole group at position 1, may be reacted with an amino bisphosphonate as described herein.

Examples of EP4 agonists include compounds 1 and 2 and examples of clinically active bisphosphonates (BPs) include alendronate/alendronic acid (3), pamidronate (4) or neridronate (5).

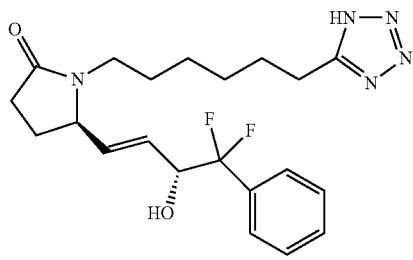

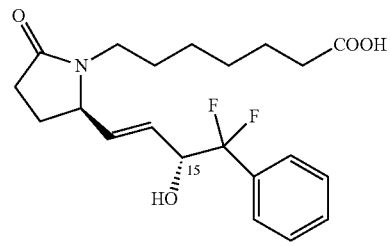

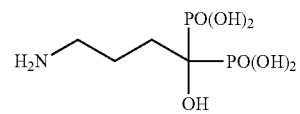

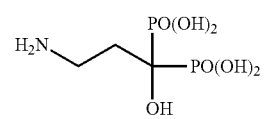

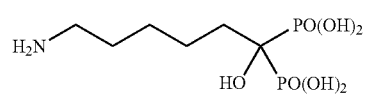

In some embodiments, compounds according to the invention include a compound according to Formula I, or a pharmaceutically acceptable salt thereof:

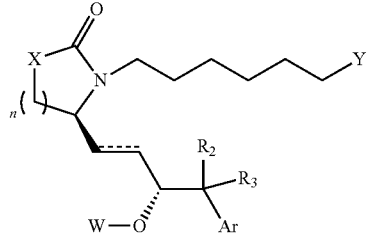

Formula I wherein:
X may be —C—, —S—, —O—, or —NH—;
$R_2$ and $R_3$ may be each independently —H or halo;
Ar is aryl;
W may be —H, —C(O)V, or —C(O)OV;
Y may be optionally substituted tetrazole, —C(O)OR$_1$, or —C(O)NHSO$_2$R';
n may be 1, 2 or 3;
V may be optionally substituted lower alkyl, optionally substituted aryl, or optionally substituted heteroalkyl;
$R_1$ may be H or optionally substituted lower alkyl;
R' may be optionally substituted lower alkyl or optionally substituted aryl; and
--- is a double or single bond,
and wherein Y or W is conjugated to a bisphosphonate moiety.

In some embodiments, in Formula I, $R_1$ may be —$(CR_5R_6)$—O—C(O)—O—Ar, where Ar may be optionally substituted aryl, $R_5$ may be H or lower alkyl, $R_6$ may be H or lower alkyl.

In alternative embodiments, in Formula I, $R_1$ may be —$(CR_5R_6)$—O—C(O)—NH—$(CH_2)_m$—$C(PO_3H_2)_2OH$, where $R_5$ may be H or lower alkyl; $R_6$ may be H or lower alkyl; m may be 1, 2, 3, 4, 5, or 6.

In some embodiments, in Formula I, when W is H, Y is optionally substituted tetrazole and X is $CH_2$.

In some embodiments, in Formula I, the C1-C7 chain group may include a double bond, for example, at the C5-C6 position and may be cis or trans. In alternative embodiments, in Formula I, the C1-C7 chain group may include a heteroatom, such as O or S or as described herein.

In some embodiments, a compound according to Formula I specifically excludes compound 8:

Compound 8

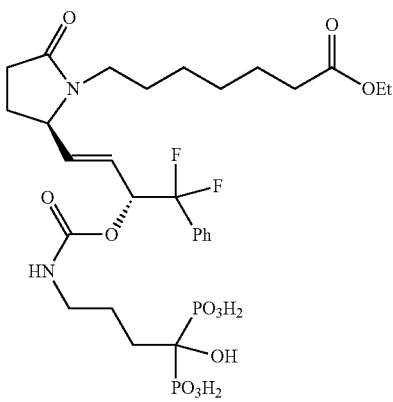

In some embodiments, compounds according to the invention include a compound according to Formula II, or a pharmaceutically acceptable salt thereof:

Formula II

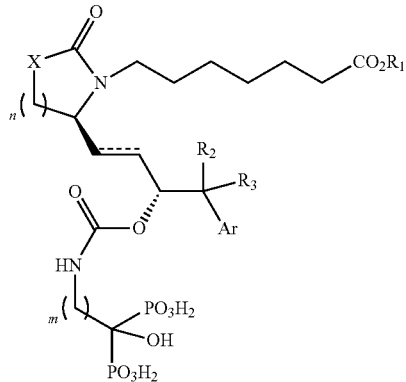

wherein:
X may be —C—, —S—, —O—, or —NH—;
$R_2$ and $R_3$ may be each independently —H or halo;
Ar is aryl;
n may be 1, 2 or 3;
m may be 1, 2, 3, 4, 5, or 6;
$R_1$ may be H or lower alkyl; and
--- is a double or single bond.

In some embodiments, in a compound according to Formula II, when $R_1$ is Et; $R_2$ and $R_3$ are F, and Ar is phenyl, X may be —S—, —O—, or —NH—; n may be 2 or 3; and m may be 1, 2, 4, 5 or 6.

In some embodiments, a compound according to Formula II specifically excludes compound 8:

Compound 8

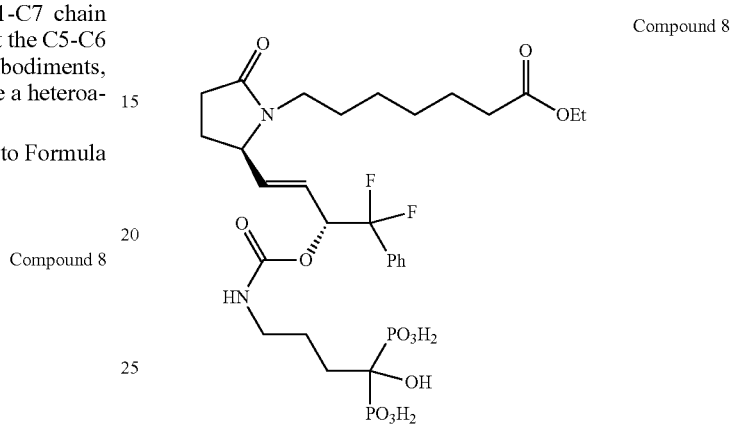

In some embodiments, compounds according to the invention include a compound according to Formula III, or a pharmaceutically acceptable salt thereof:

Formula III

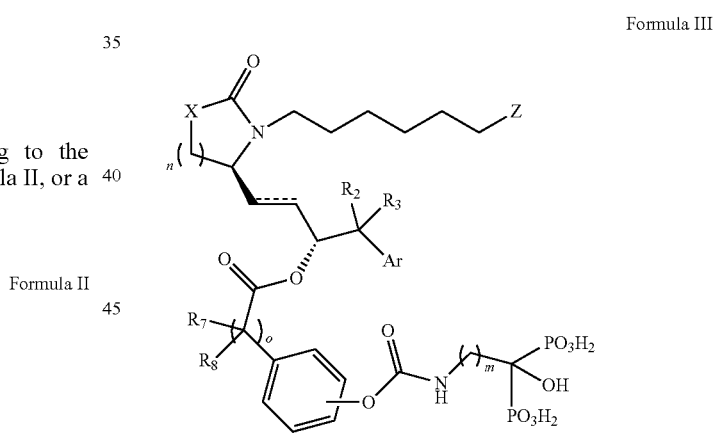

wherein:
X may be —C—, —S—, —O—, or —NH—;
$R_2$ and $R_3$ may be each independently —H or halo;
Ar is aryl;
n may be 1, 2 or 3;
$R_7$ and $R_8$ may each be independently H, small alkyl, cycloalkyl group or $CF_3$;
m may be 1, 2, 3, 4, 5 or 6;
o may be 0, 1, 2, 3, 4, 5, or 6;
Z may be $COOR_1$, tetrazole, or N-trityl-tetrazole;
$R_1$ may be H or optionally substituted lower alkyl; and
--- is a double or single bond.

In some embodiments, compounds according to the invention include a compound according to Formula IV or Formula V, or a pharmaceutically acceptable salt thereof:

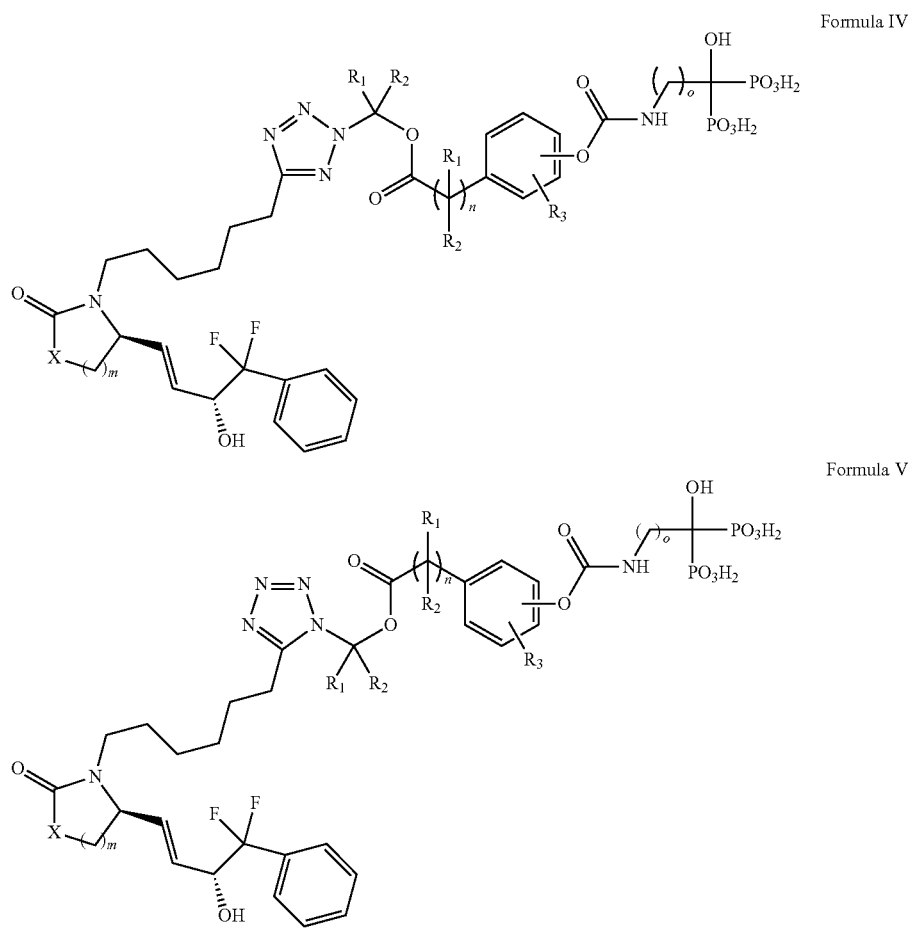

wherein:

$R_1$ and $R_2$ may be H, small alkyl, cycloalkyl group or $CF_3$;
$R_3$ may be one or more multiple electron donating and electron withdrawing groups on the aromatic system. Electron Withdrawing groups (EWG) include without limitation 4-$NO_2$, 2,4-di$NO_2$, F, etc. Electron Donating groups (EDG) include without limitation $OCH_3$, OR or $NR_2$ where "R" is lower alkyl, etc.
m may be 1, 2, or 3;
n may be 1, 2, 3, or 4; and
o may be 1, 2, 3, or 4.

"Alkyl" as used herein refers to a straight or branched hydrocarbon chain group consisting solely of carbon and hydrogen atoms, containing no unsaturation and including, for example, from one to ten carbon atoms, and which is attached to the rest of the molecule by a single bond. Unless stated otherwise specifically in the specification, the alkyl group may be optionally substituted by one or more substituents as described herein. Unless stated otherwise specifically herein, it is understood that the substitution can occur on any carbon of the alkyl group. Examples of straight or branched chain alkyl groups include, but are not limited to, methyl, trifluoromethyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, 1-heptyl, or 1-octyl.

By a "ring structure" is meant a cycloalkyl, aryl, heteroaryl, or any cyclic structure that may be optionally substituted.

"Aryl" as used herein refers to a monocylic or bicycled ring structure wherein all rings are aromatic and are formed of carbon atoms, for example, phenyl or naphthyl groups. Unless stated otherwise specifically herein, the term "aryl" is meant to include aryl groups optionally substituted by one or more substituents as described herein. Accordingly, in some embodiments, the term "aryl" may refer to heteroaryl with, for example, rings of 5 or 6 or more atoms containing one or two heteroatoms such as N, S, or O.

"Halo" refers to halogen groups such as bromo, chloro, fluoro, iodo, etc. In some embodiments, suitable halogens include fluorine.

Any group described herein may be substituted or unsubstituted. When substituted, a group may be substituted with any desired substituent or substituents such as one or more of the following group: H, alkyl ($C_{1-10}$), alkenyl ($C_{2-10}$), alkynyl ($C_{2-10}$), aryl (5-12 members), arylalkyl, arylalkenyl, or arylalkynyl, each of which may optionally contain one or more heteroatoms selected from O, S, P, N, F, Cl, Br, I, or B, and each of which may be further substituted, for example, by =O; or optionally substituted forms of acyl, arylacyl, alkyl-alkenyl-, alkynyl- or arylsulfonyl and forms thereof which contain heteroatoms in the alkyl, alkenyl, alkynyl or aryl moieties; halogen (e.g., chloro, iodo, bromo, or fluoro); hydroxyl; $C_{1-10}$alkoxyl; amino (primary, secondary, or tertiary); nitro; thiol; thioether; imine; cyano; amido; carbamoyl; phosphonato; bisphosphonate; phosphine; carboxyl; thiocarbonyl; sulfonyl; sulfonamide; ketone; aldehyde; ester; oxo; haloalkyl (e.g., trifluoromethyl); cycloalkyl, which may be monocyclic or fused or non-fused polycyclic (e.g., cyclopropyl, cyclobutyl, cyclopentyl, or cyclohexyl), or non-aromatic heterocyclic, which may be monocyclic or fused or non-fused polycyclic (e.g., pyrrolidinyl, piperidinyl, piperazinyl, morpholinyl, or thiazinyl); and aromatic carbocyclic or heterocyclic, monocyclic or fused or non-fused polycyclic (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl). Specific substituent groups include benzyloxy; O-alkyl; O-aryl; aryl; aryl-lower alkyl, etc. A substituted group may have 1, 2, 3, 4, 5, 6, 7, 8, 9 or 10 substituent groups. These substituent groups may optionally be further substituted with a substituent as listed herein. Substituents may also be optionally substituted by a bridge structure, for example —OC(O)O— or —OC(O)NH—. In some embodiments, substituents are not further substituted.

"Optional" or "optionally" means that the subsequently described event of circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution. Examples of optionally substituted alkyl groups include, without limitation, methyl, ethyl, propyl, etc. Similarly, "optionally substituted tetrazole" means that the tetrazole group may or may not be substituted and the description includes both substituted tetrazoles and tetrazoles having no substitution.

Compounds may be in acid, base, or salt form.

Throughout this application, it is contemplated that the term "compound" or "compounds" refers to the compounds and conjugates discussed herein and includes precursors, intermediates, and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

In some embodiments, all of the compounds of the invention contain at least one chiral center. In some embodiments, the compounds of the invention can have one or more chiral centers and/or double bonds. In some embodiments, the formulations, preparation, and compositions including compounds according to the invention can include mixtures of stereoisomers, individual stereoisomers, and enantiomeric mixtures, mixtures of multiple stereoisomers, double-bond isomers (i.e., geometric E/Z isomers) or diastereomers (e.g., enantiomers (i.e., (+) or (−)) or cis/trans isomers). In some embodiments, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. In general, the compound may be supplied in any desired degree of chiral purity.

Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

As used herein the singular forms "a", "and", and "the" include plural referents unless the context clearly dictates otherwise. For example, "a compound" refers to one or more of such compounds, and equivalents thereof as known to those skilled in the art.

EP4 agonist-bisphosphonate conjugates may be prepared as described herein or elsewhere. It is to be understood that modifications of the methods and schemes as described herein, when performed using standard techniques or achieved by routine experimentation, are encompassed herein.

In some embodiments, suitable conjugates may be prepared, for example, by linking the tetrazole, carboxylic acid or hydroxyl moiety of a compound (e.g., an anti-neoplastic agent) using bisphosphonate with a free primary or secondary amino moiety using the techniques described herein or modifications thereof.

In some embodiments, a compound according to Formula I may be prepared by:
a) providing a EP4 agonist having a C-1 carboxyl group or tetrazole moiety;
b) providing a bisphosphonate with a free primary or secondary amino moiety;
c) conjugating the EP4 agonist and the bisphosphonate.

In some embodiments, suitable conjugates may be prepared, for example, by:
1) linking the tetrazole moiety of an EP4 agonist with a bisphosphonate (e.g., where the tetrazole moiety of 1 is linked to alendronic acid through a putatively hydrolysable linker (e.g., 6 and 7));
2) linking the 15-hydroxyl group of an EP4 agonist to a bisphosphonate (e.g., the preparation of conjugates of 1 or 2 where the compound is linked to alendronic acid through the 15-hydroxyl group (e.g., 8)); or
3) where the carboxylic acid group of an EP4 agonist is linked to a bisphosphonate (e.g., the carboxylic acid group of 2 is linked to alendronic acid through a methyloxycarbonyl linking group (e.g., 9)).

6

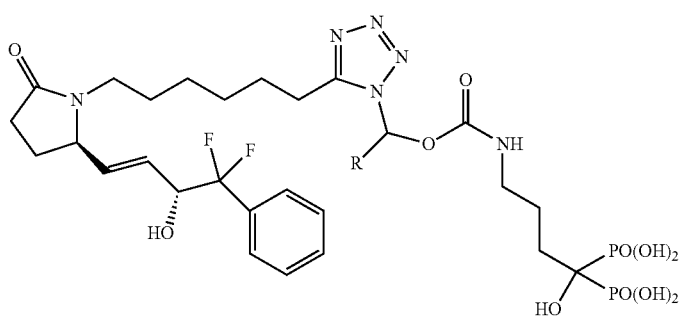

7
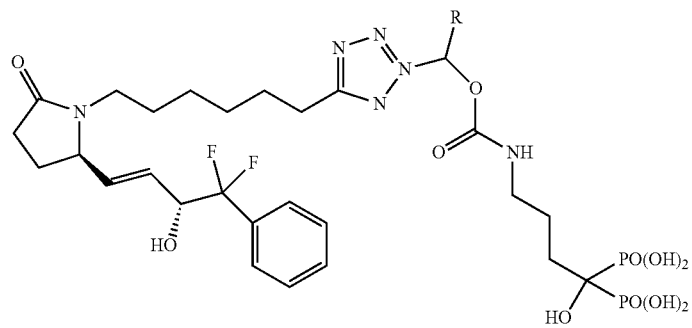
8
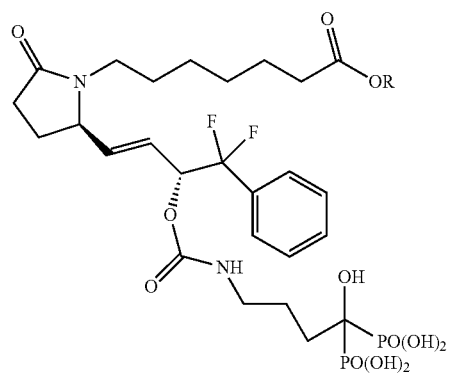
9
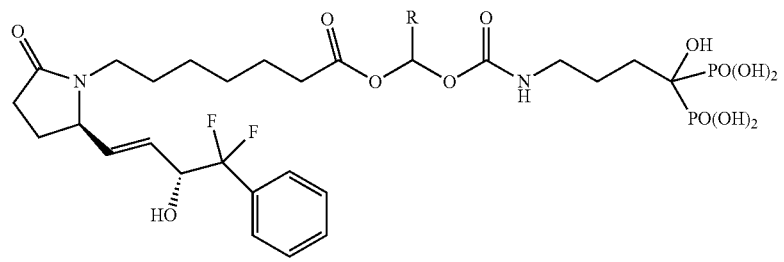
10
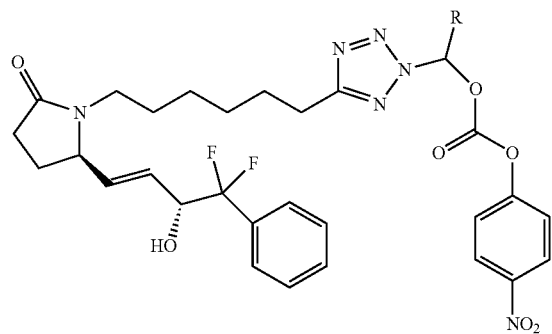
11
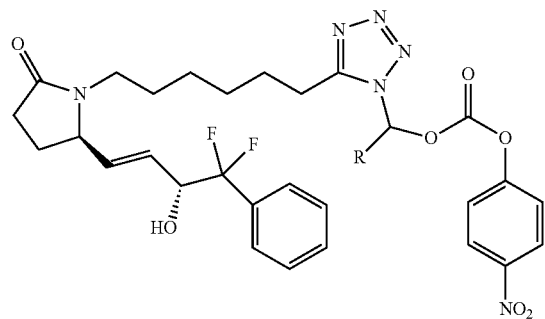

In compounds 6-11, R is H or lower alkyl.

In some embodiments, carbamate conjugates (e.g., compound F) may be prepared as set forth in Scheme I.

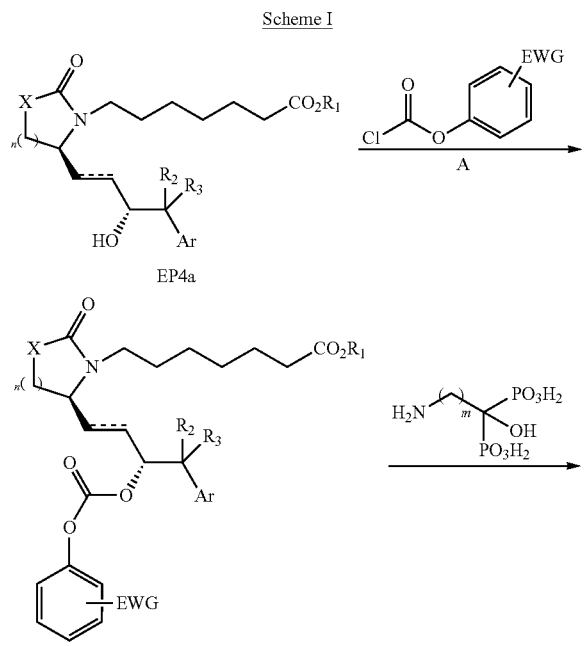

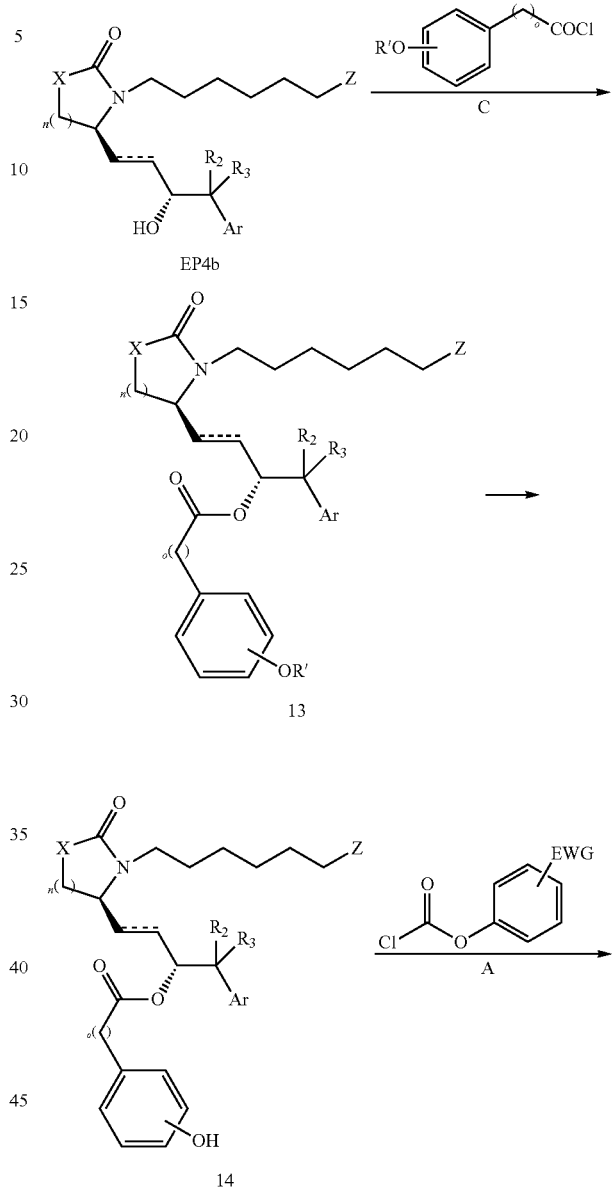

In this Scheme, the EP4 agonist of general structure EP4a is reacted with a halo-carbonyloxyaryl compound such as A in the presence of a non-nucleophilic base such as diisopropylethylamineto give the adduct E. E is then reacted with an aminoalkylbisphosphonate such as B, generally in the form of its mono-tetrabutylammonium salt in a solvent such as anhydrous DMF in the presence of an excess of non-nucleophilic base to provide the conjugate F.

In Scheme I, EWG=Electron Withdrawing group e.g. 4-$NO_2$, 2,4-di$NO_2$, F, etc.; X may be C, NH, S or O; n may be 1, 2, or 3; m may be 1, 2, 3, 4, 5, or 6; Ar is aryl; $R_1$ may be lower alkyl or H; $R_2$ may be H or F; $R_3$ may be H or F. It is to be understood that, for "m" the chain length is not critical to the synthesis and that any suitable chain length may be used.

In some embodiments, phenol-acid conjugates (e.g., compound 12) may be prepared as set forth in Scheme II.

-continued

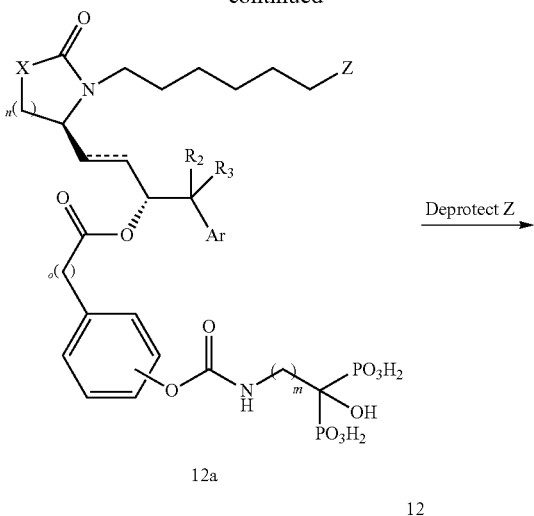

12a

12

R2 = H, F,; n = 1,2; X = C, NH, S, O;
Z = COOR1, N-trityl-tetrazole

In this Scheme, the EP4 agonist of general structure EP4b is reacted with a protected hydroxyarylalkylcarbonylchloride such as C (or other reactive form of the corresponding carboxylic acid) in the presence of a non-nucleophilic base to provide the intermediate 13. The protecting group R' is removed to provide 14 and the 14 is reacted with A in the presence of an excess of non-nucleophilic base to provide the conjugate 15. 15 is then reacted with an aminoalkylbisphosphonate such as B, generally in the form of its mono-tetrabutylammonium salt in a solvent such as anhydrous DMF in the presence of an excess of non-nucleophilic base to provide the protected conjugate 12a. When Z=N-trityl-tetrazole, it is deprotected by treatment with a strong acid such as TFA to provide 12 where Z=tetrazole.

In Scheme II, EWG=Electron Withdrawing group e.g., 4-$NO_2$, 2,4-di$NO_2$, F, etc.; X may be C, NH, S or O; n may be 1, 2 or 3; m may be 1, 2, 3, 4, 5 or 6; o may be 0, 1, 2, 3, 4, 5, or 6; Ar is aryl; Z may be $COOR_1$, tetrazole, or N-trityl-tetrazole; $R_1$ may be H or lower alkyl; $R_2$ may be H or F; $R_3$ may be H or F; R' may be H or a protecting group. It is to be understood that, for "m" the chain length is not critical to the synthesis and that any suitable chain length may be used.

In some embodiments, through-acid conjugates (e.g., compound 21) may be prepared as set forth in Scheme III.

Scheme III

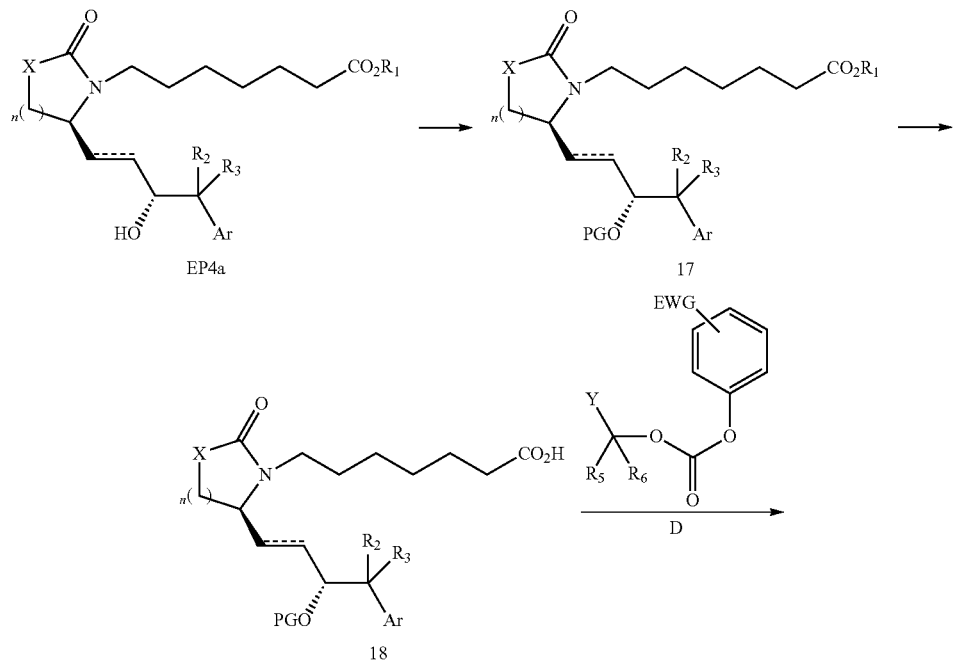

Note: PG = removable protecting group

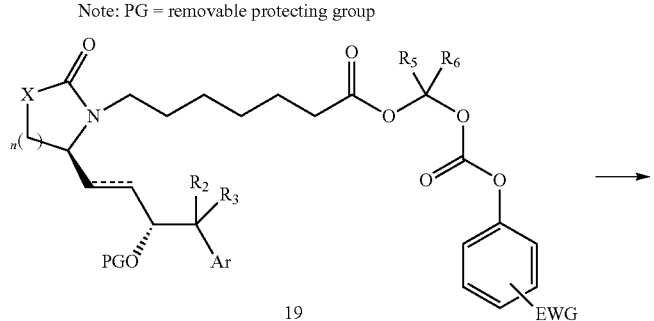

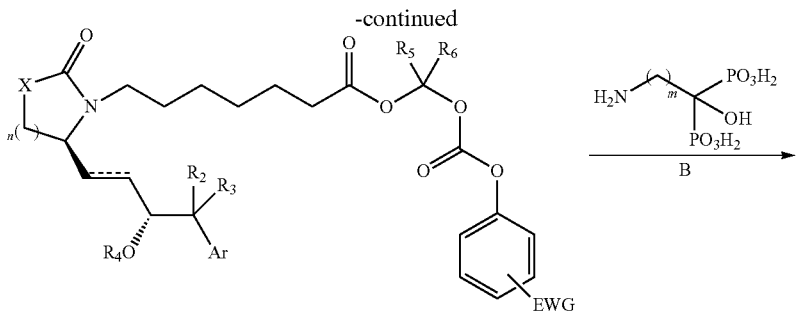

20

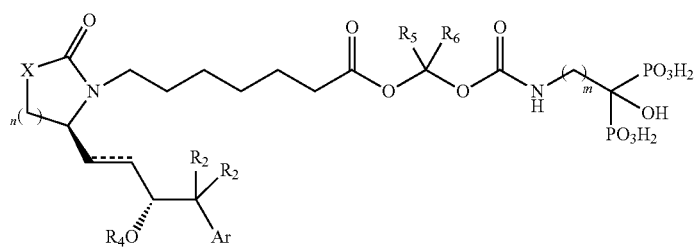

21

In this Scheme, the EP4 agonist of general formula EP4a is protected on the free hydroxyl group with a suitable removable protecting group PG and the group $R_1$ is removed and the resulting free carboxylic acid is then reacted with a haloalkyloxycarbonyloxyaryl compound such as D with catalysis with non-nucleophilic base, where the carboxylic acid is first converted to the mercury salt or the silver salt to provide the intermediate 19. The protecting group PG is removed to give 20 and then 20 is reacted with an aminoalkylbisphosphonate such as B, generally in the form of its mono-tetrabutylammonium salt in a solvent such as anhydrous DMF in the presence of an excess of non-nucleophilic base to provide the conjugate 21.

In Scheme III, EWG=Electron Withdrawing group e.g. 4-$NO_2$, 2,4-di$NO_2$, F, etc.; X may be C, NH, S or O; n may be 1, 2 or 3; m may be 1, 2, 3, 4, 5, or 6; Ar is aryl; $R_1$ may be lower alkyl or H; $R_2$ may be H or F; $R_3$ may be H or F; $R_4$ may be H or PG, where PG may be selected from a variety of removable protecting groups known in the art; $R_5$ may be lower alkyl; $R_6$ may be H or lower alkyl; Y may be halogen. It is to be understood that, for "m" the chain length is not critical to the synthesis and that any suitable chain length may be used.

Examples of conjugates prepared according to Schemes I, III, or III include those set forth in Table I.

TABLE I

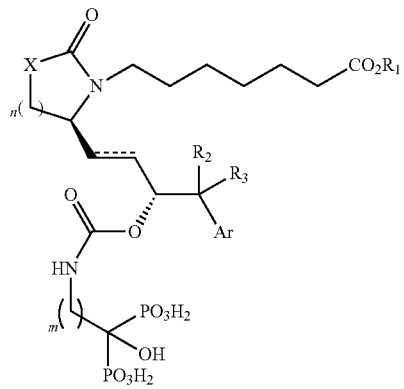

F

TABLE I-continued
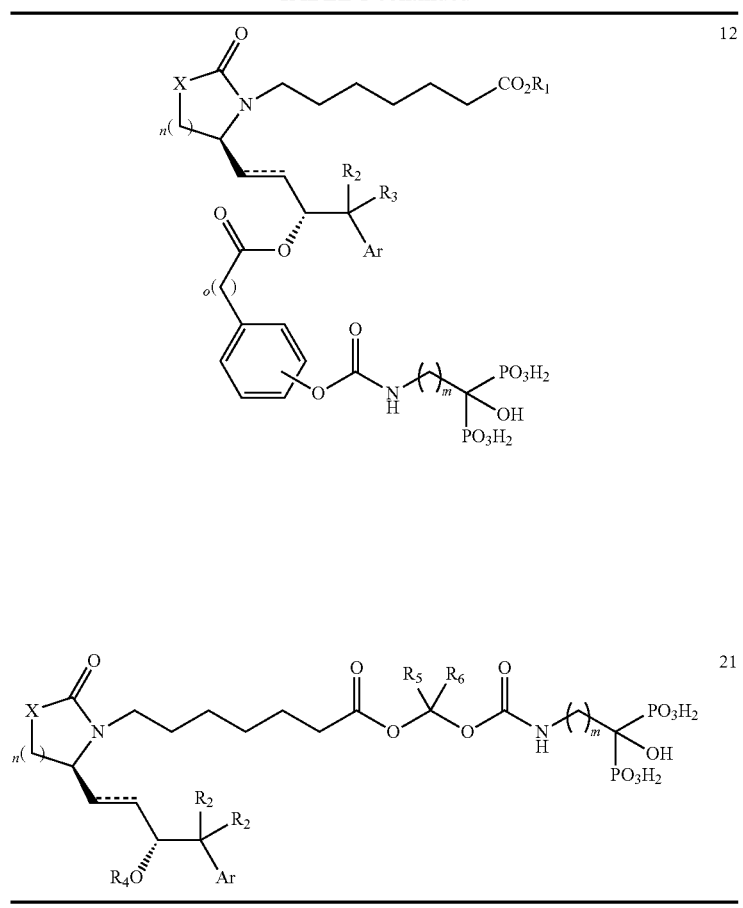
In Table I, X may be C, NH, S or O; n may be 1, 2 or 3; m may be 1, 2, 3, 4, 5, or 6; may be 0, 1, 2, 3, 4, 5, or 6; $R_1$ may be lower alkyl or H; $R_2$ may be H or F; $R_3$ may be H or F; $R_4$ may be H; $R_5$ may be H or lower alkyl; $R_6$ may be H or lower alkyl.
In alternative embodiments, other conjugates may be prepared as set forth in Scheme IV.
Scheme IV
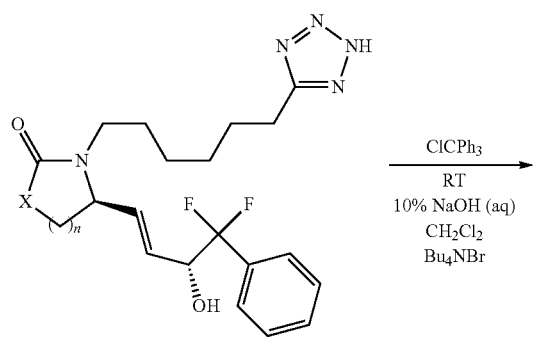

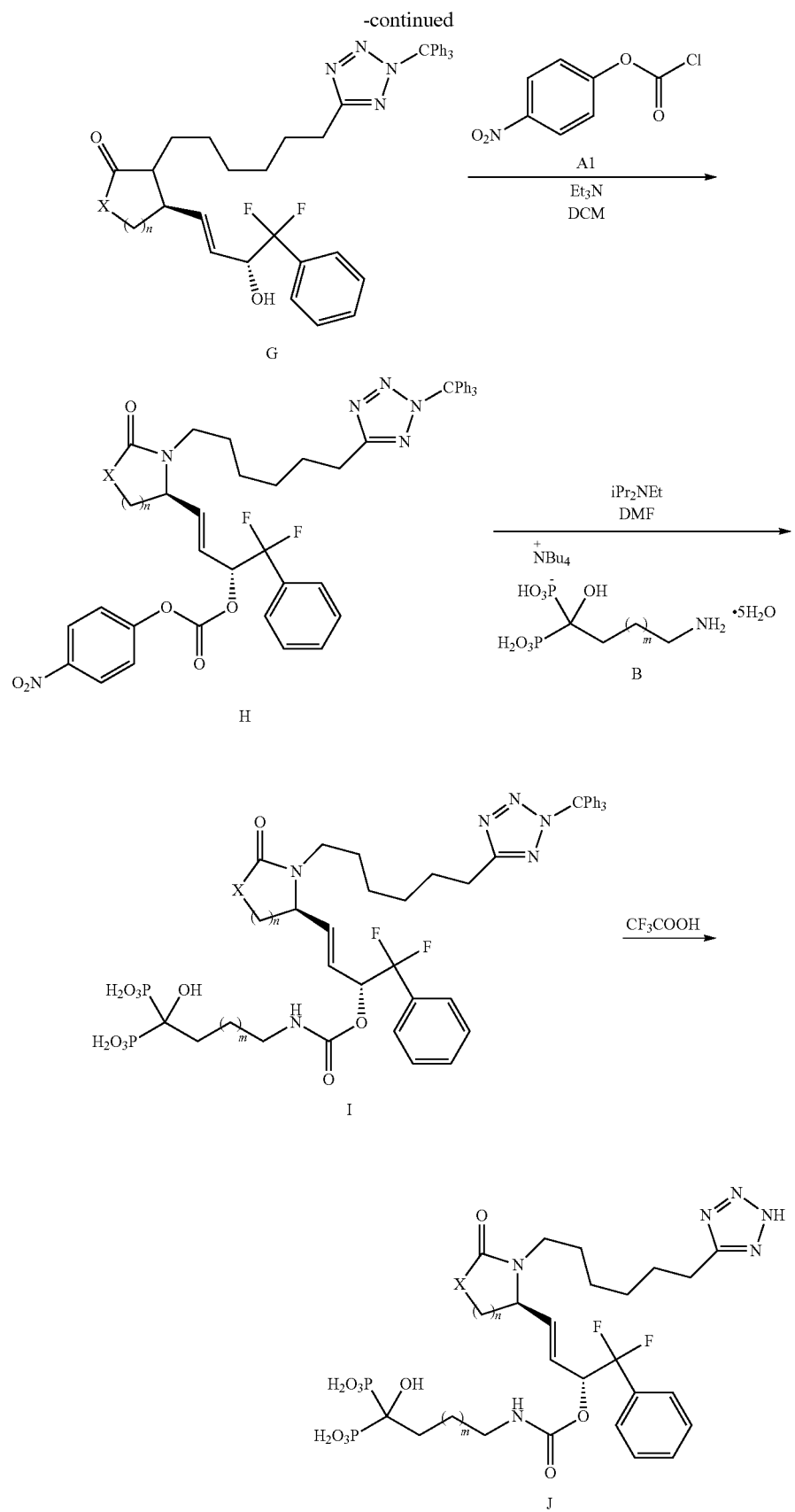

In Scheme IV, the EP4 agonist of general formula EP4c is reacted with trityl chloride to give G, which is reacted with A to give H and then with B to give I. Treatment of I with TFA then liberates J.

In this scheme, X may be C, NH, S or O; n may be 1, 2 or 3; m may be 1, 2, 3, 4, 5, or 6. It is to be understood that, for "m" the chain length is not critical to the synthesis and that any suitable chain length may be used.

A specific example of a conjugate compound prepared according to Scheme IV is as follows:

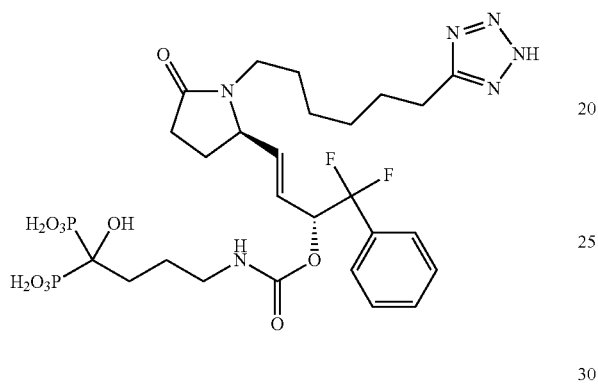

Compound 31

In alternative embodiments, other conjugates may be prepared as set forth in Scheme V.

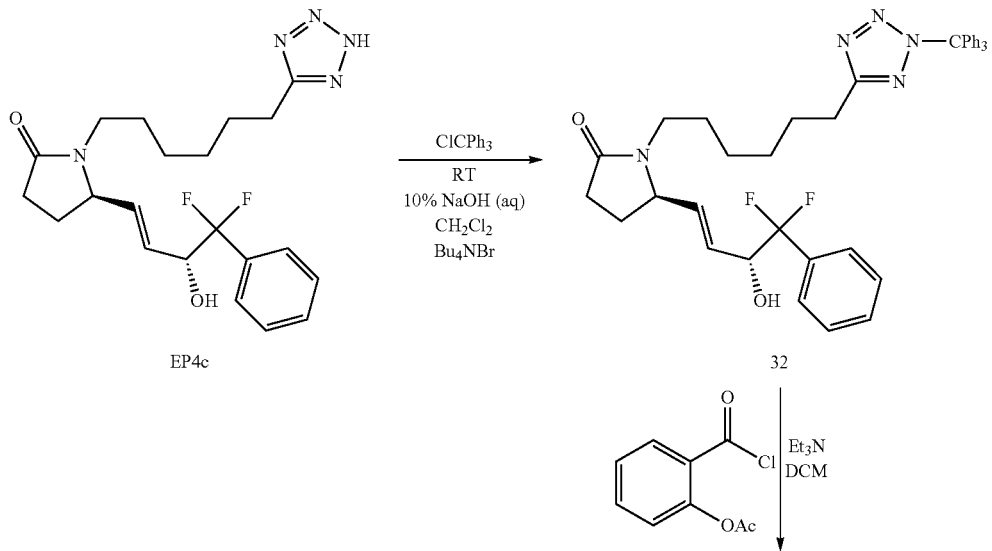

Scheme V

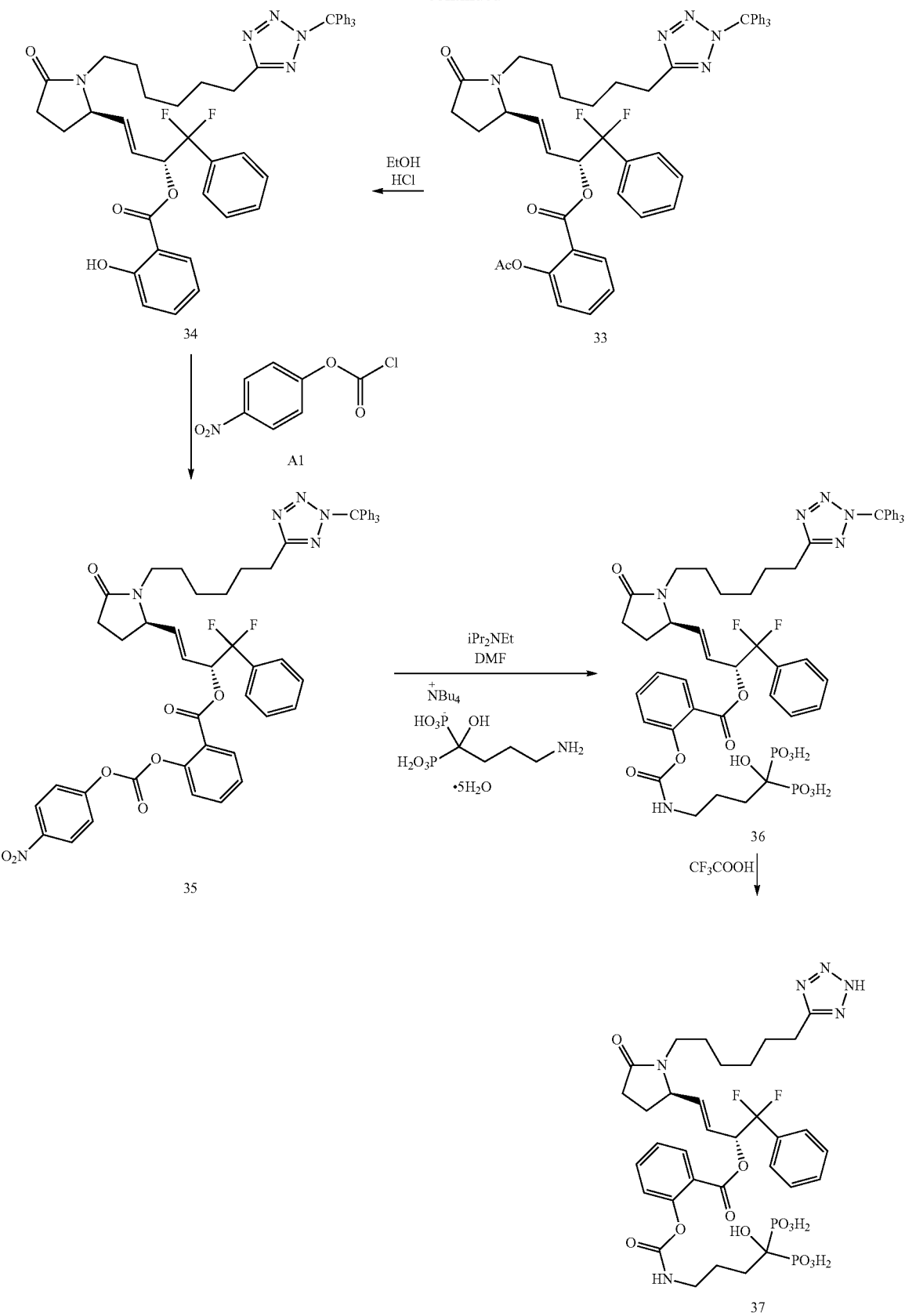

Examples of conjugates according to the invention include those set forth in Table II.
TABLE II
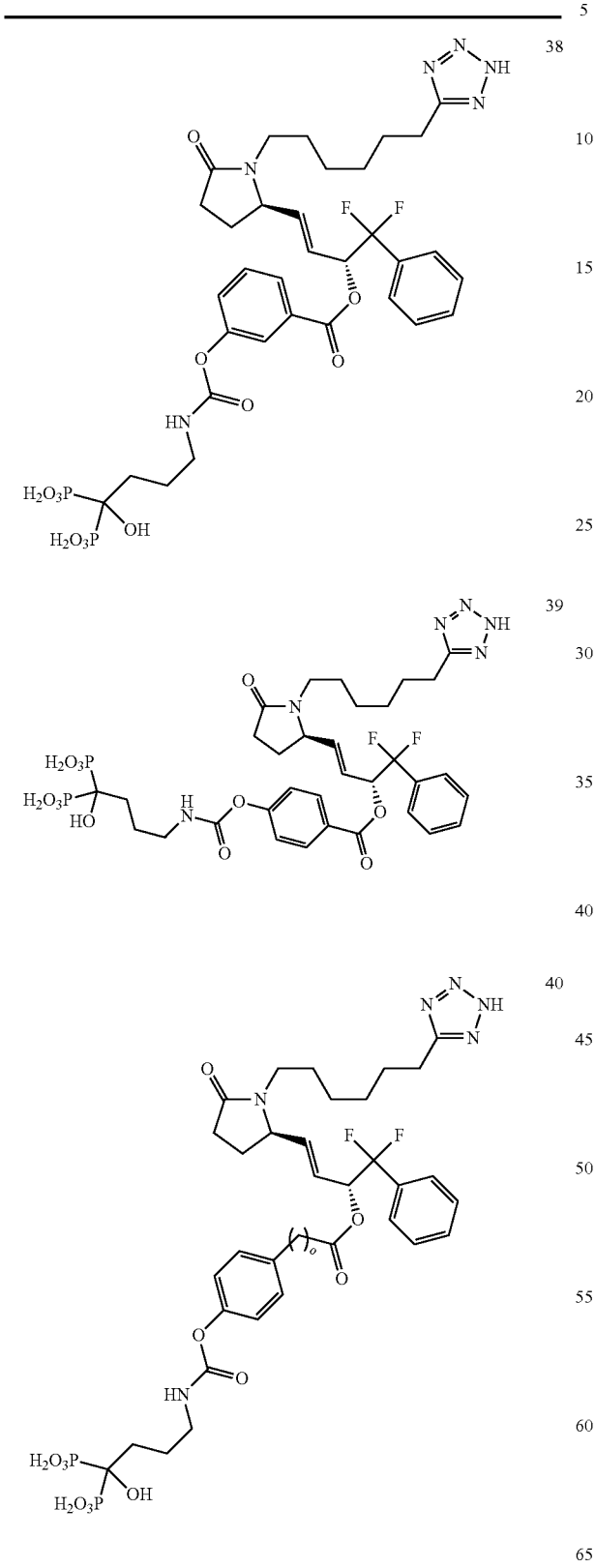
TABLE II-continued
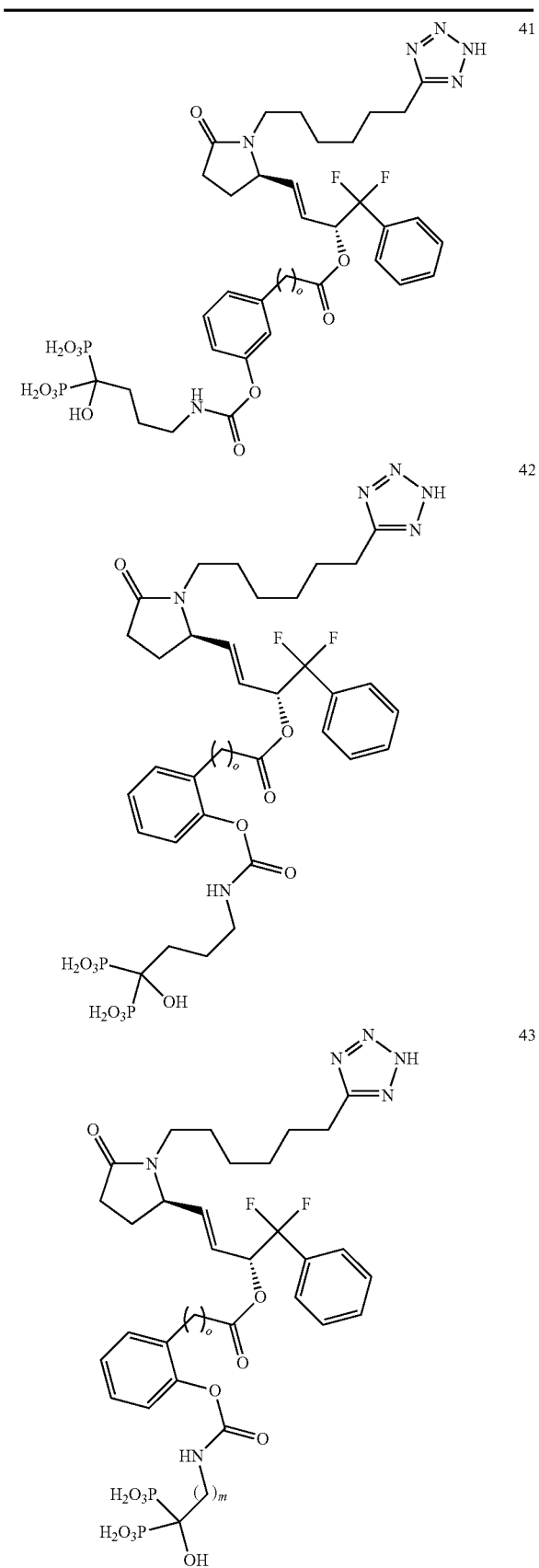

In Table II, m may be 1, 2, 3, 4, 5, or 6; o may be 0, 1, 2, 3, 4, 5, or 6.

In alternative embodiments, other conjugates may be prepared as set forth in Scheme VI.

Scheme VI

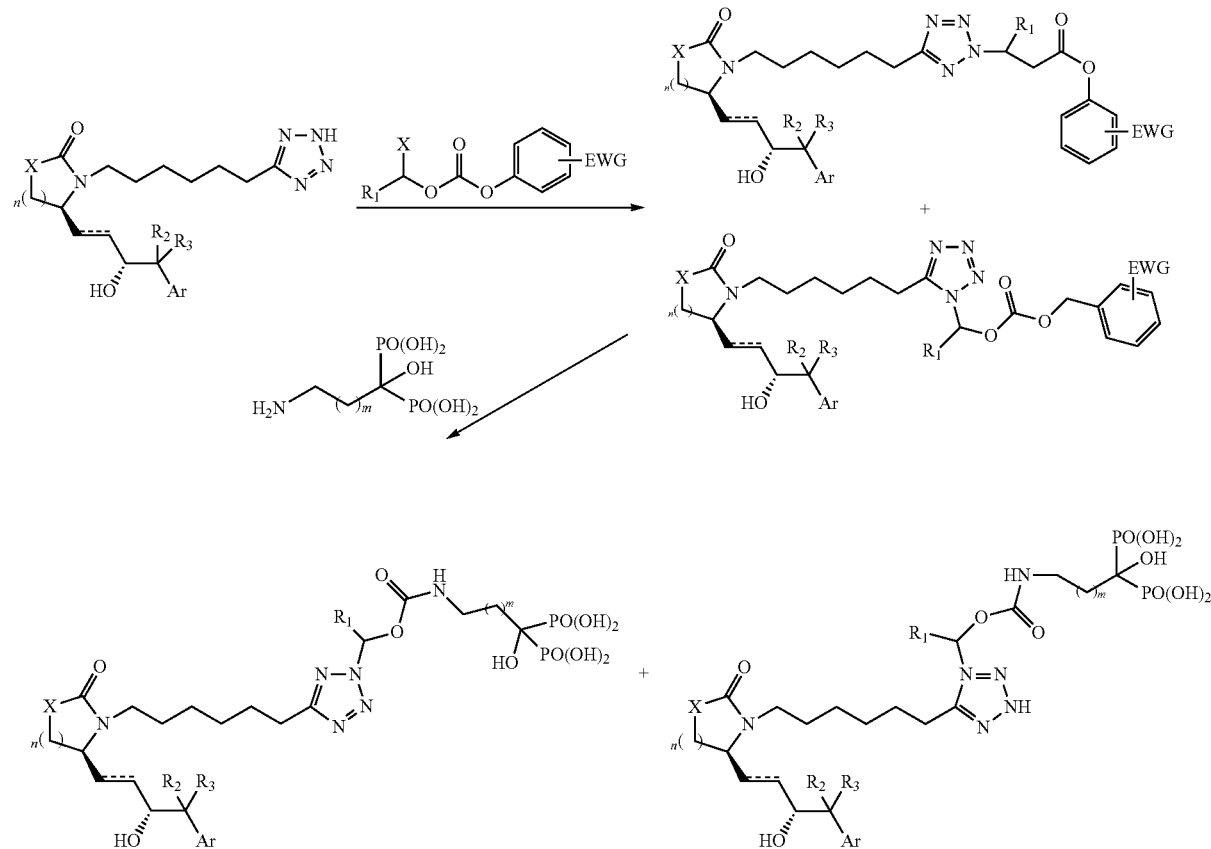

In this scheme, X may be C, NH, S or O; n may be 1, 2 or 3; m may be 1, 2, 3, 4, 5, or 6; $R_1$ may be lower alkyl or H; $R_2$ may be H or F; $R_3$ may be H or F. It is to be understood that, for "m" the chain length is not critical to the synthesis and that any suitable chain length may be used.

Further examples of conjugates according to the invention include those set forth in Table III.

TABLE III

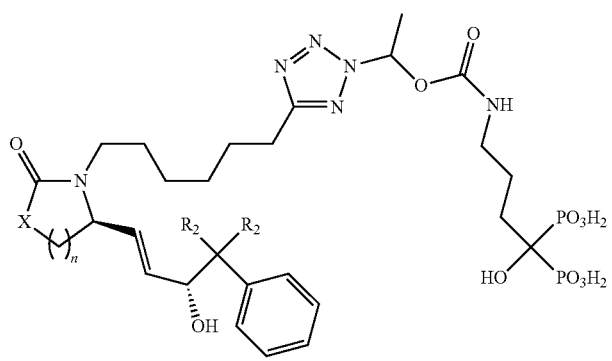

44

TABLE III-continued
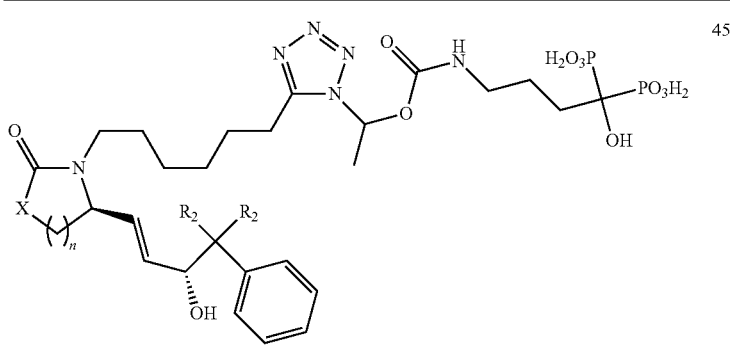
45
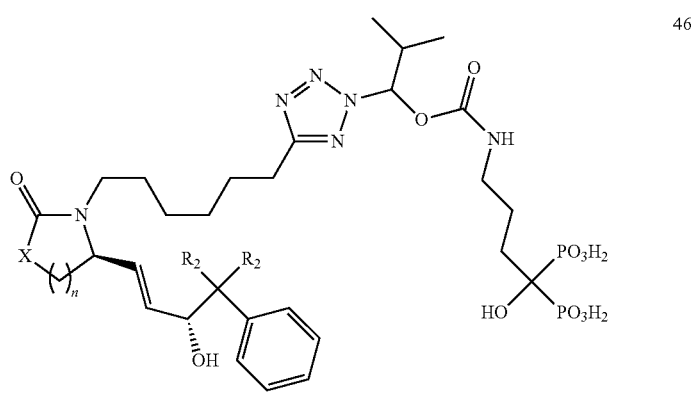
46
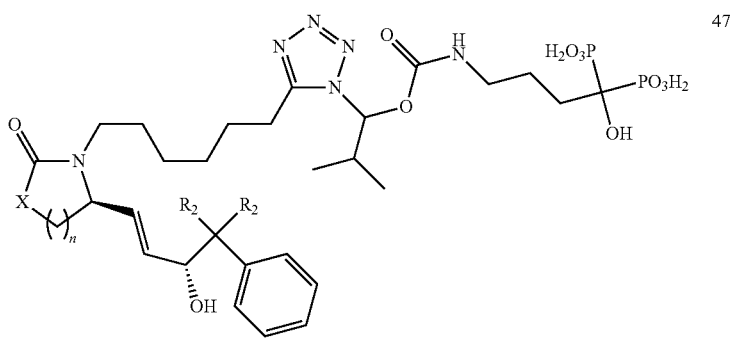
47
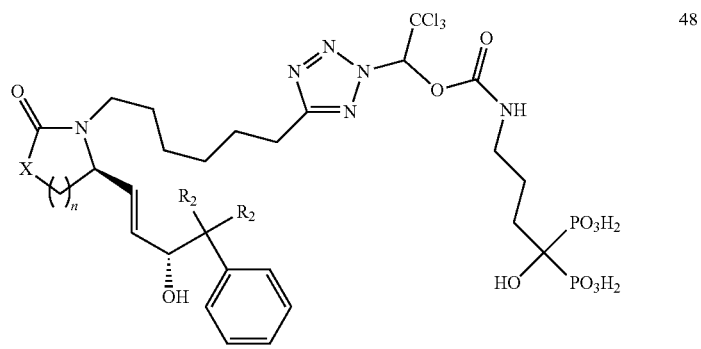
48

TABLE III-continued
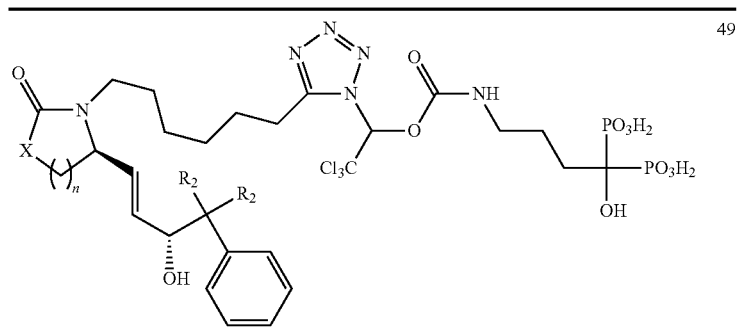
49
In Table III, X may be C, S, O, or NH; n may be 1, 2 or 3; R₂ may be independently H or halogen.
Further examples of conjugates according to the invention include those set forth in Table IV.
TABLE IV
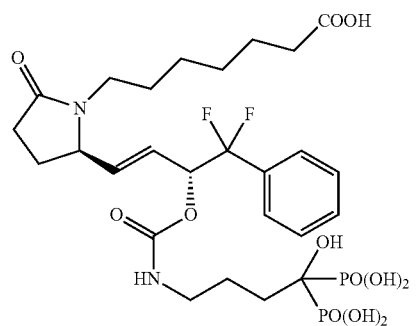
Compound 76
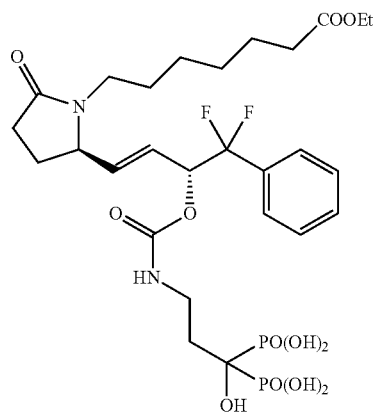
Compound 77
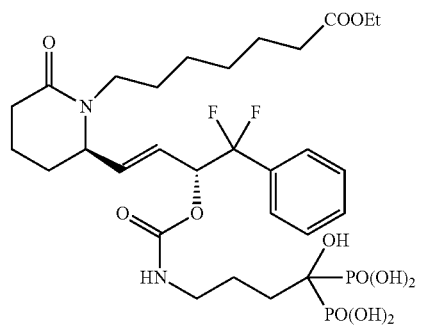
Compound 78

TABLE IV-continued
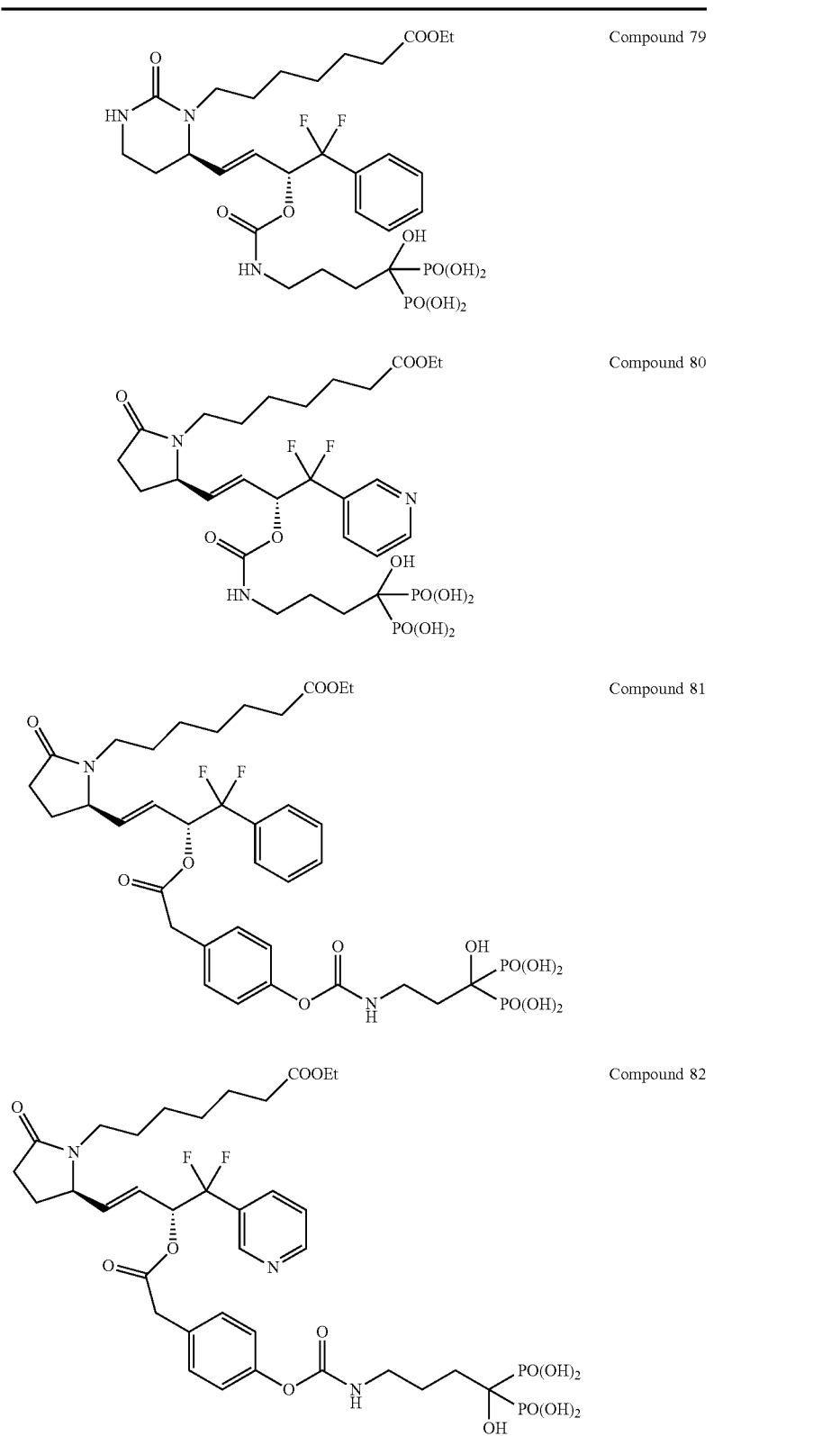
Compound 79
Compound 80
Compound 81
Compound 82

TABLE IV-continued

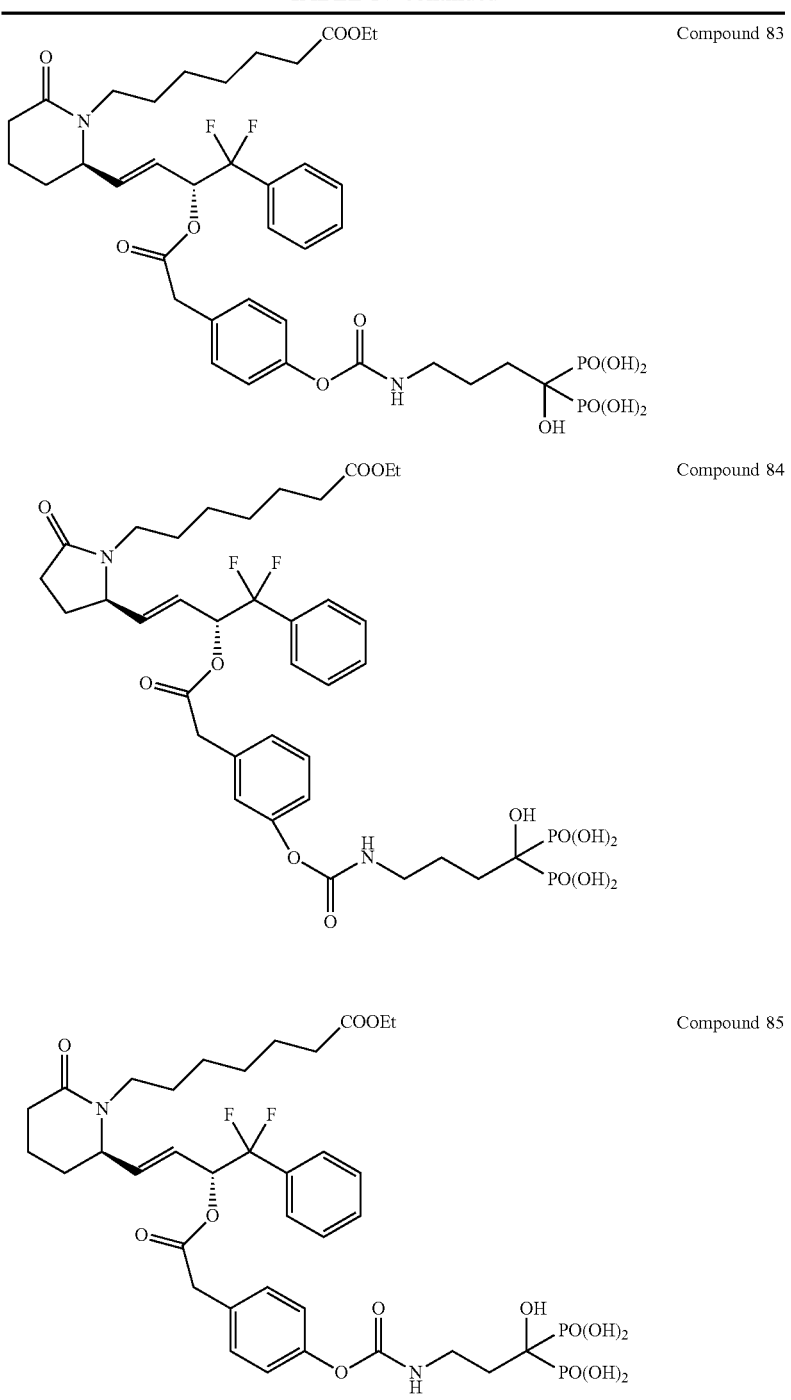

In alternative embodiments, Compounds 77 to 80 include the free carboxylic acid forms (i.e., COOH instead of COOEt). In general, Compounds 76 to 85 may be synthesized as described herein. For example, Compounds 76 to 80 may be synthesized as described herein with respect to Compound 8, or Compounds 81 to 85 may be synthesized as described herein with respect to Compound 56.

In alternative embodiments, intermediates for use in preparation of conjugates may be prepared as set forth in Scheme VII.

Scheme VII

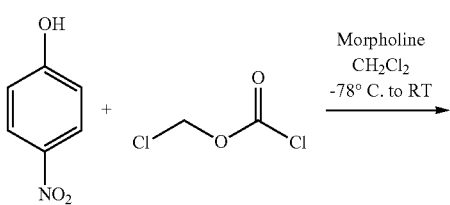

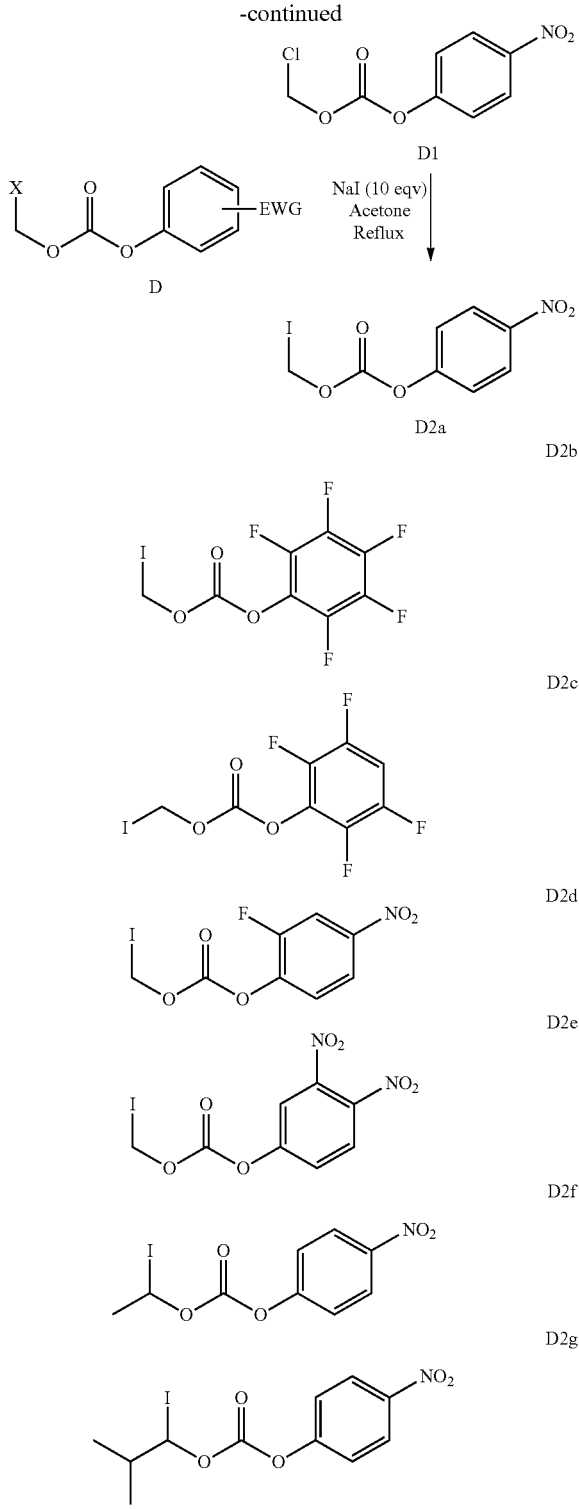

Compounds according to the invention include the conjugate compounds described herein, as well as intermediates used in the preparation of such compounds, together with derivatives, salts or stereoisomers thereof. In some embodiments, certain compounds (e.g., Compound 8) are specifically excluded from one or more of the compounds, compositions, methods or uses according to the invention.

In alternative aspects, the invention provides for conjugation of other agents containing a tetrazole, carboxylic acid or hydroxyl moiety to an amino-bisphosphonate. For example, pharmacologically active agents such as antineoplastic compounds may be conjugated to an amino-bisphosphonate.

Therapeutic Indications

A variety of conditions or disorders in humans and other mammals involve or are associated with abnormal or excessive bone loss, or with abnormal or reduced bone resorption, or with abnormal calcium metabolism. Such conditions or disorders include, but are not limited to, osteoporosis, which may include low bone mass and microarchitectural deterioration of bone tissue, with a consequent increase in bone fragility and susceptibility to fracture, glucocorticoid-induced osteoporosis, Paget's disease, abnormally increased bone turnover, bone graft, periodontal disease, alveolar bone loss, tooth loss, bone fractures, periprostheticosteolysis, osteogenesisimperfecta, metastatic bone disease, etc.

Accordingly, the conjugate compounds, as described herein, may be used to treat or prevent conditions or disorders associated with abnormal or excessive bone loss, or with abnormal or reduced bone resorption, or with abnormal calcium metabolism, or may be used to treat any condition or disorder that would benefit from targeting a therapeutic agent to the bone.

In alternative embodiments, the invention provides methods of enhancing or elevating levels of bone stimulation or inhibiting bone resorption in animal subjects, such as, veterinary and human subjects. This elevation or inhibition can be useful for the prevention or treatment of conditions or disorders associated with abnormal or excessive bone loss, or with abnormal or reduced bone resorption, or with abnormal calcium metabolism.

The effectiveness of the compounds in prevention or treatment of conditions or disorders associated with abnormal or excessive bone loss, or with abnormal or reduced bone resorption, or with abnormal calcium metabolism may be confirmed by testing the ability of the compounds to enhance or elevate bone stimulation or inhibit bone resorption using standard techniques.

For example, the conjugates may be evaluated first for in vitro for stability in plasma and then in normal animals (e.g., rats) for selective uptake into bones and slow release of the two components. When suitable conjugate(s) are identified, optimized compound(s) may be evaluated in animal models of osteoporosis or for example in an in vitro model of osteogenesis, i.e., neonatal rat calvaria cell cultures. Then the compounds may be used in for example in vivo or other assays to show efficacy and tolerability suitable for further development as novel therapies for treatment of disorders and conditions as described herein or found in the art.

In general, the methods of the invention are effected by administering a conjugate compound according to the invention to a subject in need thereof, or by contacting a cell or a sample with a compound according to the invention, for example, a pharmaceutical composition comprising a therapeutically effective amount of the compound.

Pharmaceutical & Veterinary Compositions, Dosages, and Administration

Pharmaceutical compositions including the conjugate compounds according to the invention, or for use according to the invention, are contemplated as being within the scope of the invention. In some embodiments, pharmaceutical compositions including an effective amount of a conjugate compound as described herein are provided.

In some embodiments, the conjugate compounds according to the invention target bone or a site at which bone growth stimulation or inhibition of bone resorption is required. Such a site includes both the area adjacent to a section of bone or group of bones in need of treatment in a subject in need thereof or a region inside the bone, including the site of a fracture or opening which occurs naturally or is intentionally made in the bone or group of bones. Bones in need of treatment may include green stick fractures, compound fractures, lateral fractures, pathologic fractures resulting from invasive tumors, compression fractures and fractures that require surgical procedures for realignment of bones.

The conjugate compounds and their pharmaceutically acceptable salts, stereoisomers, solvates, and derivatives are useful because they have pharmacological activity in animals, including humans. In some embodiments, the conjugate compounds according to the invention are stable in plasma, when administered to a subject.

In some embodiments, conjugate compounds according to the invention, or for use according to the invention, may be provided in combination with any other active agents or pharmaceutical compositions where such combined therapy is useful to treat or prevent conditions or disorders associated with abnormal or excessive bone loss, or with abnormal or reduced bone resorption, or with abnormal calcium metabolism, for example, to treat any condition or disorder described herein or that would benefit from targeting a therapeutic agent to the bone.

In some embodiments, conjugate compounds according to the invention, or for use according to the invention, may be provided in combination with one or more agents useful in the prevention or treatment of conditions or disorders associated with abnormal or excessive bone loss, or with abnormal or reduced bone resorption, or with abnormal calcium metabolism to treat any condition or disorder described herein or that would benefit from targeting a therapeutic agent to the bone.

Combinations of conjugate compounds according to the invention, or for use according to the invention, and other therapies useful in the prevention or treatment of conditions or disorders associated with abnormal or excessive bone loss, abnormal or reduced bone resorption, abnormal calcium metabolism, cancer, or any disorder associated with bone or that would benefit from targeting a therapeutic agent to the bone, may be administered separately or in conjunction. The administration of one agent or conjugate compound may be prior to, concurrent to, or subsequent to the administration of other agent(s) or conjugate compounds.

In alternative embodiments, while the conjugate compounds according to the invention may themselves be considered "prodrugs," the conjugate compounds may be supplied as further prodrug or protected forms, which release the compound after administration to a subject. For example, the compound may carry a protective group which is split off by hydrolysis in body fluids, e.g., in the bloodstream, thus releasing the active compound or is oxidized or reduced in body fluids to release the compound. Accordingly, a "prodrug" is meant to indicate a compound that may be converted under physiological conditions (e.g., enzymatically) or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a subject.

The term "prodrug" is also meant to include any covalently bonded carriers which release the active compound of the invention in vivo when such prodrug is administered to a subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and acetamide, formamide, and benzamide derivatives of amine functional groups in the compounds of the invention and the like.

A discussion of prodrugs may be found in "Smith and Williams' Introduction to the Principles of Drug Design," H. J. Smith, Wright, Second Edition, London (1988); Bundgard, H., *Design of Prodrugs* (1985), pp. 7-9, 21-24 (Elsevier, Amsterdam); The Practice of Medicinal Chemistry, Camille G. Wermuth et al., Ch 31, (Academic Press, 1996); A Textbook of Drug Design and Development, P. Krogsgaard-Larson and H. Bundgaard, eds. Ch 5, pgs 113 191 (Harwood Academic Publishers, 1991); Higuchi, T., et al., "Pro-drugs as Novel Delivery Systems," A.C.S. Symposium Series, Vol. 14; or in Bioreversible Carriers in Drug Design, ed. Edward B. Roche, American Pharmaceutical Association and Pergamon Press, 1987, all of which are incorporated in full by reference herein.

Suitable prodrug forms of the compounds of the invention include embodiments in which one of the hydroxyl groups is substituted with C(O)OR, where R is optionally substituted alkyl, alkenyl, alkynyl, aryl, or heteroaryl. In these cases the ester groups may be hydrolyzed in vivo (e.g. in bodily fluids), releasing the active compounds.

Conjugate compounds according to the invention, or for use according to the invention, can be provided alone or in combination with other compounds in the presence of a liposome, an adjuvant, or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. Compounds according to the invention may be provided chronically or intermittently. "Chronic" administration refers to administration of the compound(s) in a continuous mode as opposed to an acute mode, so as to maintain the initial therapeutic effect (activity) for an extended period of time. "Intermittent" administration is treatment that is not consecutively done without interruption, but rather is cyclic in nature. The terms "administration," "administrable," or "administering" as used herein should be understood to mean providing a compound of the invention to the subject in need of treatment.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved, for example, by the United States Food and Drug Administration or other governmental agency as being acceptable for use in humans or domestic animals.

The compounds of the present invention may be administered in the form of pharmaceutically acceptable salts. In such cases, pharmaceutical compositions in accordance with this invention may comprise a salt of such a compound, preferably a physiologically acceptable salt, which are known in the art. In some embodiments, the term "pharmaceutically acceptable salt" as used herein means an active ingredient comprising conjugate compounds used in the form of a salt thereof, particularly where the salt form confers on the active ingredient improved pharmacokinetic properties as compared to the free form of the active ingredient or other previously disclosed salt form.

A "pharmaceutically acceptable salt" includes both acid and base addition salts. A "pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

A "pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Thus, the term "pharmaceutically acceptable salt" encompasses all acceptable salts including but not limited to acetate, lactobionate, benzenesulfonate, laurate, benzoate, malate, bicarbonate, maleate, bisulfate, mandelate, bitartarate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of the compounds of the present invention can be used as a dosage for modifying solubility or hydrolysis characteristics, or can be used in sustained release or prodrug formulations. Also, pharmaceutically acceptable salts of the compounds of this invention may include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

Pharmaceutical formulations will typically include one or more carriers acceptable for the mode of administration of the preparation, be it by injection, inhalation, topical administration, lavage, or other modes suitable for the selected treatment. Suitable carriers are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in *Remington: the Science & Practice of Pharmacy* by Alfonso Gennaro, $20^{th}$ ed., Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The conjugate compounds or pharmaceutical compositions according to the present invention may be administered by oral or non-oral, e.g., intramuscular, intraperitoneal, intravenous, intracisternal injection or infusion, subcutaneous injection, transdermal or transmucosal routes. In some embodiments, conjugate compounds or pharmaceutical compositions in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the conjugate compound, or its individual components, over a period of time. The conjugate compounds may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaries. In some embodiments, conjugate compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The conjugate compounds of the invention may be used to treat animals, including mice, rats, horses, cattle, sheep, dogs, cats, and monkeys. However, compounds of the invention can also be used in other organisms, such as avian species (e.g., chickens). The compounds of the invention may also be effective for use in humans. The term "subject" or alternatively referred to herein as "patient" is intended to be referred to an animal, preferably a mammal, most preferably a human, who has been the object of treatment, observation or experiment. However, the conjugate compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition or disorder associated with abnormal or excessive bone loss, or with abnormal or reduced bone resorption, or with abnormal calcium metabolism, a cancer, a disorder associated with bone, or a disorder that would benefit from targeting a therapeutic agent to the bone.

An "effective amount" of a compound according to the invention includes a therapeutically effective amount or a prophylactically effective amount. A "therapeutically effective amount" refers to an amount effective, at dosages and for periods of time necessary, to achieve the desired therapeutic result, such as inhibition of bone resorption, stimulation of bone growth, or treatment of any condition described herein. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as inhibition of bone resorption, stimulation of bone growth, or prevention of any condition described herein. Typically, a prophylactic dose is used in subjects prior to or at an earlier stage of disease, so that a prophylactically effective amount may be less than a therapeutically effective amount. A suitable range for therapeutically or prophylactically effective amounts of a compound may be any value from 0.1 nM-0.1M, 0.1 nM-0.05M, 0.05 nM-15 µM or 0.01 nM-10 µM.

In alternative embodiments, in the treatment or prevention of conditions which require modulation of bone growth or resorption or calcium metabolism, an appropriate dosage level will generally be about 0.01 to 1000 mg per kg subject body weight per day, and can be administered in singe or multiple doses. In some embodiments, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. In general, compounds of the invention should be used without causing substantial toxicity, and as described herein, the compounds exhibit a suitable safety profile for therapeutic use. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

In some embodiments, the conjugate compounds according to the invention are hydrolyzed at a rate that allows for dosage once a week.

Various alternative embodiments and examples of the invention are described herein. These embodiments and examples are illustrative and should not be construed as limiting the scope of the invention.

The present invention will be further illustrated in the following examples.

EXAMPLE 1

Model Coupling of Benzyltetrazole with Benzylamine

We initially undertook model experiments using commercially available benzyltetrazole 25 as shown in Scheme 1.

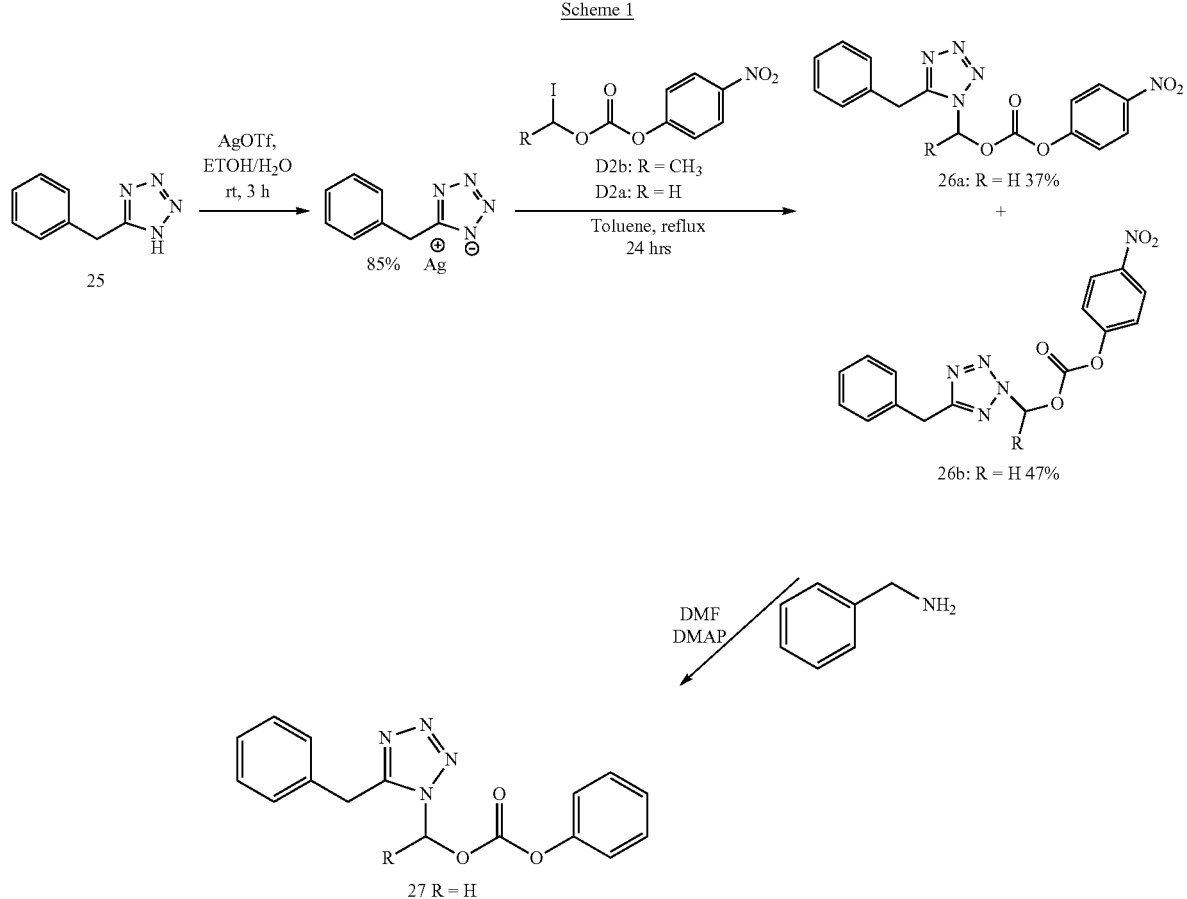

These studies showed that benzyltetrazole mercury salt could be reacted chloromethyloxy-carbonyloxy-p-nitrobenzene (D2a) to provide the intermediates 26a and 26b in poor to moderate yield which then could be reacted with a model amine (benzylamine) in dimethylformamide (DMF) to provide a model conjugate 27 (Scheme 1). Initially some issues were faced as it was difficult to reliably prepare the mercury salt of 25 using the literature methods of reaction with mercuric oxide. The salt formation was capricious and yields were not reproducible. We then turned to the use of the silver salt of the tetrazole instead and found that reaction of benzyltetrazole with silver triflate with iodomethyloxycarbonyloxy-p-nitrobenzene (D2a) gave the desired intermediates 26a and 26b in good yields and then reaction with benzylamine in DMF gave the model conjugates (27) in acceptable yields. 26a and 26b could be separated by chromatography if so desired.

EXAMPLE 2

Model Coupling of Benzyltetrazole with Alendronate

The next issue was to demonstrate we could react 26a and/or 26b with alendronic acid (3) in a similar manner. The poor solubility of 3 in anything other than water presented a challenge. The reagents could be mixed in aqueous DMF but liberation of the amino group in 3 (necessary for coupling) required fairly high pH and competing hydrolysis of 26a led to failure of the reaction. This problem was solved by our novel observation that alendronic acid can be readily converted to it's mono-tetrabutylamonium salt (3a) by reaction with tetrabutylammonium hydroxide in water followed by lyophylization to provide the salt as a hydrate. 3a was found to be freely soluble in anhydrous DMF and a variety of other solvents such as dioxane, ethanol and even dichloromethane, allowing for more careful control of the coupling reaction. Thus 3a reacted smoothly with 26a in anhydrous DMF in the presence of 4-5 equivalents of a non-nucleophilic base, di-isopropylethylamine to provide the desired model conjugate 16 in excellent yield (Scheme 2).

Scheme 2

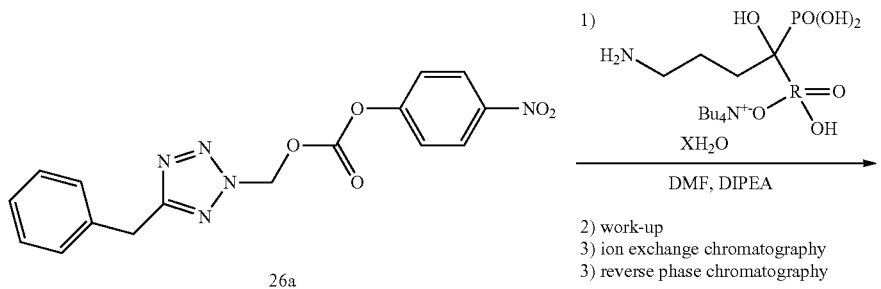

26a 2) work-up
3) ion exchange chromatography
3) reverse phase chromatography

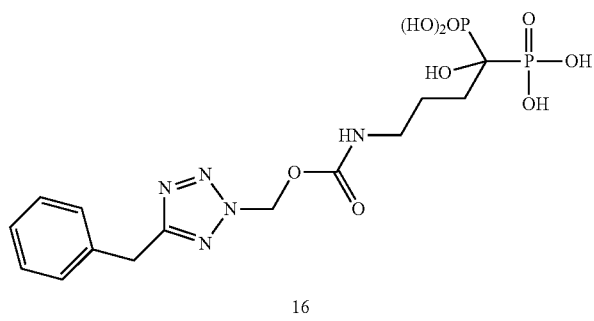

16

The facile solubility of 3a in anhydrous solvents allows for simple direct N-substitution with a variety of reactive electrophiles usually incompatible with water and we were able to demonstrate reaction with a large variety of electophiles such as benzoic anhydride, benzyloxychloroformate and cinnamoyl-oxycarbonyl-oxy-p-nitrophenylbenzene in DMF or dichloromethane to provide the derivatives 28, 29 and 30 in excellent yields (Scheme 3: Acylation of alendronate tetra n-butylammonium salt).

Scheme 3

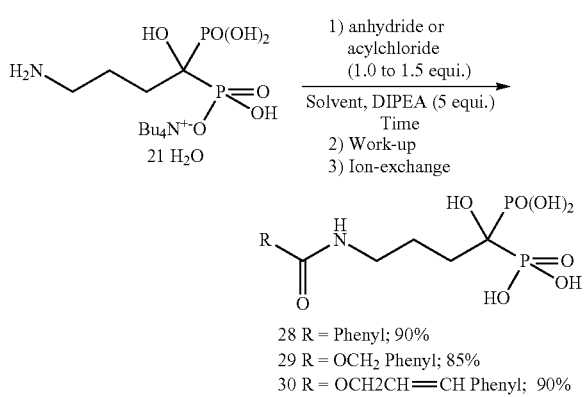

28 R = Phenyl; 90%
29 R = OCH₂ Phenyl; 85%
30 R = OCH2CH═CH Phenyl; 90%

EXAMPLE 3

Preparation of Conjugates 6 and 7

EP4 receptor agonist tetrazole 1 was reacted with silver triflate and then with D2a to provide the intermediates 22 and 23 in reasonable yields. We subsequently found that the mercury salt of 1 (formed by exchange with mercuric acetate) reacted to provide 22 and 23 in reproducible and excellent yield. 22 and/or 23 were then reacted with 3a in DMF to provide the target conjugates 6 and 7 as tetra-n-butylammonium salts. The conjugates were purified by ion exchange (to exchange the tetra-n-butylammonium ion for a proton) and thence by reverse phase chromatography to give 6 and 7 in excellent yields (Scheme 4). The conjugates 6 and 7 required synthesis of activated intermediates (such as 22 and 23) followed by reaction with alendronic acid (3). No such compounds were known in the literature and the reaction of intermediates such as 22 or 23 with 3a was considered to be particularly challenging due to the poor solubility of alendronic acid (3) in any solvent other than water. Thus, while it is possible to use alendronic acid (3) in the conjugation reaction, compound 3a yielded better results.

Scheme 4: Preparation of conjugates 6 and 7
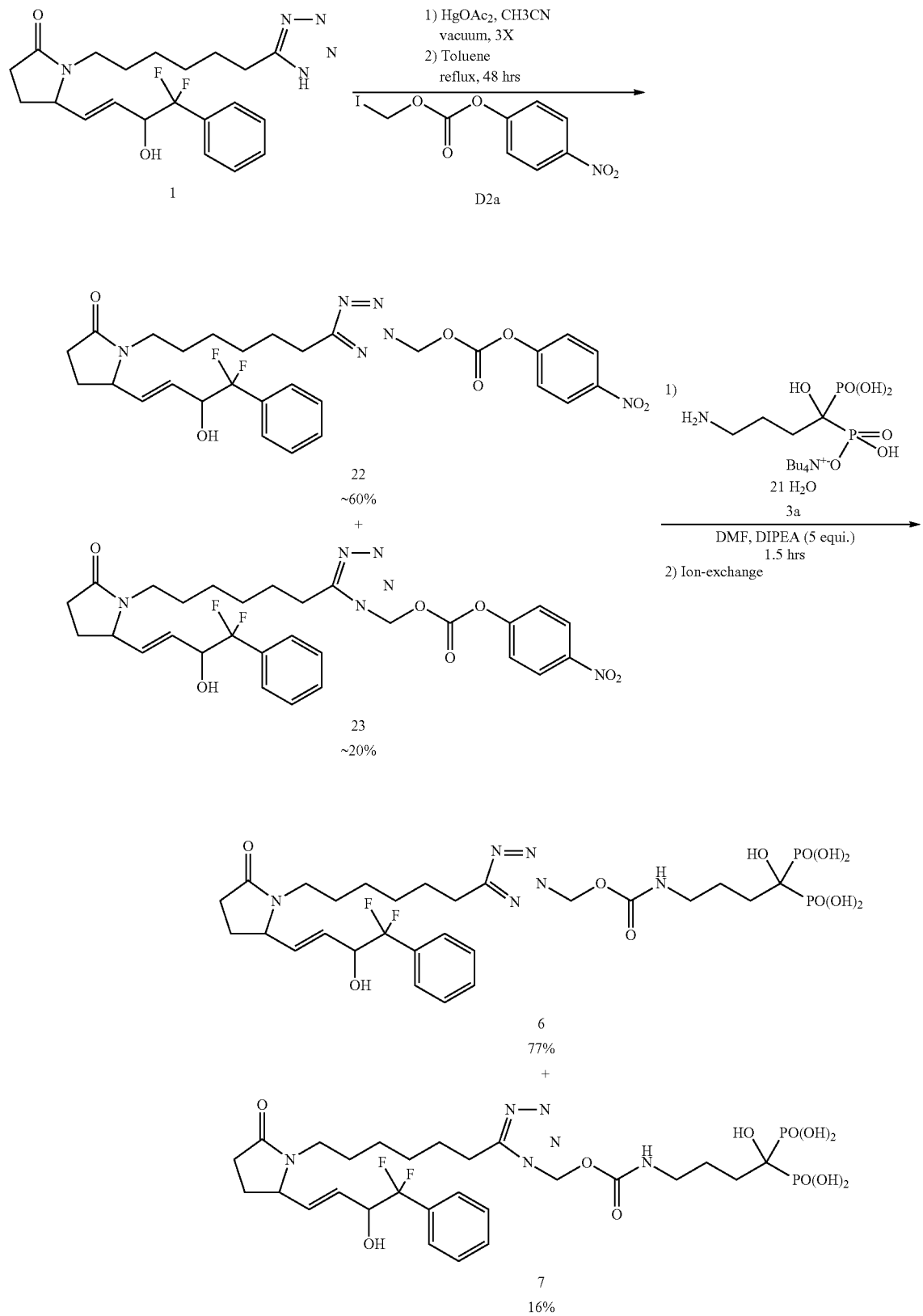

More specifically, the synthesis steps were as follows.
Preparation of Compound 1:

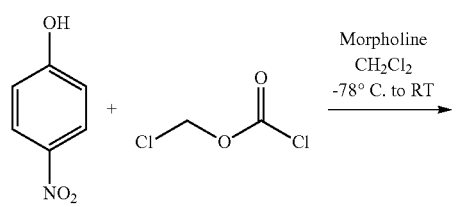

Activities in Breast and Prostate Cancer Cells in Vitro" *J. Med. Chem.* 2008, 51, 3895-3904). 1H NMR (CDCl$_3$): δ 5.85 (s, 2H), 7.43 (d, 2H), 8.31 (d, 2H).

Preparation of Compound 2:

p-Nitrophenol (1.15 g, 8.29 mmol, 1 equivalent)) was dissolved in 20 mL of CH$_2$Cl$_2$ under argon followed by addition of (0.91 mL, 8.29 mmol, 1 equivalent) of morpholine. The reaction mixture was cooled to −78° C. and ClCH$_2$OCOCl (0.74 mL, 8.29 mmol, 1 equivalent) added. The reaction was left to stir overnight. Solvent was removed by rotary evaporator and extraction performed with ethyl acetate and water. The organic layer was collected and dried over Na$_2$SO$_4$. The product D1 was isolated by flash column chromatography (Gediya, Lalji K.; Khandelwal, Aakanksha; Patel, Jyoti; Belosay, Aashvini; Sabnis, Gauri; Mehta, Jhalak; Purushottamachar, Puranik; Njar, Vincent C. O. "Design, Synthesis, and Evaluation of Novel Mutual Prodrugs (Hybrid Drugs) of All-trans-Retinoic Acid and HistoneDeacetylase Inhibitors with Enhanced Anticancer Compound D1 (1 equivalent) and NaI (10 equivalents) was taken in a flask under argon. 40 mL acetone was added to it and left to stir under refluxing condition for 24 hrs. The reaction mixture was washed with water and the organic layer collected. A gradient silica column with hexanes and ethyl acetate gave compound D2a (Gediya, Lalji K.; Khandelwal, Aakanksha; Patel, Jyoti; Belosay, Aashvini; Sabnis, Gauri; Mehta, Jhalak; Purushottamachar, Puranik; Njar, Vincent C. O. "Design, Synthesis, and Evaluation of Novel Mutual Prodrugs (Hybrid Drugs) of All-trans-Retinoic Acid and HistoneDeacetylase Inhibitors with Enhanced Anticancer Activities in Breast and Prostate Cancer Cells in Vitro" *J. Med. Chem.* 2008, 51, 3895-3904). 1H NMR: δ 6.07 (s, 2H), 7.43 (d, 2H), 8.31 (d, 2H).

Preparation of Compound 6 and 7:

Scheme 7

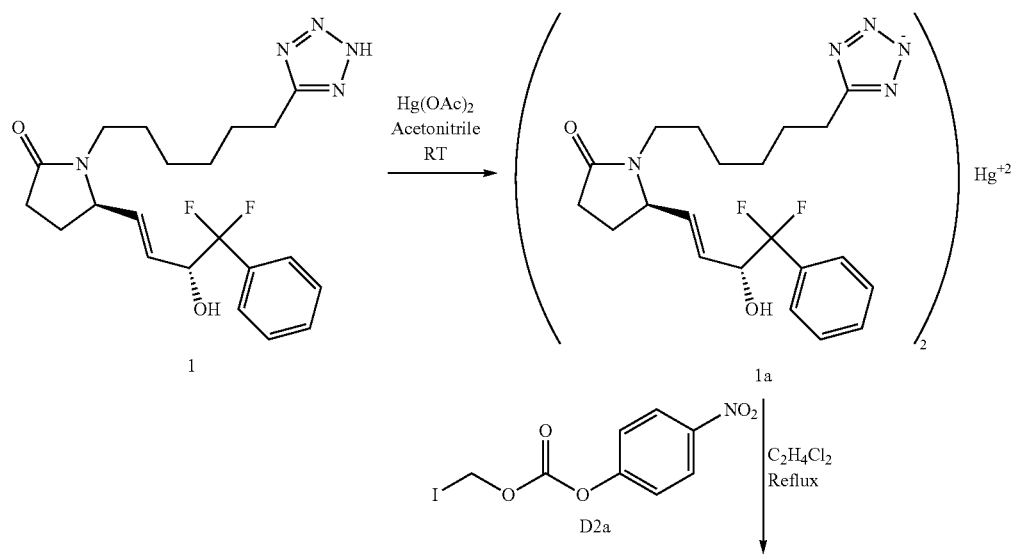

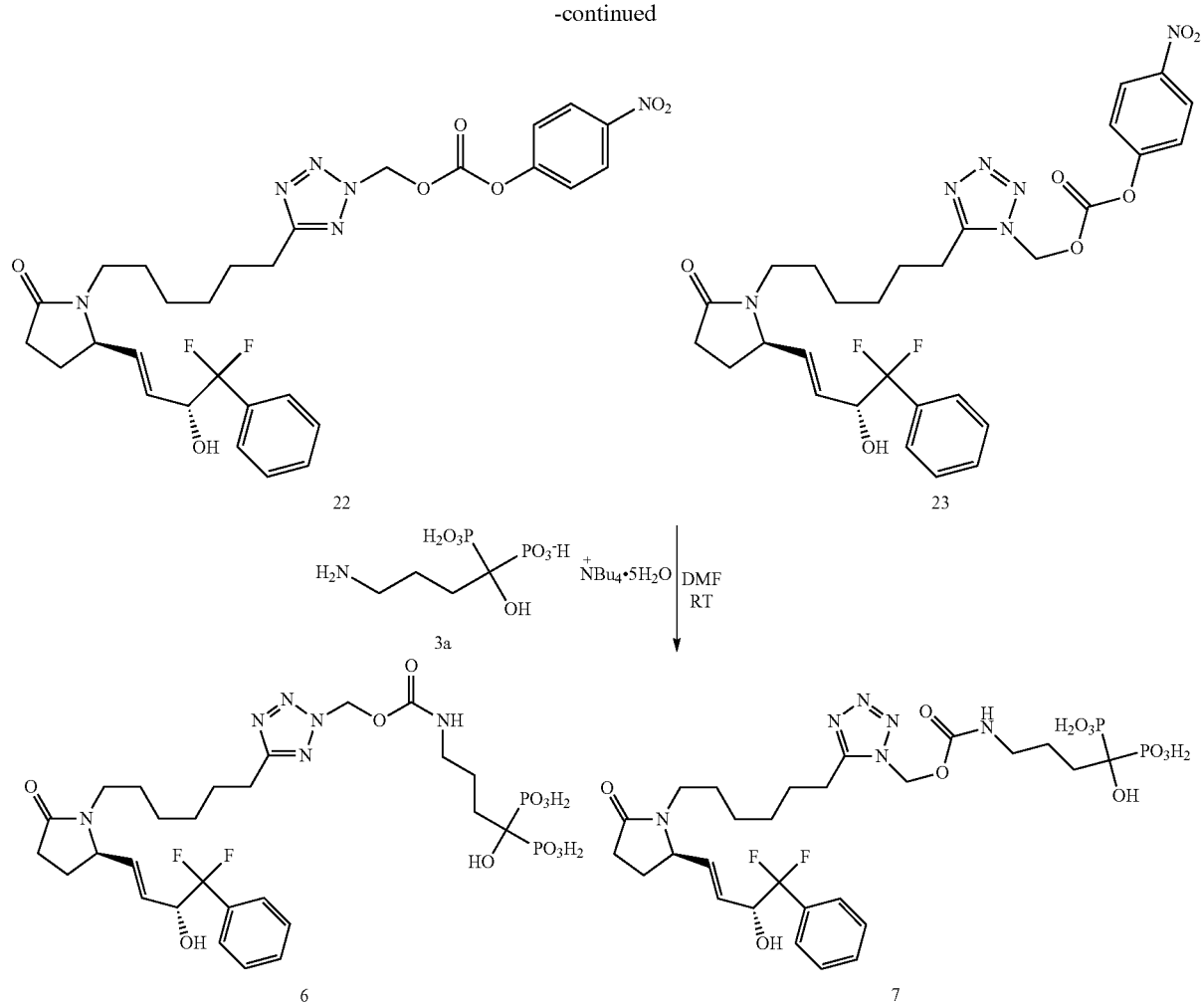

Compound 1 (1 equivalent) and Hg(OAc)$_2$ (0.5 equivalents) was taken in a flask under argon atmosphere, followed by addition of 10 mL CH$_3$CN. This was stirred for 2 hrs. Solvent was removed by vacuum. Left under vacuum for 3 hrs. Then added another 10 mL of CH$_3$CN to the mixture. Left to stir for 4 hrs; then removed the solvent by vacuum and left under vacuum overnight. Added compound 3a (1 equivalent) and solvent C$_2$H$_4$Cl$_2$ under argon to the reaction mixture and refluxed for 24 hrs. Removed solvent using rotary-evaporator. Compound 22 and 23 was isolated by gradient column chromatography of hexanes and ethyl acetate on silica. 22 1H NMR (CDCl$_3$): δ 8.28-8.31 (d, 2H), 7.43-7.48 (m, 5H), 7.38-7.43 (d, 2H), 6.56 (s, 2H), 5.65-5.71 (m, 2H), 4.51-4.62 (m, 1H), 4.00-4.06 (m, 1H), 3.35-3.44 (m, 1H), 2.90-2.97 (t, 2H), 2.70-2.76 (m, 1H), 2.64 (s, 1H), 2.25-2.40 (m, 2H), 2.16-2.21 (m, 1H), 1.76-1.84 (m, 2H), 1.57-1.68 (m, 2H), 1.35-1.45 (m, 5H), 1.15-1.32 (m, 7H). 13C NMR (CDCl$_3$): δ 174.8, 168.2, 154.8, 151.0, 145.8, 135.2, 130.3, 125.4, 121.6, 74.2, 60.1, 40.5, 29.9, 29.7, 28.5, 27.5, 27.0, 26.2, 25.4, 25.2, 23 1H NMR (CDCl$_3$): δ 8.27-8.31 (d, 2H), 7.4-7.5 (m, 5H), 7.35-7.38 (d, 2H), 6.35 (s, 2H), 5.60-5.75 (m, 2H), 4.53-4.62 (m, 1H), 4.00-4.05 (m, 1H), 2.96-3.00 (t, 2H), 2.75-2.85 (m, 2H), 2.25-2.40 (m, 3H), 2.15-2.24 (m, 1H), 1.83-1.90 (m, 2H), 1.58-1.70 (m, 2H), 1.35-1.50 (m, 5H), 1.15-1.35 (m, 7H). 13C NMR (CDCl$_3$): δ 175.1, 156.3, 154.6, 151.2, 145.9, 135.0, 125.9, 125.5, 121.6, 69.8, 60.3, 40.4, 30.0, 29.7, 28.3, 26.8, 26.6, 26.0, 25.4, 22.8.

Preparation of Compound 6:

Under argon atmosphere taken compound 22 (1 equivalent) and compound 3a (1.1 equivalent) in a flask, and added 1 mL of dimethylformamide (DMF) as a solvent. Then added diisopropylethylamine (5 equivalent) and left to stir at room temperature for 24 hrs. Then removed DMF by rotary evaporator. Dissolved the residual mixture in water (10 mL) and CH$_2$Cl$_2$ (10 mL). Collected product 6 in the water layer and discarded the organic layer. Washed the water layer 7 more times with 10 mL amount CH$_2$Cl$_2$. Removed water under vacuum. Then performed an ion-exchange (Amberlite ion exchange resin, H$^+$ form) separation using milli-Q water. Removed water under vacuum. The product was further purified by a C-18 sep-pack using water and methanol gradient solvent system. 6 1H NMR (CDCl$_3$): δ 7.40-7.55 (m, 5H), 6.42 (s, 2H), 5.55-5.75 (m, 2H), 4.62-4.73 (m, 1H), 4.15-4.23 (m, 1H), 3.13-3.21 (m, 1H), 3.09-3.13 (t, 1H), 2.90-2.95 (t, 2H), 2.48-2.56 (m, 1H), 2.34-2.40 (t, 2H), 2.15-2.25 (m, 1H), 1.86-1.98 (m, 2H), 1.63-1.85 (m, 5H), 1.11-1.35 (m, 7H). 13C NMR (CDCl$_3$): δ 178.0, 171.0, 167.5, 155.6, 136.1, 130.6, 127.6, 125.6, 74.2, 74.0, 73.8, 73.7, 72.4, 60.9, 41.2, 40.6, 30.8, 30.0, 27.4, 26.6, 25.9, 25.3, 24.4, 24.2, 23.7, 23.6. HRMS calcd 725.2271 ($C_{27}H_{40}F_2N_6O_{11}P_2H^+$). found 725.2293.

Compound 7 was prepared similarly. 1H NMR (CDCl$_3$): δ 7.40-7.55 (m, 5H), 6.26 (s, 2H), 5.55-5.75 (m, 2H), 4.62-4.73 (m, 1H), 4.15-4.23 (m, 1H), 3.15-3.25 (m, 1H), 3.08-3.14 (t, 2H), 3.03-3.08 (t, 2H), 2.53-2.63 (m, 1H), 2.34-2.42 (t, 2H), 2.15-2.27 (m, 1H), 1.85-1.97 (m, 2H), 1.75-1.85 (m, 3H), 1.65-1.74 (m, 1H), 1.25-1.39 (m, 4H), 1.15-1.25 (m, 2H). HRMS calcd 747.2091 ($C_{27}H_{40}F_2N_6O_{11}P_2Na^+$). found 747.2128.

EXAMPLE 4

Stability of Conjugates 6 and 7

The stability of the conjugates 6 and 7 were evaluated both chemically and in vitro in rat plasma. As the bone in vivo efficacy studies will be done in rats it was desirable to determine if the compounds are sufficiently stable to survive in the blood stream long enough to be taken up into bone via binding of the 1-hydroxy-1,1-bisphosphonate moiety. Treatment of 6 with 1N NaOH led to complete hydrolysis and liberation of 1 (and also 3) within 10 minutes. A mixture of 6 and 7 were incubated in fresh rat plasma at 37° C. and the stability of the conjugate was monitored by appearance of 1 by LC/MS/MS. The conjugate was quite stable but smooth but slow liberation of 1 was observed over 96 hours (see FIG. 1).

EXAMPLE 5

Preparation and Evaluation of Conjugate 8

Preparation of the conjugate 8 required the synthesis of the EP4-selective agonist 2. This 11 step synthesis was carried out on large scale starting from (+)-D-pyroglutamic acid to provide 2 and its ethyl ester (2a) (about 2 gm combined total). The synthesis was carried out largely as described in the literature (Y. Han et al. U.S. Pat. No. 7,109,223 B2 Sep. 19, 2006) but with some improvements in the final diastereoselective reduction of the ketone to avoid over-reduction. 2a was reacted with chlorocarbonyloxy-p-nitrobenzene (A1) to provide the reactive carbonate 24 in excellent yield. 24 was then reacted with alendronic acid mono-tetra-n-butylammonium salt (3a) in DMF to provide the conjugate 8 in 35-40% yield (after ion exchange and reverse phase chromatography purification) plus an equivalent amount of recovered 2a (scheme 5).

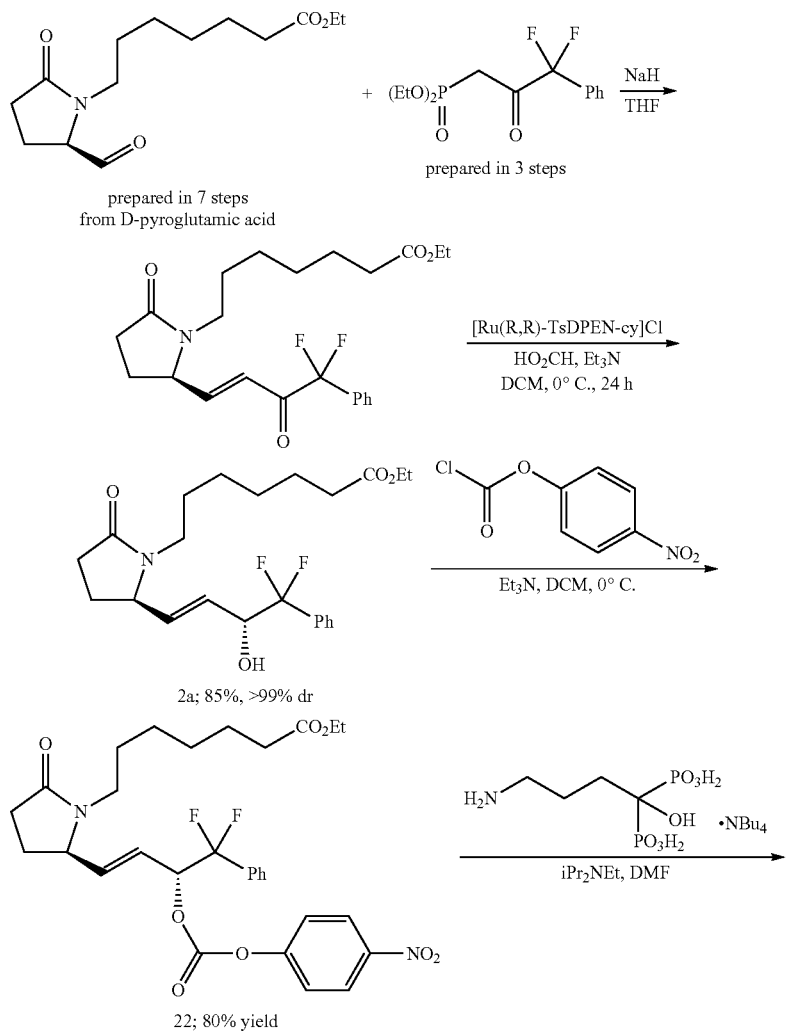

Scheme 5: Preparation of conjugate 8

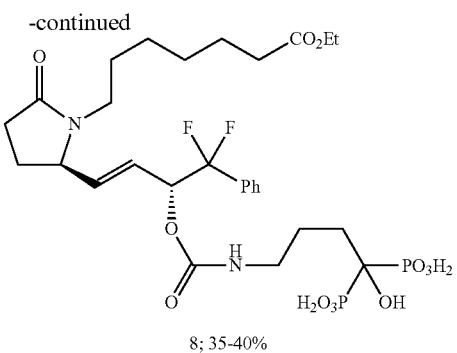

8; 35-40%

Scheme 8

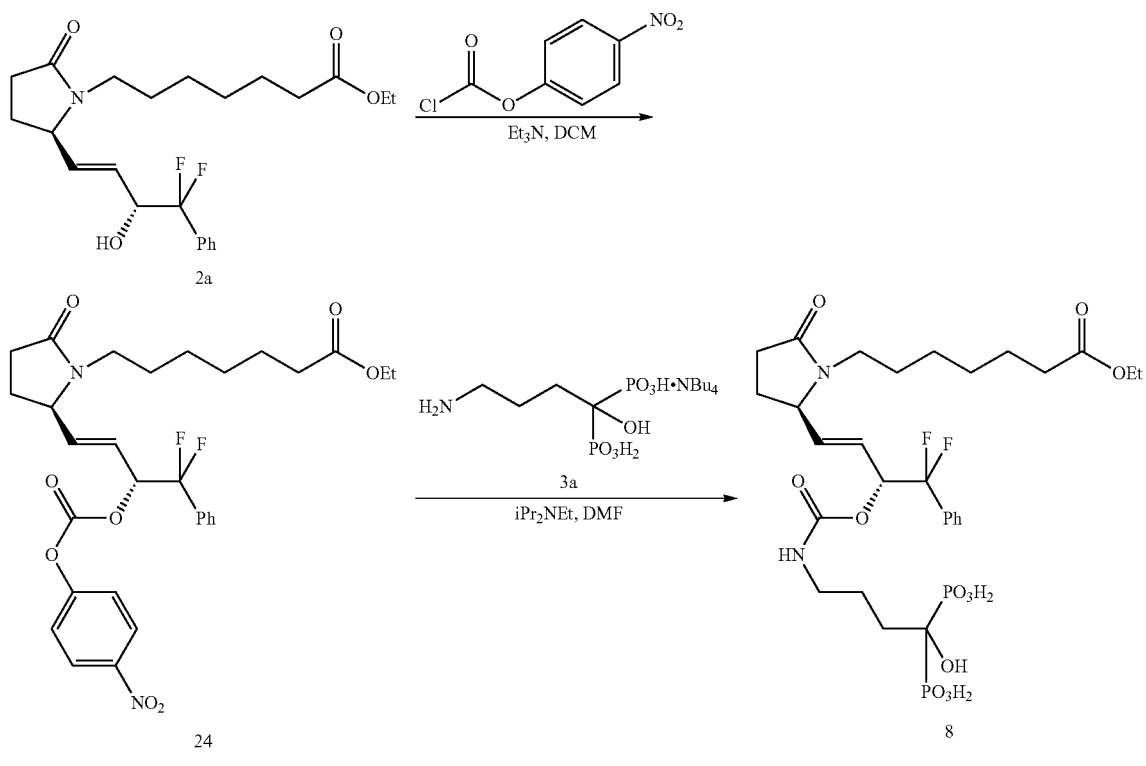

Preparation of Compound 24

A solution of alcohol 2a (1.0 eq.) in dichloromethane (0.2 M) is cooled to 0° C. and treated with triethylamine (2.0 eq.) and 4-nitrophenylchloroformate (1.0 eq.). The mixture is slowly warmed to room temperature and stirred at room temperature for 18 hours. The reaction is then quenched with aqueous $NH_4Cl$ after which the layers are separated and the aqueous phase is extracted with dichloromethane (3×). The organic layers are combined, dried over MgSO4, filtered and concentrated to give an oil that is purified by flash chromatography (80% ethyl acetate/hexanes) to afford 24 as a colorless oil.

$^1$H NMR (600 MHz, $CDCl_3$) δ=8.26 (d, J=9.6 Hz, 2H), 7.52-7.45 (m, 5H), 7.27 (d, J=9.6 Hz, 2H), 5.76 (dd, J=15.3, 7.5 Hz, 1H), 5.71 (dd, J=15.3, 6.9 Hz, 1H), 5.59 (td, J=10.2, 6.6 Hz, 1H), 4.11 (q, J=7.2 Hz, 2H), 4.07 (td, J=7.8, 5.4 Hz, 1H), 3.47 (ddd, J=15.6, 8.4, 7.2 Hz, 1H), 2.61 (ddd, J=13.8, 8.7, 5.4 Hz, 1H), 2.41-2.30 (m, 2H), 2.27 (t, J=7.5 Hz, 2H), 2.24-2.18 (m, 1H), 1.72-1.66 (m, 1H), 1.60 (dt, J=15.2, 7.7 Hz, 2H), 1.46-1.26 (m, 4H), 1.25-1.20 (m, 2H), 1.24 (t, J=7.2 Hz, 3H).

$^{13}$C NMR (125 MHz, $CDCl_3$) δ=174.6 ($C_4$), 173.7 ($C_4$), 155.0 ($C_4$), 151.3 ($C_4$), 145.6 ($C_4$), 139.3 (CH), 132.9 ($C_4$, t, $J_F$=25.1 Hz), 130.8 (CH), 128.6 (CH), 125.8 (CH), 125.3 (CH), 122.7 (CH), 121.6 (CH), 118.9 ($C_4$, t, $J_F$=247.6 Hz), 79.1 (CH, t, $J_F$=32.3 Hz), 60.2 ($CH_2$), 59.5 (CH), 40.5 ($CH_2$), 34.2 ($CH_2$), 29.7 ($CH_2$), 28.7 ($CH_2$), 27.1 ($CH_2$), 26.5 ($CH_2$), 25.0 ($CH_2$), 24.8 ($CH_2$), 14.2 ($CH_3$).

Preparation of Compound 8

To a solution of carbonate 24 (1.0 eq.) in dry DMF (0.2 M) is cannulated a solution of tetra-N-butylammoniumalendronate.5.5$H_2O$ (1.0 eq.) and diisopropylethylamine (5.0 eq) in dry DMF (0.2 M) and the resulting mixture is stirred at room temperature for 3 hours. The DMF is evaporated and the resulting yellow oil is taken up in a 1:1 mixture of ethyl acetate and water. The layers are separated and the aqueous phase is extracted with ethyl acetate (3×). The remaining aqueous phase is passed through an Amberlite IR-120 H+ ion exchange resin column and is lyophilized. The remaining compound is taken up in a small amount of water and purified using Sep-Pac C18 reverse phase flash chromatography (100% H₂O to 50% H₂O/MeOH) affording carbamate 8 as a white solid.

¹H NMR (600 MHz, CD₃OD) δ=7.52-7.46 (m, 5H), 5.73-5.62 (m, 3H), 4.17 (q, J=8.4 Hz, 1H), 4.11 (q, J=7.2 Hz, 2H), 3.37-3.34 (m, 1H), 3.10-3.07 (m, 2H), 2.71 (ddd, J=12.0, 8.4, 5.4 Hz, 1H), 2.39-2.31 (m, 2H), 2.30 (t, J=7.2 Hz, 2H), 2.25-2.19 (m, 1H), 2.05-1.98 (m, 2H), 1.88-1.83 (m, 2H), 1.71-1.66 (m, 1H), 1.60 (dt, J=14.5, 7.2 Hz, 2H), 1.48-1.29 (m, 4H), 1.25-1.22 (m, 2H), 1.24 (t, J=7.2 Hz, 3H).

Several other active carbonate intermediates (such as pentafluorophenyloxycarbonyl- and 2,4-dinitrophenyloxycarbonyl-) were evaluated but proved too unstable or did not give improved yields in these experiments.

EXAMPLE 6

Stability of Conjugate 8

Figure 2:
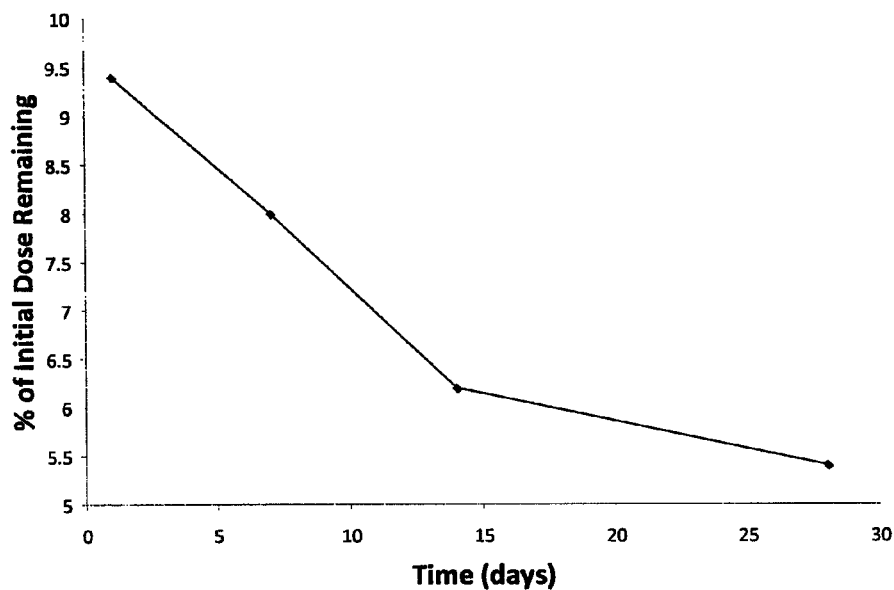
FIG. 2 is a graph showing hydrolysis of the conjugate 8.

The conjugate 8 was incubated at room temperature with 0.1 N NaOH during 24 hours to hydrolyze the ethyl ester essentially quantitatively but the carbamate coupling was not hydrolyzed. Conjugate 8 was incubated at 37° C. in fresh rat plasma and the incubation was followed over time by LC/MS/MS monitoring for appearance of 2 (FIG. 2). After 96 hours no significant liberation of 2 was observed indicating that this conjugate is stable in the blood. To evaluate this conjugate in vivo, we prepared radiolabelled 2. We decided that reduction of the ketone penultimate precursor of 2a with a tritiide reagent might be a facile method. Reduction with the readily commercially available sodium borotritiide was ruled out as it gives predominantly the inactive 15-R-hydroxyl diastereomer. We decided to use the same chiral ruthenium-catalyzed transfer hydrogenation as before (Scheme 6) but substituting tritio-formic acid for formic acid. While without precedent, this was carried out successfully through exchange of oxalic acid with T₂O followed by pyrolysis in a sealed tube to generate the tritio-formic acid. After cooling the catalyst components were added to the pyrolysis vessel to form the reduced catalyst in situ and then the ketone (excess) was added.

Scheme 6: Synthesis of tritiated 2a

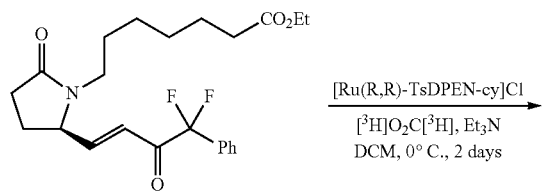

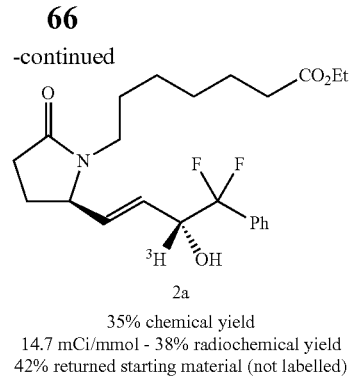

2a

35% chemical yield
14.7 mCi/mmol - 38% radiochemical yield
42% returned starting material (not labelled)

After slow and careful reduction to ensure no over-reduction workup and purification gave the needed tritium-labelled 2a in 35% radiochemical yield (Scheme 6). This synthesis has considerable potential for application to the enantio-selective labelling of secondary alcohols and should be of general interest in the field of radioactive synthesis (S. Arns, A. Moreau and R. N. Young, *J. Label Compd. Radiopharm*, 2010, 53, 205-207). Using tritium-labelled 2a the synthesis of conjugate 8 was repeated for use in dosing rats and determining in vivo stability, uptake into bone and rate of release of 2.

EXAMPLE 7

In Vivo Efficacy

The mixture of radiolabelled 6 and 7 and, separately, radiolabelled 8 is diluted with unlabelled compound as required and then dosed to rats (2 or 3 each) by intravenous administration in water at doses of 5 mg/kg. Tolerability is confirmed and blood samples are withdrawn at various time points and disappearance of both label and conjugate from the blood monitored over about 4 hrs by HPLC with in-line scintillation counting. In addition rats are dosed in a similar manner and at various time points after dosing (4 hr, 1 day, 3 days, 7 days) (2-3 rats per time point) rats are sacrificed and long bones dissected, cleaned, dried and weighed before pyrolyzing in a tissue burner with the liberated water trapped and counting in a scintillation counter. This determines the initial uptake at 4 hrs after dosing and the subsequent release of tritiated 1 or 2 from the bone. Scale-up of the conjugates are initiated to allow a 28 day efficacy study in osteopenic female rats.

Uptake and Release of Conjugate 8: A solution was prepared of carbamate conjugate 8 (specific activity=15.4 mCi/mmol) in PBS. The conjugate was administered intravenously to female Sprauge-Dawley rats at 5 mg/kg. Triplicate sets of rats were euthanized at 1, 7, 14 and 28 days and tritium levels in bone were measured by incineration of the long bones in a biological oxidizer. After an initial 1 day uptake of 9.4%, 5.6% of the initial dose remained after 14 days.

TABLE 1

| Uptake and Release of Radiolabelled Conjugate 8 | |
|---|---|
| Time (days) | % of Initial ³H Dose Remaining |
| 1 | 9.4 |
| 7 | 8.0 |

TABLE 1-continued

Uptake and Release of Radiolabelled Conjugate 8

| Time (days) | % of Initial $^3$H Dose Remaining |
|---|---|
| 14 | 6.2 |
| 28 | 5.6 |

EXAMPLE 8

Preparation of Conjugate 56

A Hydroxyphenylacetic Acid C15 Hydroxyl Conjugate was synthesized as follows.

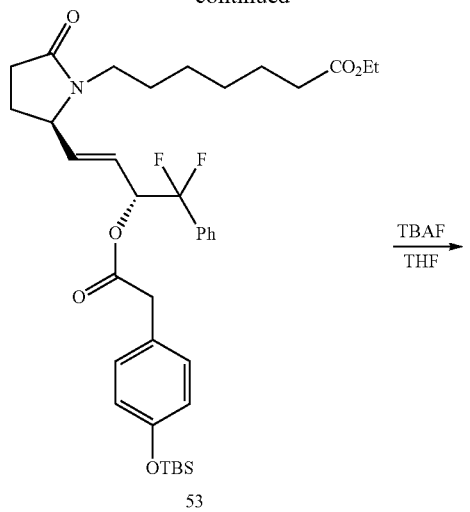

Carboxylic acid 50 (O. Brummer, T. Z. Hoffman, D.-W. Chen, K. D. Janda. *Chem. Comm.* 2001, 19-20) (1.0 eq) was dissolved in DMF and treated with DCC (1.1 eq) and pentafluorophenol (1.2 eq). The mixture was stirred at room temperature for 18 h, after which the precipitate was removed by suction filtration and the solvent was removed under reduced pressure. The product was isolated by filtration through a short pad of silica using 5% ethyl acetate/hexanes as the eluting solvent to afford compound 51 as a colorless liquid. $^1$H NMR (400 MHz, CDCl$_3$) δ=7.21 (d, J=6.8 Hz, 2H), 6.84 (d, J=6.8 Hz, 2H), 3.89 (s, 2H), 0.98 (s, 9H), 0.20 (s, 6H). $^{13}$C NMR (125 MHz, CDCl$_3$) δ=167.9 (C$_4$), 155.5 (C$_4$), 142.1 (m, C$_4$), 140.5 (m, C$_4$), 138.9 (m, C$_4$), 137.2 (m, C$_4$), 130.4 (CH), 124.8 (C$_4$), 120.6 (CH), 39.6 (CH$_2$), 25.8 (CH$_3$), 18.4 (C$_4$), −4.3 (CH$_3$). HRMS (ESI). Found (M+H)$^+$ at 433.1257 for C$_{20}$H$_{22}$F$_5$O$_3$Si. Calculated at 433.1258.

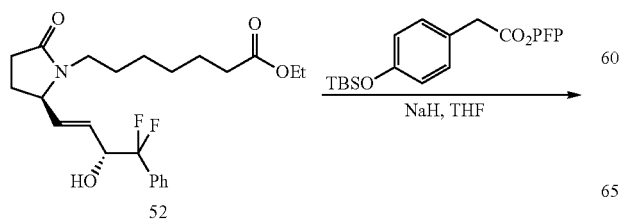

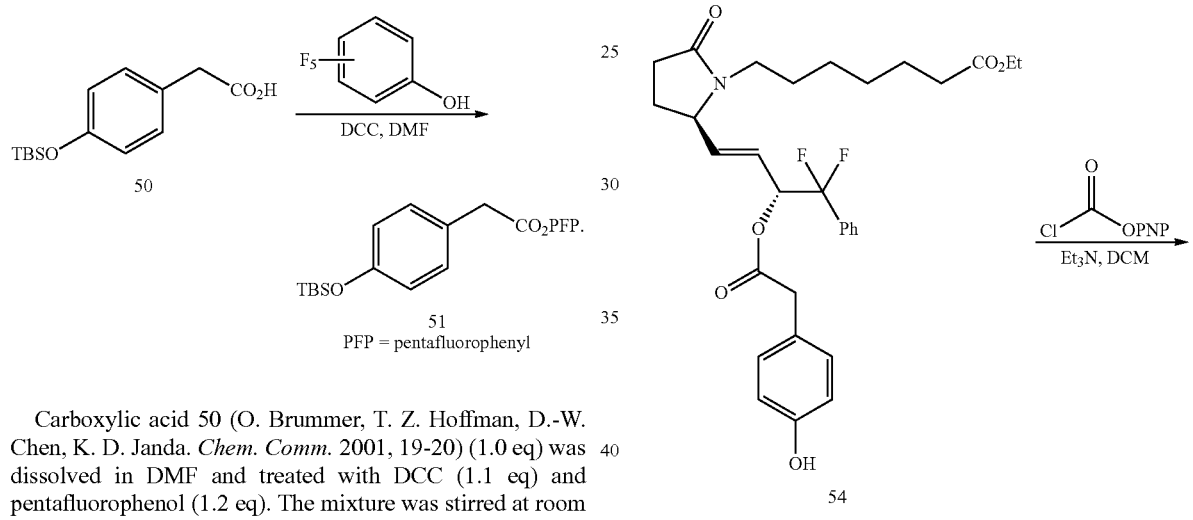

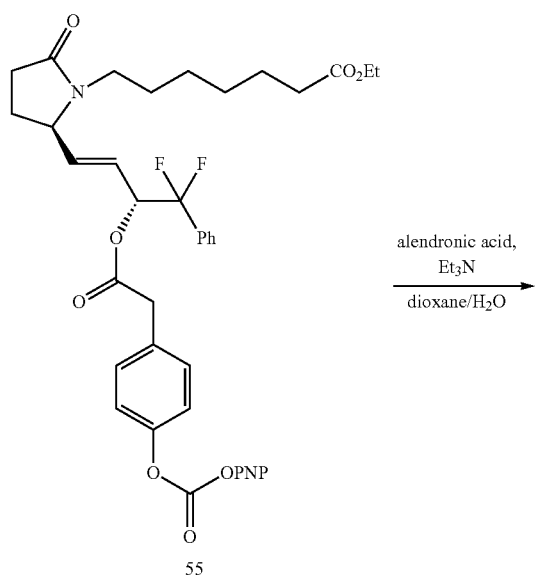

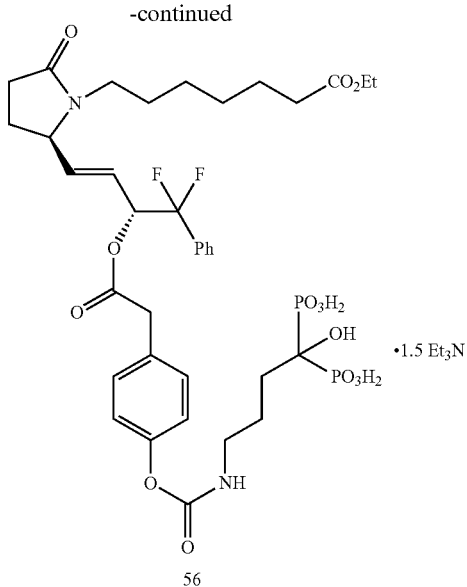

Compound 53.

Alcohol 52 (1.0 eq) was dissolved in THF and treated with NaH (60% in oil, 1.0 eq). After 10 minutes, pentafluorophenyl ester 51 (1.0 eq) was added as a solution in THF and the mixture was stirred at room temperature for 3 hours. The reaction was quenched by the addition of NH$_4$Cl (saturated, aqueous). The layers were separated and the aqueous phase was extracted with diethyl ether (3×). The organic layers were combined, dried over MgSO$_4$, filtered and concentrated and the product was isolated by flash chromatography to afford compound 53 as a colorless oil. $^1$H NMR (400 MHz, CDCl$_3$) δ=7.47-7.37 (m, 5H), 7.02 (d, J=8.5 Hz, 2H), 6.77 (d, J=8.5 Hz, 2H), 5.72 (ddd, J=11.6, 9.3, 6.8 Hz, 1H), 5.63 (dd, J=15.4, 6.6 Hz, 1H), 5.51 (dd, J=15.3, 8.3 Hz, 1H), 4.13 (q, J=7.3 Hz, 2H), 4.00 (td, J=8.0, 5.3 Hz, 1H), 3.54 (d, J=1.9 Hz, 2H), 3.51-3.41 (m, 1H), 2.99 (d, J=5.2 Hz, 1H), 2.63 (ddd, J=13.7, 8.4, 5.3 Hz, 1H), 2.37-2.27 (m, 4H), 2.20-2.11 (m, 1H), 1.66-1.57 (m, 3H), 1.45-1.19 (m, 5H), 1.26 (t, J=7.2 Hz, 3H), 1.00 (s, 9H), 0.20 (s, 6H). $^{13}$C NMR (100 MHz, CDCl$_3$) δ=174.8 (C$_4$), 173.8 (C$_4$), 170.0 (C$_4$), 155.1 (C$_4$), 137.4 (CH), 133.7 (C$_4$, t, J=25.4 Hz), 130.5 (CH), 130.3 (CH), 128.4 (CH), 125.9 (CH, t, J=6.4 Hz), 125.9 (C$_4$), 124.2 (CH, t, J=2.7 Hz), 120.3 (CH), 119.5 (C$_4$, t, J=246.1 Hz), 74.2 (CH, t, J=33.7 Hz), 60.3 (CH$_2$), 59.8 (CH), 40.6 (CH$_2$), 40.4 (CH$_2$), 34.3 (CH$_2$), 29.9 (CH$_2$), 28.9 (CH$_2$), 27.2 (CH$_2$), 26.6 (CH$_2$), 25.8 (CH$_3$), 25.2 (CH$_2$), 24.9 (CH$_2$), 18.3 (C$_4$), 14.4 (CH$_3$), −4.3 (CH$_3$). HRMS (ESI). Found (M+Na)$^+$ at 694.3401 for C$_{37}$H$_{51}$F$_2$NO$_6$SiNa. Calculated at 694.3351.

Compound 54.

Silyl ether 53 (1.0 eq) was dissolved in THF and treated with TBAF (1.0 M in THF, 2.0 eq). After stirring at room temperature for 2 hours the reaction was quenched by the addition of NH$_4$Cl (saturated, aqueous). The layers were separated and the aqueous phase was extracted with diethyl ether (3×). The organic layers were combined, dried over MgSO$_4$, filtered and concentrated and the product was isolated by flash chromatography to afford compound 54 as a yellow oil. $^1$H NMR (400 MHz, CDCl$_3$) δ=7.47-7.39 (m, 5H), 7.01 (d, J=8.0 Hz, 2H), 6.76 (d, J=8.0 Hz, 2H), 5.70-5.65 (m, 1H), 5.58 (dd, J=15.4, 5.3 Hz, 1H), 4.97 (dd, J=15.4, 9.0 Hz, 1H), 4.12 (q, J=7.1 Hz, 2H), 3.94-3.90 (m, 1H), 3.50 (d, J=4.5 Hz, 2H), 3.42-3.37 (m, 1H), 2.48-2.43 (m, 1H), 2.30-2.24 (m, 4H), 2.13-2.06 (m, 1H), 1.61-1.55 (m, 2H), 1.49-1.43 (m, 1H), 1.39-1.16 (m, 10H). No phenol OH observed. $^{13}$C NMR (100 MHz, CDCl$_3$) δ=175.4 (C$_4$), 174.1 (C$_4$), 169.9 (C$_4$), 156.0 (C$_4$), 135.4 (CH), 133.6 (C$_4$, t, J=20.3 Hz), 130.6 (CH), 130.4 (CH), 128.4 (CH), 126.0 (C$_4$, t, J=4.9 Hz), 124.8 (CH), 124.3 (CH), 119.5 (C$_4$, t, J=197.1 Hz), 116.2 (CH), 73.5 (CH, t, J=26.4 Hz), 60.4 (CH$_2$), 60.0 (CH), 40.8 (CH$_2$), 40.5 (CH$_2$), 34.3 (CH$_2$), 29.9 (CH$_2$), 28.8 (CH$_2$), 26.9 (CH$_2$), 26.5 (CH$_2$), 25.0 (CH$_2$), 24.8 (CH$_2$), 14.3 (CH$_3$). HRMS (ESI). Found (M+H)$^+$ at 558.2653 for C$_{31}$H$_{38}$F$_2$NO$_6$. Calculated at 558.2667.

Compound 55.

Phenol 54 (1.0 eq) was dissolved in dichloromethane and treated with Et$_3$N (3.0 eq) and 4-nitrophenylchloroformate (1.1 eq). After stirring at room temperature for 2 hours the reaction was quenched by the addition of NH$_4$Cl (saturated, aqueous). The layers were separated and the aqueous phase was extracted with dichloromethane (3×). The organic layers were combined, washed with H$_2$O and brine, dried over MgSO$_4$, filtered and concentrated. The crude product was filtered quickly through a short pad of silica gel and the product 55 was used directly in the next step without further manipulation.

Compound 56.

Carbonate 55 (1.0 eq) was dissolved in 1,4-dioxane. To this was added a solution of alendronic acid (1.25 eq) and Et$_3$N (6.0 eq) in water, immediately generating a yellow color. After 2.5 hours the reaction was diluted with H$_2$O and the layers were separated. The aqueous phase was extracted with dichloromethane (3×), then it was freeze dried to give a waxy yellow solid. The product was isolated by C18 reverse phase flash chromatography using gradient elution from H$_2$O to MeOH, affording compound 56 as a white solid. $^1$H NMR (500 MHz, CDCl$_3$) δ=7.45-7.42 (m, 1H), 7.39-7.32 (m, 4H), 7.08 (d, J=8.5 Hz, 2H), 7.02 (d, J=8.5 Hz, 2H), 6.64 (bs, 1H), 5.72-5.66 (m, 1H), 5.61 (dd, J=15.3, 6.9 Hz, 1H), 5.50 (dd, J=15.3, 8.4 Hz, 1H), 4.70 (bs, 4H), 4.11 (q, J=7.1 Hz, 2H), 4.01-3.97 (m, 1H), 3.55 (s, 2H), 3.46-3.40 (m, 1H), 3.31-3.26 (m, 2H), 3.04 (q, J=7.1 Hz, 9.2H—protons from 1.52. Et$_3$N salt), 2.63-2.57 (m, 1H), 2.37-2.26 (m, 4H), 2.19-2.01 (m, 5H), 1.64-1.56 (m, 3H), 1.43-1.19 (m, 10H), 1.25 (t, J=7.1 Hz, 13.8H—protons from 1.52. Et$_3$N salt). $^{13}$C NMR (150 MHz, CDCl$_3$) δ=174.8 (C$_4$), 173.9 (C$_4$), 169.7 (C$_4$), 154.9 (C$_4$), 150.9 (C$_4$), 137.8 (CH), 133.6 (t, J$_F$=25.5 Hz, C$_4$), 130.7 (CH), 130.1 (CH), 129.6 (C$_4$), 128.6 (CH), 125.8 (t, J$_F$=6.1 Hz, CH), 124.2 (CH), 122.0 (CH), 119.5 (t, J$_F$=248.2 Hz, C$_4$), 74.4 (t, J$_F$=32.8 Hz, CH), 73.8 (C$_4$), 60.3 (CH$_2$), 59.8 (CH), 45.3 (CH$_2$), 42.1 (CH$_2$), 40.6 (CH$_2$), 31.5 (CH$_2$), 30.0 (CH$_2$), 29.8 (CH$_2$), 28.9 (CH$_2$), 27.2 (CH$_2$), 26.6 (CH$_2$), 25.3 (CH$_2$), 25.0 (CH$_2$), 24.1 (CH$_2$), 14.4 (CH$_3$), 8.7 (CH$_3$). HRMS (ESI). Found (M+H)$^+$ at 833.2602 for C$_{36}$H$_{49}$F$_2$N$_2$O$_{14}$. Calculated at 833.2627. Detected free acid in QTOF-MS.

EXAMPLE 9

Biological Results for 4-Hydroxyphenylacetic Acid C15 Hydroxyl Conjugate 56

Plasma Stability of Conjugate.

Aliquots from a stock solution of compound 56 in PBS were used to prepare 100 μg/mL samples of conjugate in fresh and boiled rat plasma with a final volume of 100 μL. These samples were incubated at 37° C. over 24 h. At each time point the appropriate samples were injected with acetonitrile (100 μL) and centrifuged. The supernatant solution was analyzed by comparison to a standard curve for the presence of liberated EP4 agonist acid 2 using LC-MS (QTOF). Ester 3 rapidly hydrolyzes ($t_{1/2}$<5 min) to acid 2 in fresh or boiled rat plasma.

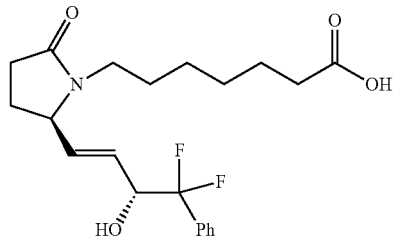

2

TABLE 2

Figure 3:
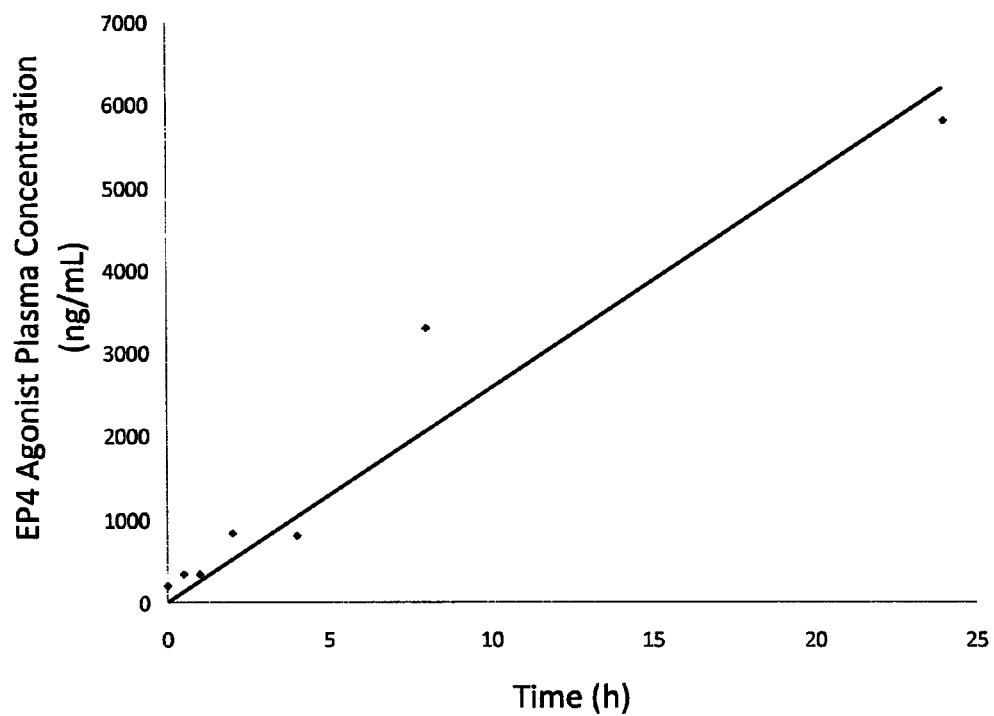
FIG. 3 is a graph showing hydrolysis of the conjugate 56.

Plasma Stability of Conjugate 56 (Figure 3)

Concentration of EP4 Agonist Acid 2 (ng/mL)

| Time (h) | Fresh Rat Plasma | Boiled Rat Plasma |
|---|---|---|
| 0 | 199 | 0 |
| 0.5 | 343 | — |
| 1 | 337 | — |
| 2 | 833 | — |
| 4 | 803 | 302 |
| 8 | 3289 | — |
| 24 | 5787 | 3170 |

Uptake and Release of Conjugate 56A solution was prepared of conjugate 56 (radiolabelled at the C15 carbon as described in S. Arns, A. Moreau, R. N. Young. *J. Labelled Compd. Radiopharm.* 2010, 205-207., specific activity=7.25 mCi/mmol) in PBS. The conjugate was administered intravenously to female Sprague-Dawley rats at 10 mg/kg. Triplicate sets of rats were euthanized at 6 h, 48 h, 168 h and 336 h and tritium levels in bone was measured by incineration of the long bones in a biological oxidizer. After an initial 6 h uptake of 5.9%, 1.4% of the initial dose remained after 14 days.

TABLE 3

Uptake And Release of Radiolabelled Conjugate 56

| Time (h) | % of Initial $^3$H Dose Remaining |
|---|---|
| 6 | 5.9 |
| 48 | 4.9 |
| 168 | 2.2 |
| 336 | 1.4 |

EXAMPLE 10

Preparation of Model Conjugates

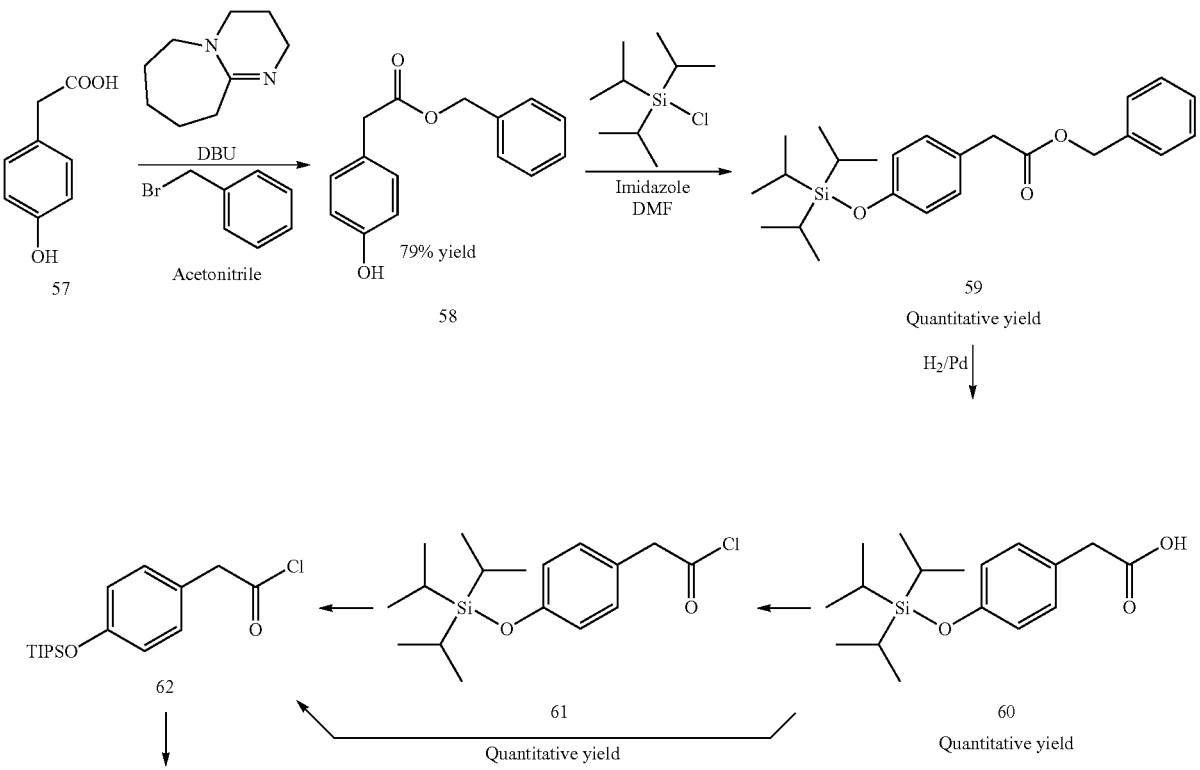

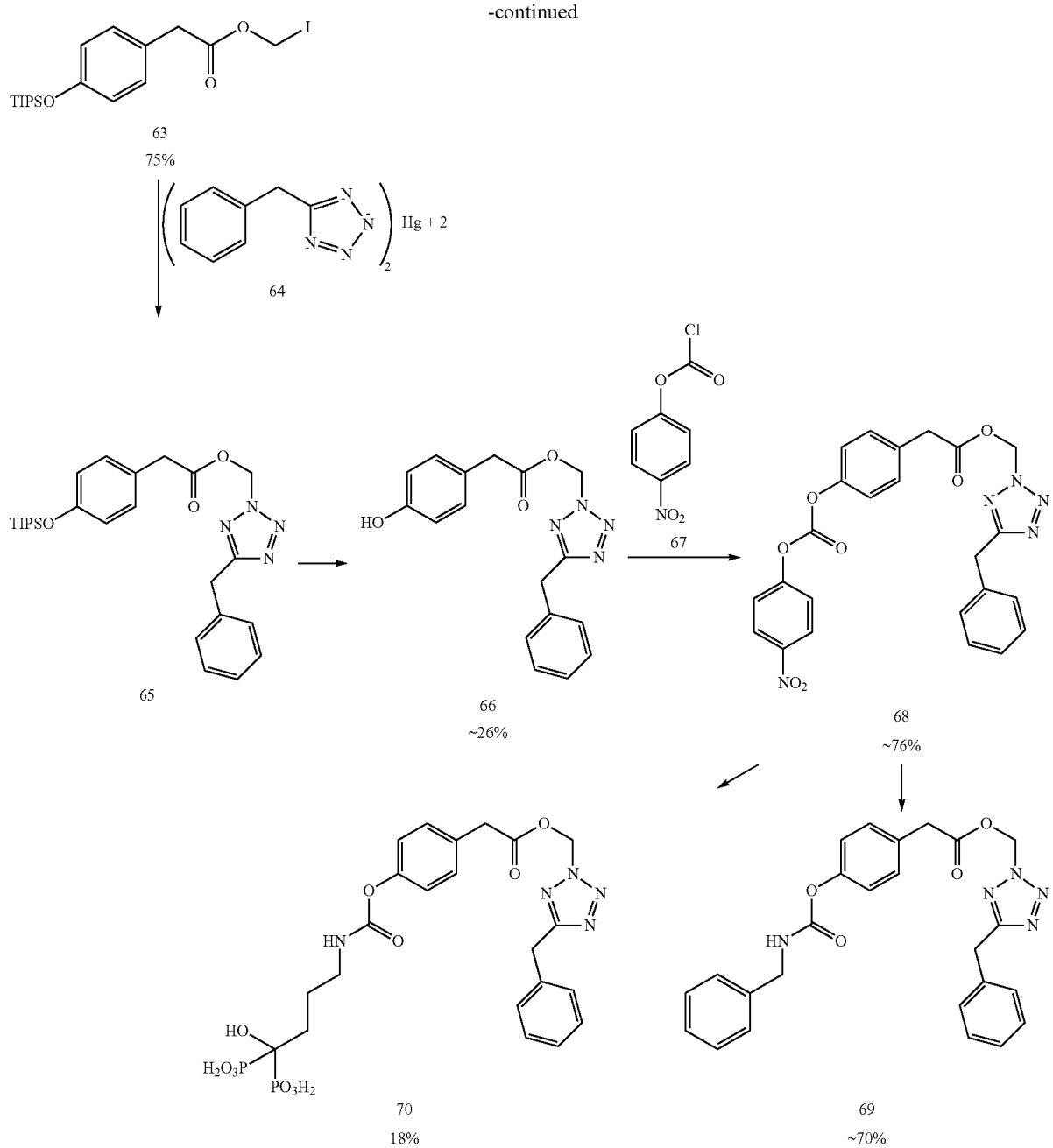

-continued

Synthesis of Compound 58:

Compound 57 (2.1375 g, 14.05 mmol), 1,8-diazabicycloundec-7-ene (DBU) (2.5211 mL, 16.86 mmol) and benzyl bromide (1.83 mL, 15.45 mmol) was dissolved in 30 mL $CH_3CN$ under argon atmosphere Then refluxed for 18 hrs followed by addition of 100 mL EtOAc. Organic layer was washed twice with 100 mL amount brine solution, dried over $Na_2SO_4$. Removed the solvent using rotary evaporator. Then did a gradient flash column with hexanes and EtOAc to collect product 58. $^1H$ NMR (400 MHz, $CDCl_3$) δ 7.40-7.29 (m, 5H), 7.15 (d, J=8.4 Hz, 2H), 6.83-6.73 (m, 2H), 5.13 (s, 2H), 3.60 (s, 2H). $^{13}C$ NMR (101 MHz, $CDCl_3$) δ 130.5, 128.5, 128.2, 115.4, 66.6, 40.4.

Synthesis of Compound 59:

Compound 58 (2.6786 g, 11.05 mmol) and imidazole (1.6559 g, 24.32 mmol) was dissolved in dimethyl amino formamide (DMF) in argon atmosphere. TIPSCl (2.8 mL, 13.27 mmol) was added slowly to the reaction mixture. After 18 hrs removed the solvent by rotary evaporator. Then added 50 mL EtOAC and 50 mL saturated citric acid solution to the crude mixture. Separated the organic layer. Washed the organic layer with saturated $NaHCO_3$ solution. Dried the organic layer with $Na_2SO_4$. Removed solvent by vacuum. Then performed a hexane-EtOAc gradient flash column to isolate product 59. $^1H$ NMR (400 MHz, $CDCl_3$) δ 7.42-7.30 (m, 5H), 7.19-7.11 (m, 2H), 6.88-6.81 (m, 2H), 5.15 (s, 2H), 3.62 (s, 2H), 1.38-1.20 (m, 3H), 1.16-1.04 (m, 18H). $^{13}C$ NMR (101 MHz, $CDCl_3$) δ 171.7, 155.2, 135.9, 130.2, 128.5, 128.1, 126.3, 119.9, 66.5, 40.6, 17.9, 12.7.

Synthesis of Compound 60:

Took compound 59 (4.4071 g, 11.06 mmol) and Pd/C (0.2254 g) in a round bottom flask under hydrogen atmosphere. Then added MeOH (15 mL) and EtOAc (15 mL) mixture in the flask. Left to stir for 24 hrs. Then filtered the mixture through a celite plugh. Removed solvent by rotary evaporator. Then performed a hexane-EtOAc gradient flash column to isolate product 60. $^1$H NMR (400 MHz, CDCl$_3$) δ 7.12 (d, J=8.6 Hz, 2H), 6.83 (d, J=8.6 Hz, 2H), 3.57 (s, 2H), 1.31-1.17 (m, 3H), 1.13-1.03 (m, 18H). $^{13}$C NMR (101 MHz, CDCl$_3$) δ 177.3, 155.4, 130.3, 125.6, 120.0, 40.1, 17.9, 12.7.

Synthesis of Compound 62:

Under argon atmosphere dissolved 60 (0.3720 g, 1.21 mmol) in CH$_2$Cl$_2$ (5 mL). Followed by addition of (COCl)$_2$ (0.31 mL, 3.61 mmol) and 20 μL of DMF. Left the reaction overnight. By rotary evaporator removed the solvent and unreacted (COCl)$_2$. Added 10 mL toluene to the flask and removed the solvent again by rotary evaporator. Checked formation of 61 by IR. Without any further purification went for the next step of the reaction. Added distilled CH$_2$Cl$_2$ (5 mL) and ZrCl$_4$ to the flask. It formed a green solution instantly. Then added trioxane (0.1086 g, 1.21 mmol) (previously dissolved in 5 mL CH$_2$Cl$_2$) to the reaction mixture. Slowly the green color disappeared and formed a light yellow color solution. After 2 hrs added 10 mL saturated NaHCO$_3$ solution to stop the reaction. Then performed an extraction and collected the organic layer. Dried the organic layer with Na$_2$SO$_4$. Then performed a hexanes-EtOAc gradient column chromatography to isolate the product 62. $^1$H NMR (500 MHz, CDCl$_3$) δ 7.18 (d, J=2.6 Hz, 2H), 6.71 (d, J=8.4 Hz, 2H), 5.62 (s, 2H), 3.54 (s, 2H), 1.25 (dd, J=15.0, 7.3 Hz, 3H), 1.05 (dd, J=7.4, 3.6 Hz, 18H).

Synthesis of Compound 63:

Under argon atmosphere dissolved 62 (0.0850 g, 0.2381 mmol) and NaI (0.3569 g, 2.3812 mmol) in dry acetone (10 mL). Left to reflux overnight. Removed solvent using rotary evaporator. Added 20 mL EtOAc and 20 mL water to dissolve the reaction mixture. Collected the organic layer. Washed the organic layer with saturated Na$_2$S$_2$O$_3$ solution to remove excess iodine from the mixture. Then performed a hexanes-EtOAc gradient column chromatography to isolate the product 63. $^1$H NMR (500 MHz, CDCl$_3$) δ 7.13-7.07 (m, 2H), 6.87-6.78 (m, 2H), 5.90 (s, 2H), 3.57 (s, 2H), 1.30-1.17 (m, 3H), 1.13-1.06 (m, 18H). $^{13}$C NMR (126 MHz, CDCl$_3$) δ 169.9, 155.5, 130.3, 124.8, 120.1, 119.9, 40.5, 30.7, 17.9, 12.6.

Synthesis of Compound 66:

Under argon atmosphere 0.0385 g (0.1443 mmol) of 64 and 0.1295 g (0.28906 mmol) of 63 was dissolved in 10 mL of C$_2$H$_4$Cl$_2$. Then heated to reflux for 24 hrs. By TLC the reaction seems to complete. Then removed the solvent by rotary evaporator. At this point the reaction mixture contains mixture of 65 and 66. To remove TIPS protection dissolved the crude reaction mixture with 10 mL of THF. Added 2 equivalent of TBAF and stirred for 2 hrs. Then removed solvent with rotary evaporator followed by a gradient flash with C$_2$H$_2$Cl$_2$-MeOH (0 to 20% MeOH). Compound 18 was isolated in overall 26% yield.

Synthesis of Compound 68:

Under argon atmosphere 66 (0.0278 g, 0.0857 mmol) was dissolved in dry 10 mL CH$_2$Cl$_2$. Et$_3$N (36 μL, 0.2571 mmol) was added to the mixture. 67 (0.0207 g, 0.10286 mmol) (dissolved in 5 mL CH$_2$Cl$_2$) was added to the reaction mixture and let to stir for 24 hrs. Then removed the solvent by rotary evaporator and performed a gradient flash column (on silica) with hexanes and EtOAc. Got pure product 68. $^1$H NMR (400 MHz, CDCl$_3$) δ 8.39-8.29 (m, 2H), 7.54-7.47 (m, 2H), 7.40-7.24 (m, 7H), 7.22-7.13 (m, 2H), 6.05 (d, J=12.4 Hz, 2H), 4.38 (s, 2H), 3.61 (s, 2H). $^{13}$C NMR (101 MHz, CDCl$_3$) δ 169.6, 155.2, 150.9, 150.1, 145.7, 133.6, 130.7, 130.5, 130.2, 129.2, 128.9, 128.5, 127.9, 127.6, 126.2, 125.4, 121.7, 121.2, 115.8, 67.0, 39.7, 31.8.

Synthesis of Compound 69:

Under argon atmosphere dissolved 68 (0.0189 g, 0.03861 mmol), diidopropylethylamine (34 μL, 0.19307 mmol) and benzylamine (5 μL, 0.042475 mmol) in DMF. Left to stir for 24 hrs. Then removed solvent by rotary evaporator and performed a gradient flash silica column with hexanes-EtOAc system to get pure 69. $^1$H NMR (500 MHz, CDCl$_3$) δ 7.44-7.30 (m, 7H), 7.29-7.22 (m, 3H), 7.12 (d, J=8.3 Hz, 3H), 5.77 (s, 1H), 5.42 (s, 1H), 4.47 (dd, J=12.3, 6.0 Hz, 2H), 3.64 (s, 2H).

Synthesis of Compound 70:

0.0210 g (0.0429 mmol) of 68 was dissolved in dioxane (10 mL). Alendronic acid (0.0128 g, 0.05149 mmol) and Et$_3$N (30 μL, 0.2145 mmol) was dissolved separately in 10 mL water. Then water solution was added to the dioxane solution and let to stir for 24 hrs. Added 25 mL of water to the reaction mixture. Washed the solution 3 times with 20 mL EtOAc. Then left the water layer for freeze-dry. Checked the soid by 1H and seemed that there is product. Then passed it through a C18 sep-pack to purify the product using water-MeOH as the solvent system to get purified product. $^1$H NMR (400 MHz, D$_2$O) δ 7.38 (t, J=7.0 Hz, 4H), 7.34-7.27 (m, 2H), 7.16 (s, 2H), 7.10 (s, 1H), 6.35 (s, 2H), 4.38 (s, 2H), 3.35 (s, 2H), 2.22 (s, 4H), 2.11-1.79 (m, 2H).

EXAMPLE 11

Preparation of Conjugate 75

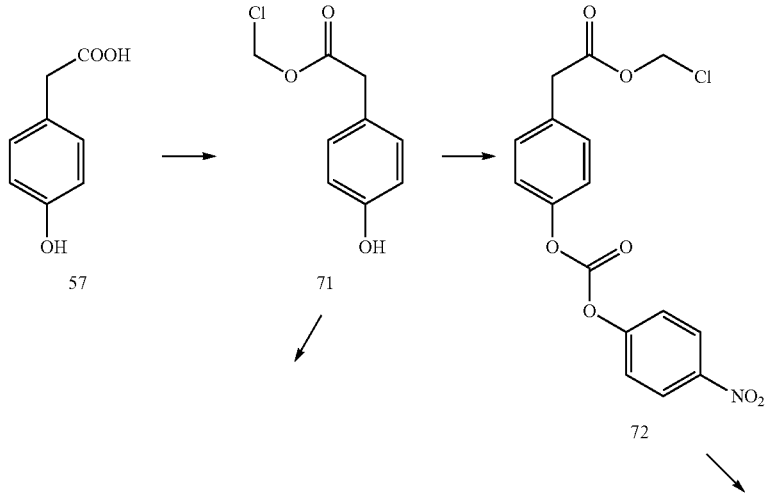

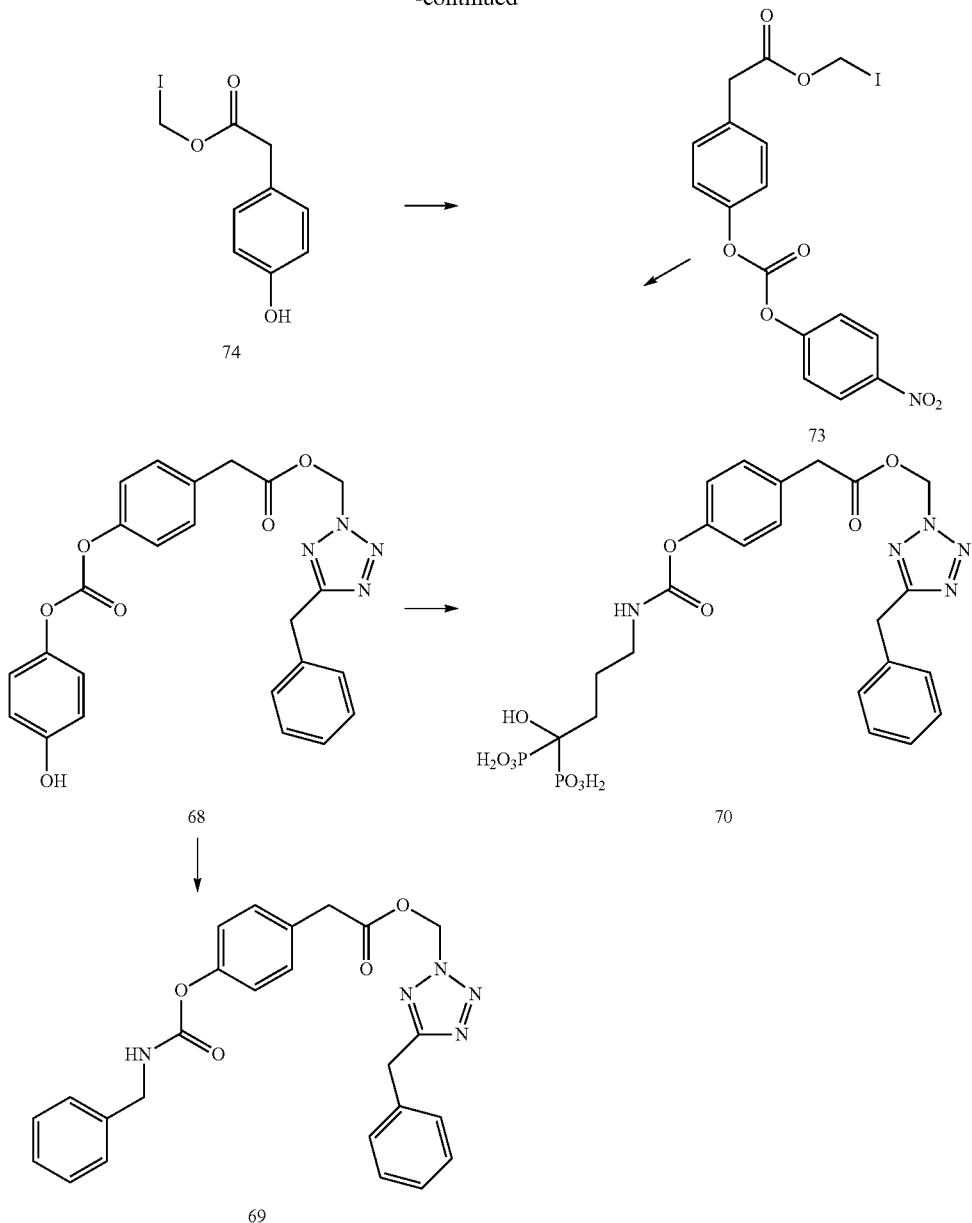

Synthesis of Compound 71:

Compound 57 (3.41 g, 22.412 mmol) and Bu$_4$N.HSO$_4$ (0.7609 g, 2.2412 mmol) were mixed in 40 mL of C$_2$H$_2$Cl$_2$. Followed by slow addition of NaHCO$_3$ solution (3.7656 g, 44.824 mmol dissolved in 40 mL water) to the mixture. At this point bubble was formed from CO$_2$ evolution. Then slowly added 1.1336 mL of ClCH$_2$OSO$_2$Cl (11.206 mmol) to the reaction mixture. Left the reaction overnight. Next morning collected the organic layer. Extracted the aqueous layer once with EtOAc. Combined the organic layers and dried over Na$_2$SO$_4$. After removing the solvent by rotary evaporator, purified the product 71 by a gradient column (hexanes-EtOAc) chromatography using silica column. $^1$H NMR (400 MHz, CDCl$_3$) δ 7.14 (d, J=8.6 Hz, 2H), 6.79 (d, J=8.6 Hz, 2H), 5.70 (s, 2H), 4.97 (s, 1H), 3.63 (s, 2H). $^{13}$C NMR (126 MHz, CDCl$_3$) δ 130.6, 115.6, 68.9, 31.6.

Synthesis of Compound 72:

Under argon atmosphere compound 23 (1.7988 g, 8.9662 mmol) was dissolved in CH$_2$Cl$_2$ (15 mL) at 0° C. Added 1.4996 mL (10.7594 mmol) of Et$_3$N to the reaction mixture. Followed by addition of 67 (2.1680 g, 10.7594 mmol) dissolved in 5 mL CH$_2$Cl$_2$. Let the reaction slowly reach the room temperature and leave to stir for 24 hrs. Removed the solvent by rotary evaporator and performed a gradient (hexanes-EtOAc) column (silica) chromatography to isolate the pure product 72. $^1$H NMR (400 MHz, CDCl$_3$) δ 8.37-8.32 (m, 2H), 7.55-7.46 (m, 2H), 7.39 (d, J=8.7 Hz, 2H), 7.29 (dd, J=6.3, 2.4 Hz, 2H), 5.74 (s, 2H), 3.76 (s, 2H). $^{13}$C NMR (101 MHz, CDCl$_3$) δ 169.2, 155.2, 150.9, 150.0, 131.2, 130.7, 125.4, 121.7, 121.0, 69.0, 40.2.

Synthesis of Compound 73:

Under argon atmosphere 72 (0.6787 g, 1.8558 mmol) was dissolved in dry acetone (20 mL). NaI (2.7816 g, 18.558 mmol) was added to the flask and left to reflux for an hour. Then removed the solvent by rotary evaporator. Added 50 mL saturated Na₂S₂O₃ solution and 50 mL EtOAc to the flask. Then extracted the organic layer. Washed the organic layer with brine solution. Dried the organic layer over Na₂SO₄ and removed the solvent by rotary evaporator. Then performed a gradient silica column with hexanes and EtOAc to collected the pure product 73. ¹H NMR (400 MHz, CDCl₃) δ 8.39-8.30 (m, 2H), 7.55-7.46 (m, 2H), 7.38 (d, J=8.6 Hz, 2H), 7.32-7.25 (m, 2H), 5.95 (s, 2H), 3.71 (s, 2H). ¹³C NMR (101 MHz, CDCl₃) δ 169.2, 155.2, 150.9, 150.0, 131.1, 130.7, 125.4, 121.7, 121.0, 40.5, 30.3.

Under argon atmosphere dissolved 71 (0.0865 g, 0.4311 mmol) in dry acetone (15 mL) and added NaI (0.6463 g, 4.3116 mmol) to the solution. Then left the mixture to reflux overnight. Removed the solvent by rotary evaporator. Added 30 mL Na₂S₂O₃ saturated solution and 30 mL EtOAc to dissolve everything. Extracted the organic layer and dried over Na₂SO₄. Removed solvent by rotary evaporator and collected crude 74. ¹H NMR (400 MHz, CDCl₃) δ 7.14 (d, J=8.5 Hz, 2H), 6.87-6.75 (m, 2H), 5.92 (s, 2H), 3.83 (s, 1H), 3.59 (s, 2H). ¹³C NMR (101 MHz, CDCl₃) δ 210.9, 169.9, 155.2, 130.5, 124.4, 115.6, 69.6, 40.36. Then dissolved the compound in 10 mL CH₂Cl₂ and added diisopropylethylamine (0.22 mL, 1.2935 mmol) to the solution. Followed by addition of 67 (0.1042 g, 0.517 mmol). After an hour removed solvent. By TLC the crude seems to be combination of too many compounds with very close retention time. But product 73 peak was there. Further purification was not performed as other method gives high yield of 73.

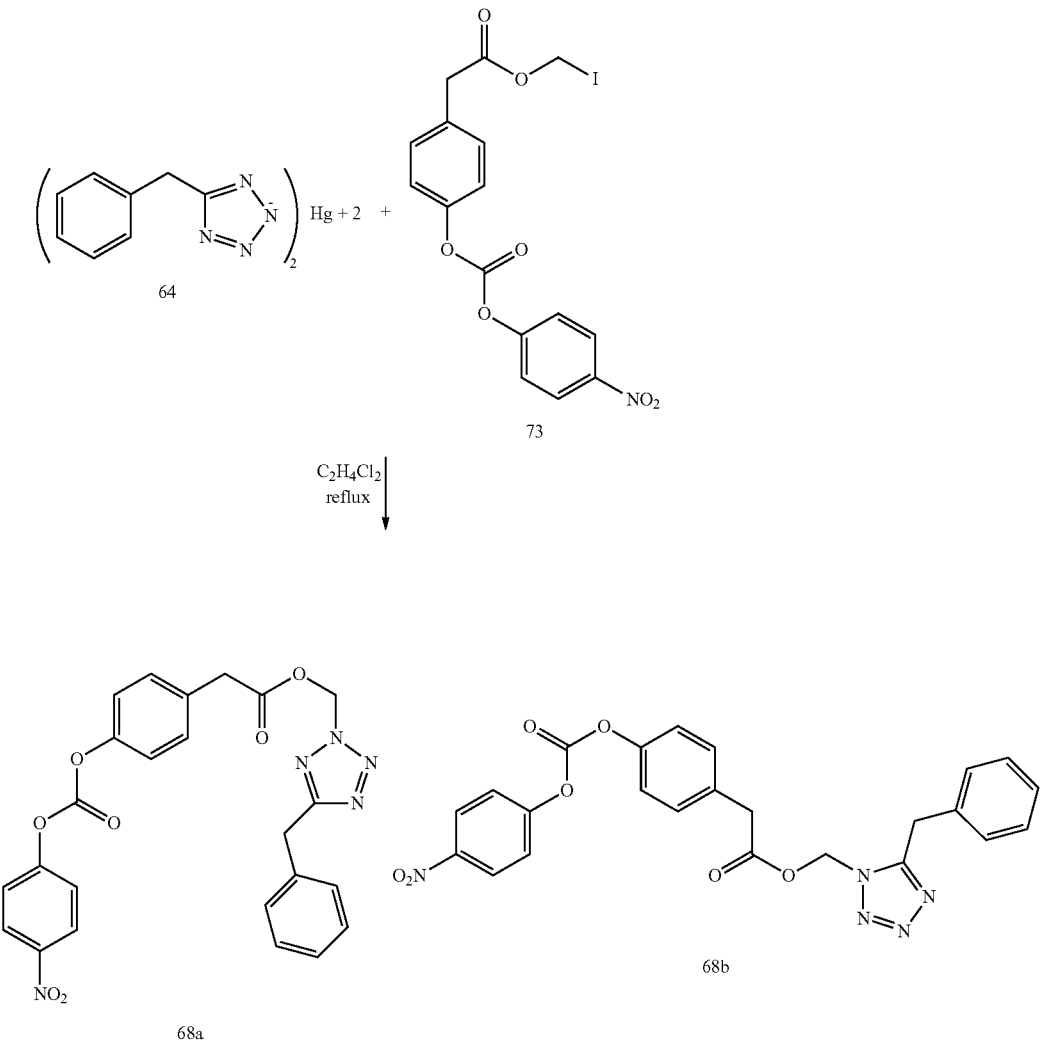

Synthesis of Compound 68:
Under argon atmosphere 64 (0.1995 g, 0.38361 mmol), 73 (0.1753 g, 0.3836 mmol) and 50 mL C₂H₄Cl₂ were taken in a round bottom flask and left to reflux for 24 hrs. Removed solvent and performed a gradient silica column with hexane and EtOAc. Isolated two isomers of product 68a and 68b.

68a ¹H NMR (500 MHz, CDCl₃) δ 8.34-8.30 (m, 2H), 7.55-7.45 (m, 2H), 7.41-7.21 (m, 9H), 6.47 (s, 2H), 4.29 (s, 2H), 3.74 (s, 2H). ¹³C NMR (101 MHz, CDCl₃) δ 169.3, 166.6, 161.8, 155.23 (s), 151.0, 150.1, 135.8, 130.9, 130.7, 128.8, 127.2, 125.5, 121.8, 121.1, 71.6, 39.8, 31.7.

68b ¹H NMR (400 MHz, CDCl₃) δ 8.36-8.28 (m, 2H), 7.53-7.42 (m, 2H), 7.36-7.27 (m, 3H), 7.26 (d, J=1.7 Hz, 4H), 7.20-7.13 (m, 2H), 6.05 (s, 2H), 4.36 (s, 2H), 3.59 (s, 2H). ¹³C NMR (101 MHz, CDCl₃) δ 171.1, 169.6, 155.2, 154.6, 150.9, 150.2, 145.7, 133.6, 130.7, 129.2, 128.5, 127.9, 125.4, 121.7, 121.2, 67.0, 39.7, 31.6.

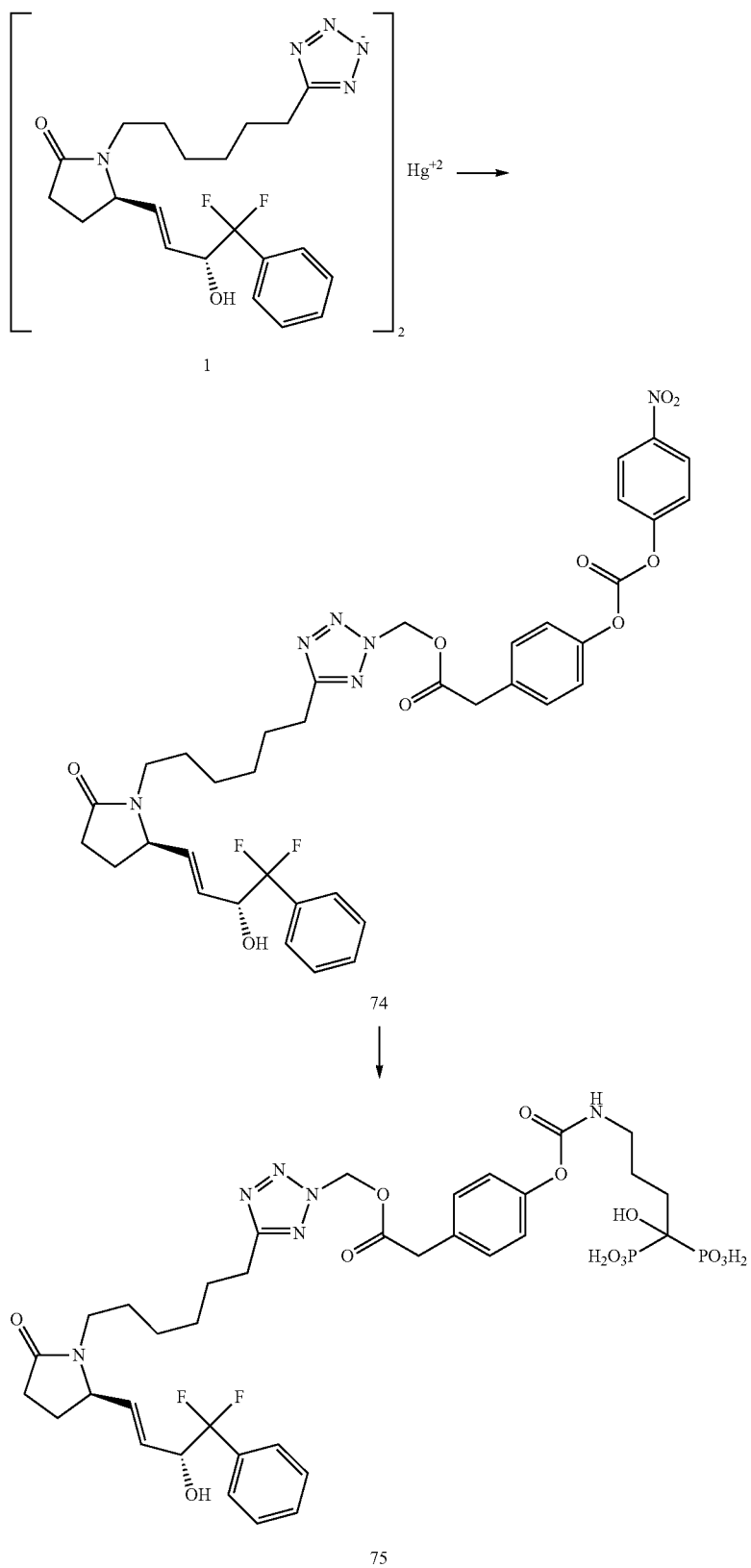

Synthesis of Compound 74:

Under argon atmosphere 74 (0.0777 g, 0.1254 mmol), 73 (0.2292 g, 0.5017 mmol) and 10 mL $C_2H_4Cl_2$ were taken in a round bottom flask and left to reflux for 24 hrs. Removed solvent and performed a gradient silica column with hexane and EtOAc to isolate product 74. $^1$H NMR (400 MHz, $CDCl_3$) δ 8.34 (d, J=9.3 Hz, 2H), 7.56-7.40 (m, 7H), 7.35 (d, J=8.7 Hz, 2H), 7.30-7.20 (m, 3H), 6.46 (s, 2H), 5.69 (d, J=6.0 Hz, 2H), 4.68-4.49 (m, 1H), 4.10-3.98 (m, 1H), 3.75 (s, 2H), 3.50-3.26 (m, 1H), 2.96-2.84 (m, 2H), 2.83-2.64 (m, 2H), 2.45-2.27 (m, 2H), 2.25-2.12 (m, 1H), 1.79 (s, 2H), 1.68 (s, 2H), 1.54-1.34 (m, 4H). $^{13}$C NMR (101 MHz, $CDCl_3$) δ 174.8, 169.2, 167.8, 155.2, 150.9, 150.1, 145.7, 135.2, 131.0, 130.7, 130.3, 128.3, 127.5, 125.9, 125.4, 121.7, 121.0, 74.3, 74.0, 71.4, 60.1, 40.5, 39.8, 30.0, 28.5, 27.5, 27.0, 26.3, 25.3.

In a similar procedure synthesis of the 3H labelled compound 74 was performed.

Synthesis of Compound 75:

In a round bottom flask compound 74 (0.0365 g, 0.0487 mmol) was dissolved in dioxane (4 mL). In a separate flask alendronic acid (0.0146 g, 0.0585 mmol) and $Et_3N$ (41 μL, 0.2925 mmol) were dissolved in 4 mL water. The water solution had a pH of 8 at this point. Then added the water solution to the dioxane solution. The pH of the solution was maintained at 8 by adding more $Et_3N$ as per requirement. Let mixture stir for 2 hrs. Added 25 mL of water and 25 mL of EtOAc. Collected the water layer. Then freeze-dried the crude mixture. Further purification was performed by passing through a C18 sep-pack column Pure compound was collected after freeze-drying of the product fractions. $^1$H NMR (400 MHz, MeOD) δ 7.48 (dd, J=18.8, 3.3 Hz, 5H), 7.32-7.21 (m, 1H), 7.16-6.98 (m, 1H), 6.51 (d, J=5.1 Hz, 2H), 5.79-5.57 (m, 2H), 4.56 (d, J=9.2 Hz, 1H), 4.16 (d, J=4.6 Hz, 1H), 3.74 (s, 2H), 2.94-2.80 (m, 2H), 2.72 (dd, J=13.5, 5.6 Hz, 1H), 2.34 (d, J=3.6 Hz, 2H), 2.29-1.91 (m, 4H), 1.88-1.59 (m, 4H), 0.92 (t, J=6.8 Hz, 1H).

In a similar procedure synthesis of the 3H labelled compound 75 was performed.

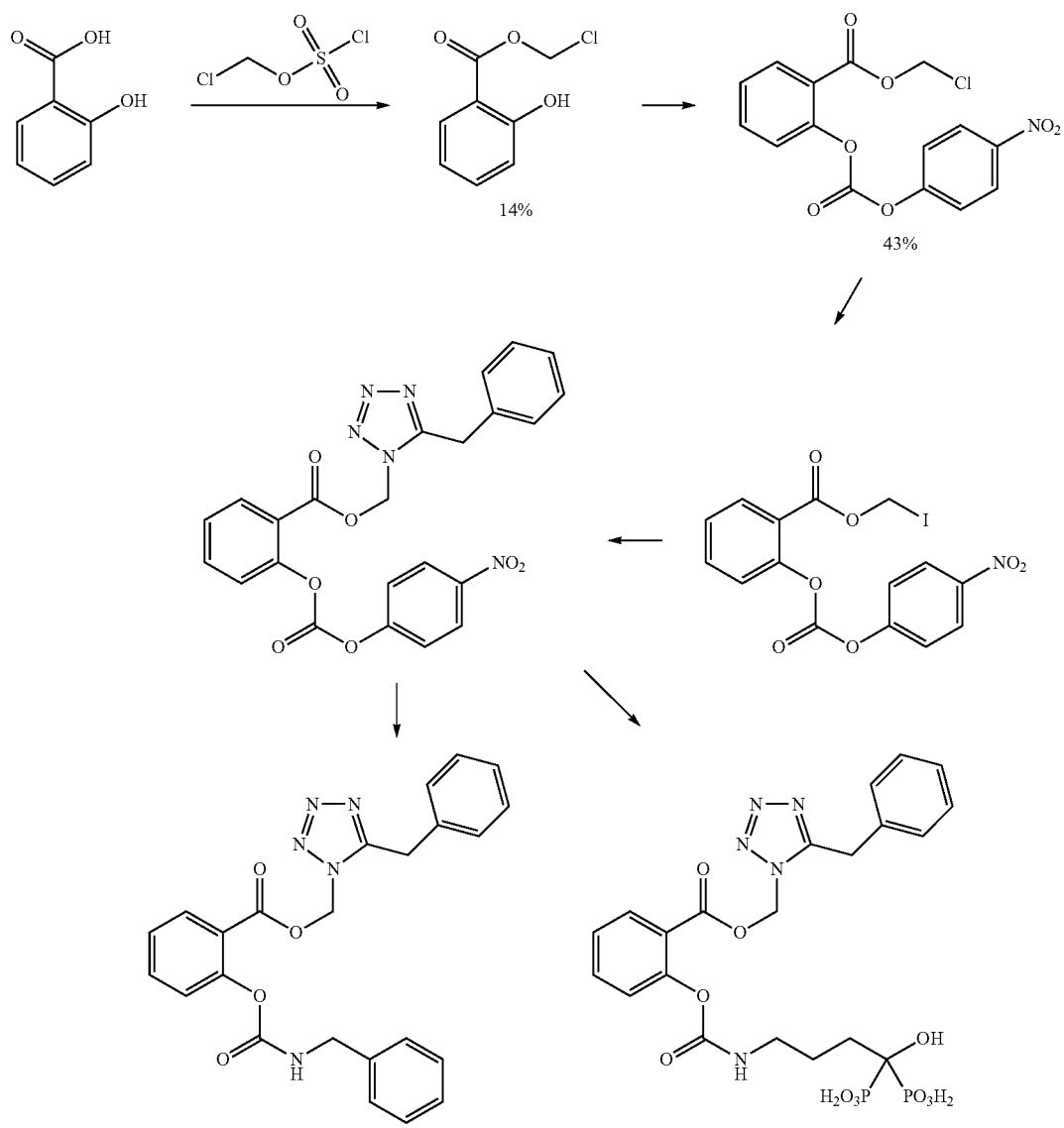

85
86
-continued
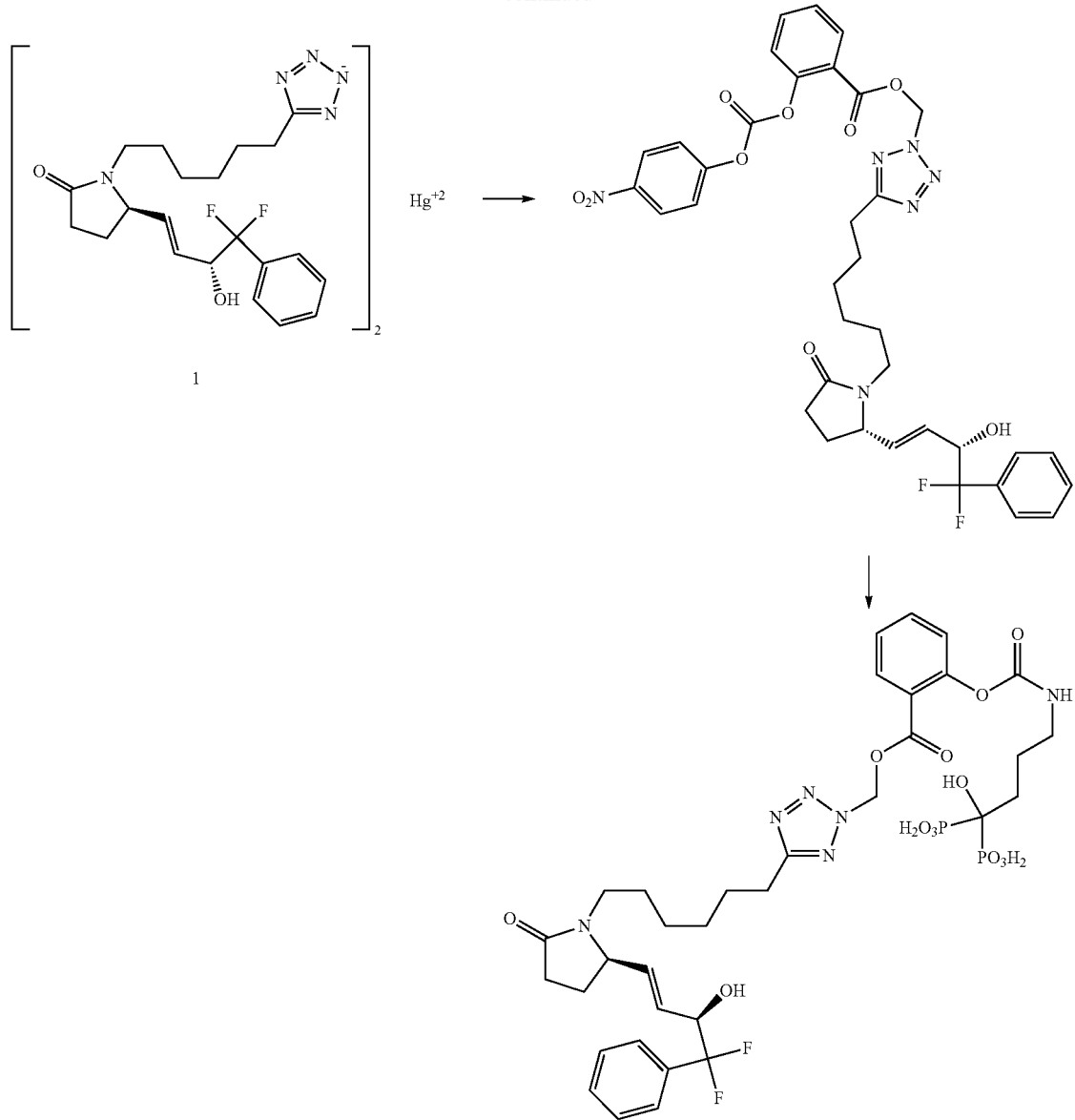
Further Synthesis Methods for Compounds 74-75
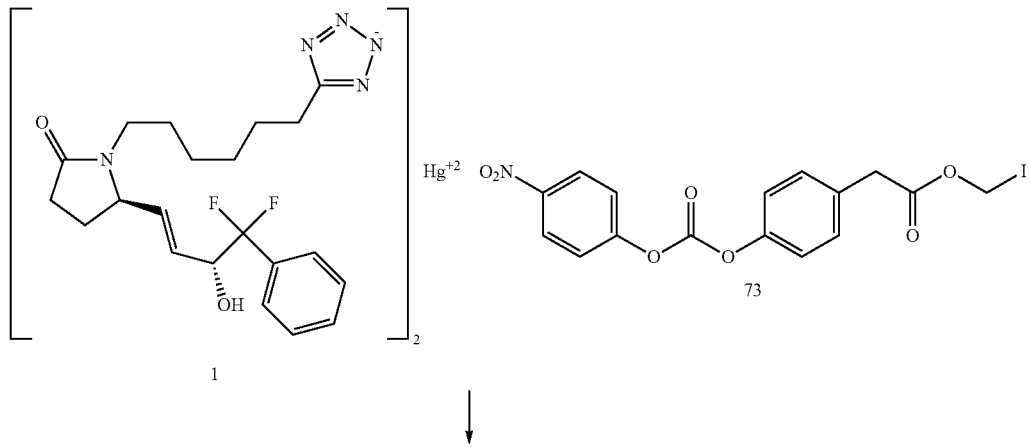

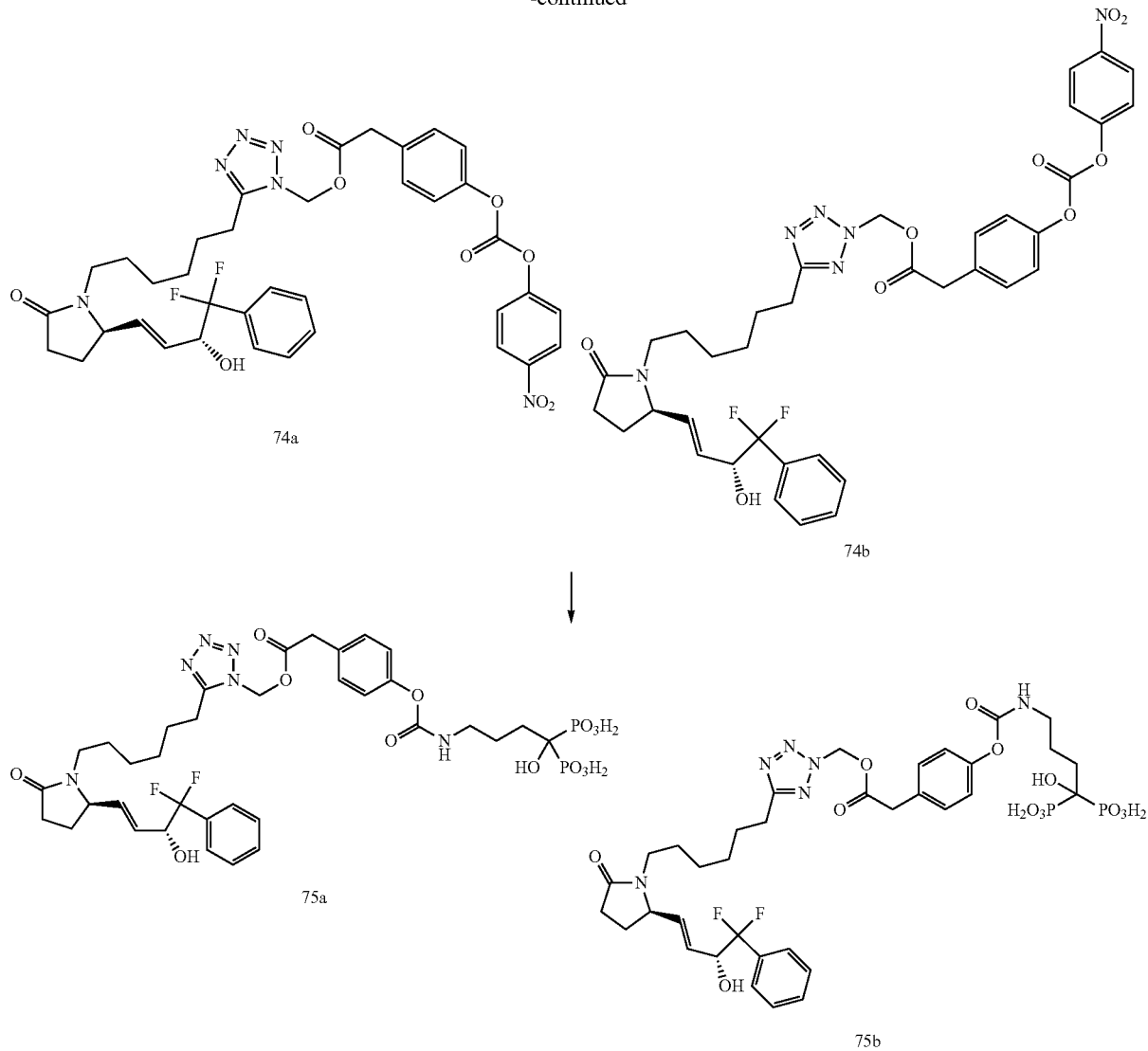

Synthesis of Compound 74:

Under argon atmosphere 1 (0.4773 g, 0.4601 mmol), 73 (1.2621 g, 2.7606 mmol) and 5 mL $C_2H_4Cl_2$ were taken in a round bottom flask and left to reflux for 24 hrs. Removed solvent by vacuum and performed a gradient silica column with hexane and EtOAc to isolate product 74a and 75b. 74a $^1$H NMR (400 MHz, $CDCl_3$) δ 8.39-8.29 (m, 2H), 7.55-7.41 (m, 5H), 7.36 (d, J=8.7 Hz, 2H), 7.26 (d, J=2.1 Hz, 2H), 6.46 (s, 1H), 5.68 (t, J=5.8 Hz, 2H), 4.67-4.53 (m, 1H), 4.09-4.00 (m, 1H), 3.75 (s, 1H), 3.47-3.35 (m, 1H), 2.96-2.86 (m, 2H), 2.81-2.69 (m, 1H), 2.53 (d, J=5.3 Hz, 1H), 2.36 (d, J=7.2 Hz, 2H), 2.26-2.12 (m, 1H), 1.85-1.73 (m, 2H), 1.73-1.63 (m, 2H), 1.49-1.35 (m, 4H), 1.29 (dd, J=14.0, 6.8 Hz, 3H). 74b $^1$H NMR (400 MHz, $CDCl_3$) δ 8.38-8.30 (m, 2H), 7.56-7.41 (m, 6H), 7.36-7.30 (m, 2H), 7.28-7.25 (m, 2H), 6.23 (d, J=2.5 Hz, 2H), 5.70 (dd, J=8.2, 6.2 Hz, 2H), 4.66-4.52 (m, 1H), 4.05 (d, J=5.6 Hz, 1H), 3.73 (s, 2H), 3.48-3.30 (m, 1H), 2.94-2.86 (m, 2H), 2.81 (s, 2H), 2.44-2.26 (m, 2H), 2.23 (s, 1H), 1.80 (dd, J=9.8, 5.4 Hz, 2H), 1.65 (dd, J=12.9, 9.4 Hz, 4H), 1.43 (dd, J=13.9, 6.8 Hz, 5H), 0.94 (d, J=6.7 Hz, 1H).

In a similar procedure synthesis of the 3H labelled compound 74 was performed.

Synthesis of Compound 75a:

Procedure A:

In a round bottom flask compound 74a (0.0361 g, 0.0482 mmol) was dissolved in 1 mL DMF. Then 0.0336 g (0.0579 mmol) of alendronic acid mono tetra-n-butyl ammonium salt and $Et_3N$ (41 μL, 0.2895 mmol) were added to the flask. Left to stir for an hour. Removed the solvent by freeze-dry technique. The crude compound passed through a $Na^+$ ion-exchange column. This left the $Na^+$ salt of the product with nitrophenol. Dissolved the crude compound in water and washed the water layer with ether twice to remove the undesired nitrophenol. Collected the water layer and freeze dried the water layer to get $Na^+$ salt form of the product. After passing through a $H^+$ ion exchange column this salt could be transformed into free form 75a. $^1$H NMR (500 MHz, MeOD) δ 7.48 (dt, J=14.0, 6.7 Hz, 5H), 7.26 (d, J=8.5 Hz, 2H), 7.06 (d, J=8.4 Hz, 2H), 6.53 (d, J=7.1 Hz, 2H), 5.68 (dd, J=26.0, 7.4 Hz, 2H), 4.56 (d, J=6.5 Hz, 1H), 4.16 (d, J=5.9 Hz, 1H), 3.81-3.63 (m, 2H), 3.37 (s, 1H), 3.23 (t, J=6.8 Hz, 2H), 2.90 (t, J=7.4 Hz, 2H), 2.73 (s, 1H), 2.42-2.29 (m, 2H), 2.22 (d, J=5.2 Hz, 1H), 2.12 (d, J=15.0 Hz, 2H), 2.05-1.87 (m, 2H), 1.77 (dd, J=14.7, 7.3 Hz, 2H), 1.70 (s, 1H), 1.52-1.19 (m, 7H). $^{13}$C NMR (126 MHz, MeOD) δ 176.1, 169.7, 167.3, 134.3, 129.9, 129.7, 127.8, 125.8, 121.5, 73.8, 71.3, 60.4, 41.1, 40.2, 39.0, 29.6, 28.1, 27.3, 26.5, 25.9, 24.9, 24.5. HRMS calcd 859.2639 ($C_{35}H_{46}F_2N_6O_{13}P_2$+H). found 859.2627.

Procedure B:

Compound 74a was dissolved in 0.2 mL of dioxane. A stock solution of alendronic acid (0.0579 mmol) and $Et_3N$ (0.1518 mmol) in 0.2 mL water were added to the solution. Followed by addition of further 24 μL $Et_3N$ (0.1737 mmol) to the solution. Stirred the solution for an hour. Freeze dried the solution and thus removed excess $Et_3N$ for the crude. At this point the crude contained product 27a, $Et_3N$ and nitrophenol. Crude was dissolved in water. The water solution was washed with ether to remove excess nitrophenol. Then freeze dried the water layer. Crude product was dissolved in 50-50 water-methanol mixture. Then passed through a acid ion exchange column to isolate the product 75a.

In a similar procedure synthesis of the $^3$H labelled compound 75a was performed.

Synthesis of Compound 75b:

Compound 74b (0.2681 g, 0.3581 mmol) was dissolved in 1.5 mL of dioxane. A stock solution of alendronic acid (0.4297 mmol) and $Et_3N$ (0.8594 mmol) in 1.5 mL water was added to the solution. Followed by addition of further 181 μL $Et_3N$ (1.2890 mmol) to the solution. Stirred the solution for an hour. Freeze dried the solution and thus removed excess $Et_3N$ from the crude. At this point the crude contained product 75b, $Et_3N$ and nitrophenol. Crude was dissolved in water. The water solution was washed with ether to remove excess nitrophenol. Then freeze dried the water layer. By 1H NMR and HRMS product 75b was confirmed. $^1$H NMR (500 MHz, MeOD) δ 7.58-7.36 (m, 5H), 7.28 (d, J=33.7, 8.5 Hz, 2H), 7.04 (d, J=23.0, 8.5 Hz, 2H), 6.35 (s, 2H), 5.69 (dd, J=26.1, 7.7 Hz, 2H), 4.56 (d, J=6.4 Hz, 1H), 4.16 (d, J=5.6 Hz, 1H), 3.73 (s, 1H), 3.48 (s, 1H), 3.38 (dd, J=13.7, 7.8 Hz, 1H), 3.24 (d, J=6.8 Hz, 2H), 2.97 (dd, J=19.3, 11.7 Hz, 3H), 2.83 (s, 1H), 2.78-2.63 (m, 1H), 2.35 (dd, J=13.5, 7.4 Hz, 2H), 2.22 (dd, J=12.9, 7.2 Hz, 1H), 2.17-1.96 (m, 7H), 1.77 (dd, J=15.2, 7.6 Hz, 3H), 1.41 (t, J=25.3 Hz, 4H).

HRMS calcd 857.2493 ($C_{35}H_{46}F_2N_6O_{13}P_2$, M−H ion). found 857.2488.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A compound according to Formula I, or a pharmaceutically acceptable salt thereof:

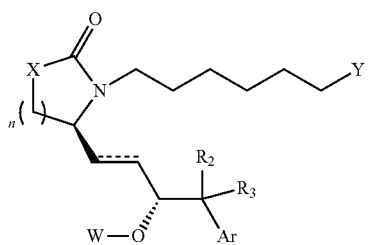

Formula I wherein:

X is —$CH_2$—, —S—, —O—, or —NH—;

$R_2$ and $R_3$ are each independently —H or halo;

Ar is aryl;

Y is —C(O)$OR_1$, tetrazole, or N-trityl-tetrazole;

$R_1$ is H or optionally substituted lower alkyl;

W is

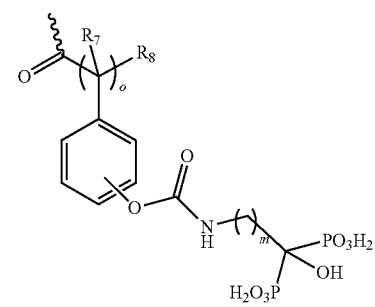

$R_7$ and $R_8$ are each independently H, small alkyl, cycloalkyl group or $CF_3$;

--- is a double or single bond, n is 1, 2 or 3;

m is 1, 2, 3, 4, 5, or 6; and o is 0, 1, 2, 3, 4, 5, or 6.

2. A pharmaceutical composition comprising the compound of claim 1 in combination with a pharmaceutically acceptable carrier.

3. A method of selectively delivering a compound to bone or an associated site, the method comprising administering an effective amount of the compound of claim 1 to a subject in need thereof.

4. The method of claim 3 wherein the associate site comprises a site adjacent to a bone in need of treatment.

5. The method of claim 3 wherein the bone in need of treatment is selected from the group consisting of a green stick fracture, compound fracture, lateral fracture, pathologic fracture resulting from an invasive tumor, compression fracture, and fracture requiring a surgical procedure for realignment of a bone.

6. A method of treating or preventing a condition associated with abnormal or excessive bone loss, or with abnormal or reduced bone resorption, or with abnormal calcium metabolism comprising administering an effective amount of the compound of claim 1 to a subject in need thereof.

7. The method of claim 6, wherein the condition is selected from the group consisting of osteoporosis, glucocorticoid-induced osteoporosis, Paget's disease, abnormally increased bone turnover, bone graft, periodontal disease, alveolar bone loss, tooth loss, bone fracture, periprostheticosteolysis, osteogenesisimperfecta, and metastatic bone disease.

8. The method of claim 6 wherein the subject is a human.

9. A compound that is represented by the following chemical structure, or a pharmaceutically acceptable salt thereof:

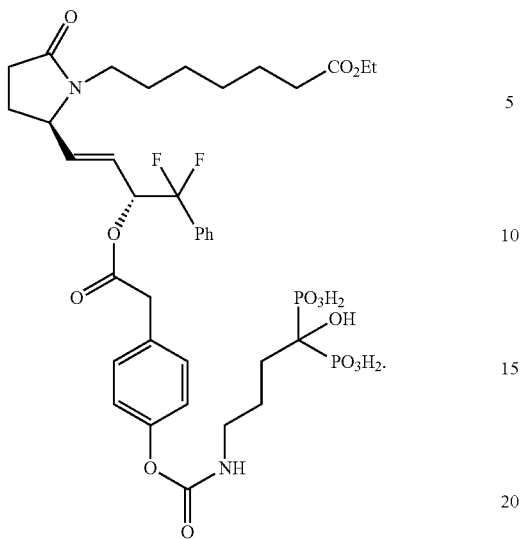
10. A pharmaceutical composition comprising the compound of claim 9 in combination with a pharmaceutically acceptable carrier.
* * * * *